US007183262B2

(12) United States Patent
Li et al.

(10) Patent No.: US 7,183,262 B2
(45) Date of Patent: Feb. 27, 2007

(54) METHOD FOR SELECTIVE EXPRESSION OF THERAPEUTIC GENES BY HYPERTHERMIA

(75) Inventors: Chuan-Yuan Li, Durham, NC (US); Qian Huang, Shanghai (CN); Mark W. Dewhirst, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 10/172,399

(22) Filed: Jun. 14, 2002

(65) Prior Publication Data
US 2003/0045495 A1 Mar. 6, 2003

Related U.S. Application Data

(60) Provisional application No. 60/298,305, filed on Jun. 14, 2001.

(51) Int. Cl.
*A01N 43/04* (2006.01)
*A01N 63/00* (2006.01)
*C12N 15/00* (2006.01)
*C12N 15/63* (2006.01)
*C07H 21/04* (2006.01)

(52) U.S. Cl. .................... 514/44; 435/320.1; 435/455; 424/93.21; 536/23.5; 536/24.1

(58) Field of Classification Search ............. 435/320.1, 435/455; 514/44; 536/23.5, 24.1, 23.1; 424/93, 21
See application file for complete search history.

(56) References Cited

U.S. PATENT DOCUMENTS

| | | | | |
|---|---|---|---|---|
| 5,614,381 | A | 3/1997 | Bromley et al. | 435/69.1 |
| 5,688,773 | A | 11/1997 | Chiocca et al. | 514/44 |
| 5,922,685 | A | 7/1999 | Rakhmilevich et al. | 514/44 |
| 5,994,104 | A | 11/1999 | Anderson et al. | 435/69.52 |
| 6,200,598 | B1 | 3/2001 | Needham | 424/450 |

FOREIGN PATENT DOCUMENTS

| | | |
|---|---|---|
| EP | 507 825 B1 | 8/1996 |
| EP | 819 758 A2 | 1/1998 |
| EP | 439 095 | 5/1998 |
| WO | WO90/11092 | 10/1990 |
| WO | WO95/00178 | 1/1995 |
| WO | WO95/16771 | 6/1995 |
| WO | WO97/12970 | 4/1997 |
| WO | WO97/46263 | 12/1997 |
| WO | WO98/06864 | 2/1998 |
| WO | WO99/42137 | 8/1999 |
| WO | WO99/65466 | 12/1999 |

OTHER PUBLICATIONS

Rudinger, 1976, Peptide Hormones, Edited by Parsons, University Park Press, Baltimore, p. 1-7.*
Kaye et al., 1990, Proc. Natl. Acad. Sci. USA, vol. 87, pp. 6922-6926.*
Skolnick et al., 2000, Trends in Biotech, vol. 18, p. 34-39.*
Braiden et al., 2000, Human gene Therapy, vol. 11, p. 2453-2463.*
Computer prinout, result 1, US Patent 5,994,104, p. 1-2.*
Computer prinout, result 7, US Patent 5,994,104, p. 10-11.*
Deonarain, M., 1998, Expert Opin. Ther. Pat., Vol. 8, pp. 53-69.*
Verma et al., Sep. 1997, Nature, vol. 389, pp. 239-242.*
Eck et al., 1996, Goodman & Gilman's The Pharmacological Basis of Therapeutics, McGraw-Hill, New York, p. 77-101.*
Gorecki, D., 2001, Expert Opin. Emerging Drugs, 6(2): 187-198.*
Davis, C. G., 1990, The New Biologist, vol. 2, No. 5, p. 410-419.*
Maruyama et al., 2003, Molecular Immunology, vol. 40, p. 319-326.*
Computer printout pp. 7-8, see result 13.*
Computer printout pp. 9-10, see result 12.*
Tsang, et al., *New vectors for augmented levels of heat inducible gene expression,* Cancer Gene Therapy 4, No. 6 (1997) ABSTRACT.
Pennington, et al., *Quantitative assessment of heat inducible gene expression,* Cancer Gene Therapy 4, No. 6 (1997) ABSTRACT.
Vasanwala, et al. *A novel gene expression vector induced by heat shock, chemotherapy and radiation,* Cancer Gene Therapy 4, No. 6 (1997) ABSTRACT.
Bramson, et al., *Pre-existing immunity to adenovirus does not prevent tumor regression following intratumoral administration of a vector expressing IL-12 but inhibits virus dissemination,* Gene Therapy 4:1069-1076 (1997).
Coughlin et al., *Interleukin-12 and Interleukin-18 Synergistically Induce Murine Tumor Regression Which Involves Inhibition of Angiógenesis,* J. Clin. Invest. 101, No. 6:1441-1452 (Mar. 1998).
Deshmukh et al., *Immunogene therapy with interleukin-2-secreting fibroblasts for intracerebrally metastasizing breast cancer in mice,* J. Neurosurg 94:287-292 (Feb. 2001).
Dias, et al., *Multiple Molecular and Cellular Changes Associated with Turour Stasis and Regression During IL-12 Therapy of a Murine Breast Cancer Model,* Int. J. Cancer 75:151-157 (1998).
Dreano, et al., *High-level, heat-regulated synthesis of proteins in eukaryotic cells,* Gene 49:1-8 (1986).
Dreano, et al., *Antibody Formation Against Heat-Induced Gene Products Expressed in Animals,* Bio/Technology 1340-1343 (Nov. 1988).

(Continued)

*Primary Examiner*—Shin-Lin Chen
(74) *Attorney, Agent, or Firm*—Jenkins, Wilson, Taylor & Hunt, P.A.

(57) ABSTRACT

A method for controlling in vivo heat-inducible gene expression for provision of therapeutic polypeptide. The method includes the steps of: (a) providing a construct comprising a polynucleotide encoding a therapeutic polypeptide, wherein the polynucleotide is operatively linked to a heat-inducible promoter; (b) administering the construct to a warm-blooded vertebrate at a site at or near the tumor; and (c) applying heat to the site at or near the tumor to express the therapeutic polypeptide, whereby anti-tumor activity is observed.

17 Claims, 21 Drawing Sheets

OTHER PUBLICATIONS

Emtage, et al., *Adenoviral Vectors Expressing Lymphotactin and Interleukin 2 or Lymphotactin and Interleukin 12 Synergize to Facilitate Tumor Regression in Murine Breast Cancer Models*, Human Gene Therapy 10:697-709 (Mar. 20, 1999.)

Fricker, *Heat-inducible promoters for gene therapy*, Molecular Medicine Today 94-95 (Mar. 1997).

Gaber, et al., *Thermosensitive Liposomes: Extravasation and Release of Contents in Tumor Microvascular Networks*, Int. J. Radiation Oncology Biol. Phys. 36, No. 5:1177-1187 (1996).

Gerner, et al., *Heat-inducible vectors for use in gene therapy*, Int. J. Hyperthermia 16, No. 2:171-181 (2000).

Gore, *The Role of Interleukin-2 in Cancer Therapy*, Cancer Bio & Radiopharmaceuticals 11, No. 5:281-283 (1996).

Habib, et al., *A Phase I/II Study of Hepatic Artery Infusion with wtp53-CMV-Ad in Metastatic Malignant Liver Tumors*, Human Gene Therapy 10:2019-2034 (Aug. 10, 1999).

Horiguchi, et al., *Intravesical liposome-mediated interleukin-2 gene therapy in orthotopic murine bladder cancer model*, Gene Therapy 7:844-851 (2000).

Huang, et al., *Heat-induced Gene Expression as a Novel Targeted Cancer Gene Therapy Strategy*, Cancer Research 60:3435-3439 (Jul. 1, 2000).

Kong, et al., *Hyperthermia Enables Tumor-specific Nanoparticle Delivery: Effect of Particle Size*, Cancer Research 60:4440-4445 (Aug. 15, 2000).

Kong, et al., *Characterization of the Effect of Hyperthermia on Nanoparticle Extravasation from Tumor Vasculature*, Cancer Research 61:3027-3032 (Apr. 1, 2001).

Larchian, et al., *Effectiveness of Combined Interleukin 2 and B7.1 Vaccination Strategy is Dependent on the Sequence and Order: A Liposome-mediated Gene Therapy Treatment for Bladder Cancer*, Clinical Cancer Research 6:2913-2920 (Jul. 2000).

Lohr, et al., *Combination Treatment of Murine Tumors by Adenovirus-Mediated local B7/IL12 Immunotherapy and Radiotherapy*, Molecular Therapy 2, No. 3:195-203 (Sep. 2000).

Lohr, et al., *Enhancement of Radiotherapy by Hyperthermia-Regulated Gene Therapy*, Int. J. Radiation Oncology Biol. Phys. 48, No. 5:1513-1518 (2000).

Luna, et al., *Photodynamic Therapy-mediated Oxidative Stress as a Molecular Switch for the Temporal Expression of Genes Ligated to the Human Heat Shock Promoter*, Cancer Research 60:1637-1644 (Mar. 15, 2000).

Luo, et al., *Recombinant bacilli Calmette-Guérin (BCG) expressing human interferon-alpha 2B demonstrates enhanced immunogenicity*, Clin. Exp. Immunol. 123:264-270 (2001).

Majewski, et al., *Interleukin-12 Inhibits Angiogenesis Induced by Human Tumor Cell Lines In Vivo*, The J. of Investigative Dermatology 1114-1118 (1996) (07019901).

Margolin, *Interleukin-2 in the Treatment of Renal Cancer*, Seminars in Oncology 27, No. 2:194-203 (Apr. 2000).

Melero, et al., *IL-12 gene therapy for cancer: in synergy with other immunotherapies*, TRENDS in Immunology 22, No. 3:113-115 (Mar. 2001).

Nasu, et al., *Adenovirus-mediated interleukin-12 gene therapy for prostate cancer: suppression of orthotopic tumor growth and pre-established lung metastases in an orthotopic model*, Gene Therapy 6:338-349 (1999).

Pützer, et al., *Interleukin 12 and B7-1 costimulatory molecule expressed by an adenovirus vector act synergistically to facilitate tumor regression*, Proc. Natl. Acad. Sci. USA 94:10889-10894 (Sep. 1997).

Reynolds, et al., *Mcl-1, a Member of the Bcl-2 Family, Delays Apoptosis Induced by c-Myc Overexpression in Chinese Hamster Ovary Cells*, Cancer Research 54:6348-6352 (Dec. 15, 1994).

Ryffel, *Interleukin-12: Role of Interferon-y in IL-12 Adverse Effects*, Clinical Immunology and Immunopathology 83, No. 1:18-20 (1997).

Siegel et al., *Interleukin-2 Toxicity*, J. of Clinical Onocolgy 9, No. 4:694-704 (Apr. 1991).

Suzuki, et al., *The Human GATA-6 Gene: Structure, Chromosomal Location, and Regulation of Expression by Tissue-Specific and mitogen-Responsive Signals*, Genomics 38:283-290 (1996).

Tanaka, et al., *Downregulation of Fas Ligand by Sheding*, Nature Medicine 4:No. 1:31-36 (Jan. 1998).

Voellmy, et al., *Isolation and functional analysis of a human 70,000-dalton heat shock protein gene segment*, Proc. Natl. Acad. Sci. USA 82:4949-4953 (Aug. 1985).

Voest, et al., *Inhibition of Angiogenesis in Vivo by Interleukin 12*, J. of the Natl Cancer Inst. 87, No. 8:581-586 (Apr. 19, 1995).

Walther, et al., *Cell type specific and inducible promoters for vectors in gene therapy as an approach for cell targeting*, J. Mol. Med. 74:379-392 (1996).

White, et al., *Cell Killing by the Drosophila Gene reaper*, Science 271:805-807 (Feb. 9, 1996).

Yao, et al., *Contribution of Natural Killer Cells to Inhibition of Angiogenesis by Interleukin-12*, Blood 93, No. 5:1612-1621 (Mar. 1, 1999).

Zhang, et al., *Effective Genetic Therapy of Established Medullary Thyroid Carcinomas with Murine Interleukin-2: Dissemination and Cytotoxicity Studis in a Rat Tumor Model*, Endocrinology 140, No. 5:2152-2158 (1999).

\* cited by examiner

SEQUENCE LISTING

<160> NUMBER OF SEQ ID NOS: 13

<210> SEQ ID NO 1
<211> LENGTH: 1265
<212> TYPE: DNA
<213> ORGANISM: Mus musculus
<220> FEATURE:
<221> NAME/KEY: CDS
<222> LOCATION: (127)..(774)

```
<400> SEQUENCE: 1
gcaagagaca cagtcctggg aaagtctgcc ggctatccag acaattataa aaatgtgtct      60
cccaaggtca gcgttccaac agcctcaccc tcggcatcca gcagctcctc tcagtgccgg     120 tccagc atg tgt caa tca cgc tac ctc ctc ttt ttg gcc acc ctt gcc        168
       Met Cys Gln Ser Arg Tyr Leu Leu Phe Leu Ala Thr Leu Ala
         1               5                  10 ctc cta aac cac ctc agt ttg gcc agg gtc att cca gtc tct gga cct       216
Leu Leu Asn His Leu Ser Leu Ala Arg Val Ile Pro Val Ser Gly Pro
 15                  20                  25                  30 gcc agg tgt ctt agc cag tcc cga aac ctg ctg aag acc aca gat gac       264
Ala Arg Cys Leu Ser Gln Ser Arg Asn Leu Leu Lys Thr Thr Asp Asp
                 35                  40                  45 atg gtg aag acg gcc aga gaa aaa ctg aaa cat tat tcc tgc act gct       312
Met Val Lys Thr Ala Arg Glu Lys Leu Lys His Tyr Ser Cys Thr Ala
             50                  55                  60 gaa gac atc gat cat gaa gac atc aca cgg gac caa acc agc aca ttg       360
Glu Asp Ile Asp His Glu Asp Ile Thr Arg Asp Gln Thr Ser Thr Leu
                 65                  70                  75 aag acc tgt tta cca ctg gaa cta cac aag aac gag agt tgc ctg gct       408
Lys Thr Cys Leu Pro Leu Glu Leu His Lys Asn Glu Ser Cys Leu Ala
 80                  85                  90 act aga gag act tct tcc aca aca aga ggg agc tgc ctg ccc cca cag       456
Thr Arg Glu Thr Ser Ser Thr Thr Arg Gly Ser Cys Leu Pro Pro Gln
 95                 100                 105                 110 aag acg tct ttg atg atg acc ctg tgc ctt ggt agc atc tat gag gac       504
Lys Thr Ser Leu Met Met Thr Leu Cys Leu Gly Ser Ile Tyr Glu Asp
                115                 120                 125 ttg aag atg tac cag aca gag ttc cag gcc atc aac gca gca ctt cag       552
Leu Lys Met Tyr Gln Thr Glu Phe Gln Ala Ile Asn Ala Ala Leu Gln
            130                 135                 140 aat cac aac cat cag cag atc att cta gac aag ggc atg ctg gtg gcc       600
Asn His Asn His Gln Gln Ile Ile Leu Asp Lys Gly Met Leu Val Ala
            145                 150                 155 atc gat gag ctg atg cag tct ctg aat cat aat ggc gag act ctg cgc       648
Ile Asp Glu Leu Met Gln Ser Leu Asn His Asn Gly Glu Thr Leu Arg
160                 165                 170 cag aaa cct cct gtg gga gaa gca gac cct tac aga gtg aaa atg aag       696
Gln Lys Pro Pro Val Gly Glu Ala Asp Pro Tyr Arg Val Lys Met Lys
175                 180                 185                 190 ctc tgc atc ctg ctt cac gcc ttc agc acc cgc gtc gtg acc atc aac       744
Leu Cys Ile Leu Leu His Ala Phe Ser Thr Arg Val Val Thr Ile Asn
                195                 200                 205 agg gtg atg ggc tat ctg agc tcc gcc tga aagctcaagg ccctctgcca         794
Arg Val Met Gly Tyr Leu Ser Ser Ala
            210                 215 cagcgccctc ctcacacaga taggaaacaa agaaagattc ataagagtca ggtggtcttg     854
gcctggtggg cttaagctcc ttcaggaatc tgttctccca tcacatctca tctccccaaa     914
ggtggcacag ctacctcagc atggtgccct ccatcgcttc tctcatattc actatacaag     974
ttgtttgtaa gttttcatca aaatattgtt aaggggcgaa gacgtcctcc cctcaatgtg    1034
ttagcagaag agcaagaact gataagctat tgttttgtg ccaaagtgtt tatgaaaaca     1094
ctcagtcacc cctttattaa aaatatttat tgctatattt tatactcatg aaagtacatg    1154
agcctattta tatttattta ttttctattt attataatat ttcttatcag atgaatttga    1214
aacattttga aacatacctt attttgtggt tctaataaag taatgttatc a             1265
```

```
<210> SEQ ID NO 2
<211> LENGTH: 215
<212> TYPE: PRT
<213> ORGANISM: Mus musculus

<400> SEQUENCE: 2

Met Cys Gln Ser Arg Tyr Leu Leu Phe Leu Ala Thr Leu Ala Leu Leu
 1               5                  10                  15

Asn His Leu Ser Leu Ala Arg Val Ile Pro Val Ser Gly Pro Ala Arg
             20                  25                  30

Cys Leu Ser Gln Ser Arg Asn Leu Leu Lys Thr Thr Asp Asp Met Val
         35                  40                  45

Lys Thr Ala Arg Glu Lys Leu Lys His Tyr Ser Cys Thr Ala Glu Asp
 50                  55                  60

Ile Asp His Glu Asp Ile Thr Arg Asp Gln Thr Ser Thr Leu Lys Thr
 65                  70                  75                  80

Cys Leu Pro Leu Glu Leu His Lys Asn Glu Ser Cys Leu Ala Thr Arg
                 85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125

Met Tyr Gln Thr Glu Phe Gln Ala Ile Asn Ala Ala Leu Gln Asn His
    130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190

Ile Leu Leu His Ala Phe Ser Thr Arg Val Val Thr Ile Asn Arg Val
        195                 200                 205

Met Gly Tyr Leu Ser Ser Ala
    210                 215

<210> SEQ ID NO 3
<211> LENGTH: 1840
<212> TYPE: DNA
<213> ORGANISM: Mus musculus
<220> FEATURE:
<221> NAME/KEY: CDS
<222> LOCATION: (35)..(1042)

<400> SEQUENCE: 3
gcacatcaga ccaggcagct cgcagcaaag caag atg tgt cct cag aag cta acc      55
                                     Met Cys Pro Gln Lys Leu Thr
                                      1               5 atc tcc tgg ttt gcc atc gtt ttg ctg gtg tct cca ctc atg gcc atg       103
Ile Ser Trp Phe Ala Ile Val Leu Leu Val Ser Pro Leu Met Ala Met
            10                  15                  20 tgg gag ctg gag aaa gac gtt tat gtt gta gag gtg gac tgg act ccc       151
Trp Glu Leu Glu Lys Asp Val Tyr Val Val Glu Val Asp Trp Thr Pro
        25                  30                  35 gat gcc cct gga gaa aca gtg aac ctc acc tgt gac acg cct gaa gaa       199
Asp Ala Pro Gly Glu Thr Val Asn Leu Thr Cys Asp Thr Pro Glu Glu
 40                  45                  50                  55 gat gac atc acc tgg acc tca gac cag aga cat gga gtc ata ggc tct       247
Asp Asp Ile Thr Trp Thr Ser Asp Gln Arg His Gly Val Ile Gly Ser
                 60                  65                  70
```

-continued

| | |
|---|---|
| gga aag acc ctg acc atc act gtc aaa gag ttt cta gat gct ggc cag<br>Gly Lys Thr Leu Thr Ile Thr Val Lys Glu Phe Leu Asp Ala Gly Gln<br>         75                   80                 85 | 295 |
| tac acc tgc cac aaa gga ggc gag act ctg agc cac tca cat ctg ctg<br>Tyr Thr Cys His Lys Gly Gly Glu Thr Leu Ser His Ser His Leu Leu<br>         90                   95                100 | 343 |
| ctc cac aag aag gaa aat gga att tgg tcc act gaa att tta aaa aat<br>Leu His Lys Lys Glu Asn Gly Ile Trp Ser Thr Glu Ile Leu Lys Asn<br>105                  110                115 | 391 |
| ttc aaa aac aag act ttc ctg aag tgt gaa gca cca aat tac tcc gga<br>Phe Lys Asn Lys Thr Phe Leu Lys Cys Glu Ala Pro Asn Tyr Ser Gly<br>120                  125                130                135 | 439 |
| cgg ttc acg tgc tca tgg ctg gtg caa aga aac atg gac ttg aag ttc<br>Arg Phe Thr Cys Ser Trp Leu Val Gln Arg Asn Met Asp Leu Lys Phe<br>                140                145                150 | 487 |
| aac atc aag agc agt agc agt tcc cct gac tct cgg gca gtg aca tgt<br>Asn Ile Lys Ser Ser Ser Ser Ser Pro Asp Ser Arg Ala Val Thr Cys<br>                155                160                165 | 535 |
| gga atg gcg tct ctg tct gca gag aag gtc aca ctg gac caa agg gac<br>Gly Met Ala Ser Leu Ser Ala Glu Lys Val Thr Leu Asp Gln Arg Asp<br>170                  175                180 | 583 |
| tat gag aag tat tca gtg tcc tgc cag gag gat gtc acc tgc cca act<br>Tyr Glu Lys Tyr Ser Val Ser Cys Gln Glu Asp Val Thr Cys Pro Thr<br>         185                  190                195 | 631 |
| gcc gag gag acc ctg ccc att gaa ctg gcg ttg gaa gca cgg cag cag<br>Ala Glu Glu Thr Leu Pro Ile Glu Leu Ala Leu Glu Ala Arg Gln Gln<br>200                  205                210                215 | 679 |
| aat aaa tat gag aac tac agc acc agc ttc ttc atc agg gac atc atc<br>Asn Lys Tyr Glu Asn Tyr Ser Thr Ser Phe Phe Ile Arg Asp Ile Ile<br>                220                225                230 | 727 |
| aaa cca gac ccg ccc aag aac ttg cag atg aag cct ttg aag aac tca<br>Lys Pro Asp Pro Pro Lys Asn Leu Gln Met Lys Pro Leu Lys Asn Ser<br>235                  240                245 | 775 |
| cag gtg gag gtc agc tgg gag tac cct gac tcc tgg agc act ccc cat<br>Gln Val Glu Val Ser Trp Glu Tyr Pro Asp Ser Trp Ser Thr Pro His<br>         250                  255                260 | 823 |
| tcc tac ttc tcc ctc aag ttc ttt gtt cga atc cag cgc aag aaa gaa<br>Ser Tyr Phe Ser Leu Lys Phe Phe Val Arg Ile Gln Arg Lys Lys Glu<br>265                  270                275 | 871 |
| aag atg aag gag aca gag gag ggg tgt aac cag aaa ggt gcg ttc ctc<br>Lys Met Lys Glu Thr Glu Glu Gly Cys Asn Gln Lys Gly Ala Phe Leu<br>280                  285                290                295 | 919 |
| gta gag aag aca tct acc gaa gtc caa tgc aaa ggc ggg aat gtc tgc<br>Val Glu Lys Thr Ser Thr Glu Val Gln Cys Lys Gly Gly Asn Val Cys<br>                300                305                310 | 967 |
| gtg caa gct cag gat cgc tat tac aat tcc tca tgc agc aag tgg gca<br>Val Gln Ala Gln Asp Arg Tyr Tyr Asn Ser Ser Cys Ser Lys Trp Ala<br>315                  320                325 | 1015 |
| tgt gtt ccc tgc agg gtc cga tcc tag gatgcaacgt tggaaaggaa<br>Cys Val Pro Cys Arg Val Arg Ser<br>         330                  335 | 1062 |
| agaaaagtgg aagacattaa ggaagaaaaa tttaaactca ggatggaaga gtcccccaaa | 1122 |
| agctgtcttc tgcttggttg cttttttcca gttttcctaa gttcatcatg acacctttgc | 1182 |
| tgatttctac atgtaaatgt taaatgcccg cagagccagg gagctaatgt atgcatagat | 1242 |
| attctagcat tccacttggc cttatgctgt tgaatatttt aagtaattta tgtatttatt | 1302 |
| aatttatttc tgcatttcac atttgtatac caagatgtat tgaatatttc atgtgctcgt | 1362 |

-continued

```
ggcctgatcc actgggacca ggccctatta tgcaaattgt gagcttgtta tcttcttcaa    1422
cagctcttca atcagggctg cgtaggtaca ttagcttttg tgacaaccaa taagaacata    1482
atattctgac acaagcagtg ttacatattt gtgaccagta aagacatagg tggtatttgg    1542
agacatgaag aagctgtaaa gttgactctg aagagtttag cactagtttc aacaccaaga    1602 aagactttt agaagtgata ttgataagaa accagggcct tctttagaag ggtacctaaa     1662
tttaaaagaa ttttgaaagg ctgggtatcg gtggtatatg cttttaattc cagcactcag    1722
gagaccaagg caggcagatc tctgtgagtt tgaggacagc ctggtgtaca gagggagttc    1782
cagcacagcc agtgccacac agaaattctg tctcaaaaac aattaaaaaa aaaaaaaa     1840
```

<210> SEQ ID NO 4
<211> LENGTH: 335
<212> TYPE: PRT
<213> ORGANISM: Mus musculus

<400> SEQUENCE: 4

```
Met Cys Pro Gln Lys Leu Thr Ile Ser Trp Phe Ala Ile Val Leu Leu
 1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
```

```
                290            295            300
Cys Lys Gly Gly Asn Val Cys Val Gln Ala Gln Asp Arg Tyr Tyr Asn
305                 310                315                320

Ser Ser Cys Ser Lys Trp Ala Cys Val Pro Cys Arg Val Arg Ser
            325                 330                335

<210> SEQ ID NO 5
<211> LENGTH: 1026
<212> TYPE: DNA
<213> ORGANISM: Homo sapiens
<220> FEATURE:
<221> NAME/KEY: CDS
<222> LOCATION: (170)..(829)

<400> SEQUENCE: 5
gaattcccag aaagcaagag accagagtcc cgggaaagtc ctgccgcgcc tcgggacaat        60
tataaaaatg tggcccccctg ggtcagcctc ccagccaccg ccctcacctg ccgcggccac       120
aggtctgcat ccagcggctc gccctgtgtc cctgcagtgc cggctcagc atg tgt cca       178
                                                     Met Cys Pro
                                                       1 gcg cgc agc ctc ctc ctt gtg gct acc ctg gtc ctg gac cac ctc              226
Ala Arg Ser Leu Leu Leu Val Ala Thr Leu Val Leu Asp His Leu
      5                  10                  15 agt ttg gcc aga aac ctc ccc gtg gcc act cca gac cca gga atg ttc          274
Ser Leu Ala Arg Asn Leu Pro Val Ala Thr Pro Asp Pro Gly Met Phe
 20                  25                  30                  35 cca tgc ctt cac cac tcc caa aac ctg ctg agg gcc gtc agc aac atg          322
Pro Cys Leu His His Ser Gln Asn Leu Leu Arg Ala Val Ser Asn Met
                 40                  45                  50 ctc cag aag gcc aga caa act cta gaa ttt tac cct tgc act tct gaa          370
Leu Gln Lys Ala Arg Gln Thr Leu Glu Phe Tyr Pro Cys Thr Ser Glu
             55                  60                  65 gag att gat cat gaa gat atc aca aaa gat aaa acc agc aca gtg gag          418
Glu Ile Asp His Glu Asp Ile Thr Lys Asp Lys Thr Ser Thr Val Glu
         70                  75                  80 gcc tgt tta cca ttg gaa tta acc aag aat gag agt tgc cta aat tcc          466
Ala Cys Leu Pro Leu Glu Leu Thr Lys Asn Glu Ser Cys Leu Asn Ser
     85                  90                  95 aga gag acc tct ttc ata act aat ggg agt tgc ctg gcc tcc aga aag          514
Arg Glu Thr Ser Phe Ile Thr Asn Gly Ser Cys Leu Ala Ser Arg Lys
100                 105                 110                 115 acc tct ttt atg atg gcc ctg tgc ctt agt agt att tat gaa gac ttg          562
Thr Ser Phe Met Met Ala Leu Cys Leu Ser Ser Ile Tyr Glu Asp Leu
                120                 125                 130 aag atg tac cag gtg gag ttc aag acc atg aat gca aag ctt ctg atg          610
Lys Met Tyr Gln Val Glu Phe Lys Thr Met Asn Ala Lys Leu Leu Met
            135                 140                 145 gat cct aag agg cag atc ttt cta gat caa aac atg ctg gca gtt att          658
Asp Pro Lys Arg Gln Ile Phe Leu Asp Gln Asn Met Leu Ala Val Ile
        150                 155                 160 gat gag ctg atg cag gcc ctg aat ttc aac agt gag act gtg cca caa          706
Asp Glu Leu Met Gln Ala Leu Asn Phe Asn Ser Glu Thr Val Pro Gln
    165                 170                 175 aaa tcc tcc ctt gaa gaa ccg gat ttt tat aaa act aaa atc aag ctc          754
Lys Ser Ser Leu Glu Glu Pro Asp Phe Tyr Lys Thr Lys Ile Lys Leu
180                 185                 190                 195 tgc ata ctt ctt cat gct ttc aga att cgg gca gtg act att gac aga          802
Cys Ile Leu Leu His Ala Phe Arg Ile Arg Ala Val Thr Ile Asp Arg
                200                 205                 210
```

```
gtg acg agc tat ctg aat gct tcc taa aaagcgaggt ccctccaaac          849
Val Thr Ser Tyr Leu Asn Ala Ser
                215 cgttgtcatt tttataaaac tttgaaatga ggaaactttg ataggatgtg gattaagaac   909 tagggagggg gaaagaagga tgggactatt acatccacat gatacctctg atcaagtatt   969 tttgacattt actgtggata aattgttttt aagttttcat gaatgaattg ctaagaa      1026
```

<210> SEQ ID NO 6
<211> LENGTH: 219
<212> TYPE: PRT
<213> ORGANISM: Homo sapiens

<400> SEQUENCE: 6

```
Met Cys Pro Ala Arg Ser Leu Leu Val Ala Thr Leu Val Leu Leu
1               5                   10                  15

Asp His Leu Ser Leu Ala Arg Asn Leu Pro Val Ala Thr Pro Asp Pro
                20                  25                  30

Gly Met Phe Pro Cys Leu His His Ser Gln Asn Leu Leu Arg Ala Val
            35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
                100                 105                 110

Ser Arg Lys Thr Ser Phe Met Met Ala Leu Cys Leu Ser Ser Ile Tyr
            115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
                180                 185                 190

Ile Lys Leu Cys Ile Leu Leu His Ala Phe Arg Ile Arg Ala Val Thr
            195                 200                 205

Ile Asp Arg Val Thr Ser Tyr Leu Asn Ala Ser
    210                 215
```

<210> SEQ ID NO 7
<211> LENGTH: 2318
<212> TYPE: DNA
<213> ORGANISM: Homo sapiens
<220> FEATURE:
<221> NAME/KEY: CDS
<222> LOCATION: (14)..(1000)

<400> SEQUENCE: 7

```
ggcccagagc aag atg tgt cac cag cag ttg gtc atc tct tgg ttt tcc    49
            Met Cys His Gln Gln Leu Val Ile Ser Trp Phe Ser
            1               5                   10 ctg gtt ttt ctg gca tct ccc ctc gtg gcc ata tgg gaa ctg aag aaa   97
Leu Val Phe Leu Ala Ser Pro Leu Val Ala Ile Trp Glu Leu Lys Lys
        15                  20                  25
```

```
gat gtt tat gtc gta gaa ttg gat tgg tat ccg gat gcc cct gga gaa    145
Asp Val Tyr Val Val Glu Leu Asp Trp Tyr Pro Asp Ala Pro Gly Glu
    30              35              40 atg gtg gtc ctc acc tgt gac acc cct gaa gaa gat ggt atc acc tgg    193
Met Val Val Leu Thr Cys Asp Thr Pro Glu Glu Asp Gly Ile Thr Trp
45              50              55              60 acc ttg gac cag agc agt gag gtc tta ggc tct ggc aaa acc ctg acc    241
Thr Leu Asp Gln Ser Ser Glu Val Leu Gly Ser Gly Lys Thr Leu Thr
                65              70              75 atc caa gtc aaa gag ttt gga gat gct ggc cag tac acc tgt cac aaa    289
Ile Gln Val Lys Glu Phe Gly Asp Ala Gly Gln Tyr Thr Cys His Lys
                80              85              90 gga ggc gag gtt cta agc cat tcg ctc ctg ctg ctt cac aaa aag gaa    337
Gly Gly Glu Val Leu Ser His Ser Leu Leu Leu Leu His Lys Lys Glu
            95              100             105 gat gga att tgg tcc act gat att tta aag gac cag aaa gaa ccc aaa    385
Asp Gly Ile Trp Ser Thr Asp Ile Leu Lys Asp Gln Lys Glu Pro Lys
        110             115             120 aat aag acc ttt cta aga tgc gag gcc aag aat tat tct gga cgt ttc    433
Asn Lys Thr Phe Leu Arg Cys Glu Ala Lys Asn Tyr Ser Gly Arg Phe
125             130             135             140 acc tgc tgg tgg ctg acg aca atc agt act gat ttg aca ttc agt gtc    481
Thr Cys Trp Trp Leu Thr Thr Ile Ser Thr Asp Leu Thr Phe Ser Val
                145             150             155 aaa agc agc aga ggc tct tct gac ccc caa ggg gtg acg tgc gga gct    529
Lys Ser Ser Arg Gly Ser Ser Asp Pro Gln Gly Val Thr Cys Gly Ala
                160             165             170 gct aca ctc tct gca gag aga gtc aga ggg gac aac aag gag tat gag    577
Ala Thr Leu Ser Ala Glu Arg Val Arg Gly Asp Asn Lys Glu Tyr Glu
            175             180             185 tac tca gtg gag tgc cag gag gac agt gcc tgc cca gct gct gag gag    625
Tyr Ser Val Glu Cys Gln Glu Asp Ser Ala Cys Pro Ala Ala Glu Glu
        190             195             200 agt ctg ccc att gag gtc atg gtg gat gcc gtt cac aag ctc aag tat    673
Ser Leu Pro Ile Glu Val Met Val Asp Ala Val His Lys Leu Lys Tyr
205             210             215             220 gaa aac tac acc agc agc ttc ttc atc agg gac atc atc aaa cct gac    721
Glu Asn Tyr Thr Ser Ser Phe Phe Ile Arg Asp Ile Ile Lys Pro Asp
                225             230             235 cca ccc aac aac ttg cag ctg aag cca tta aag aat tct cgg cag gtg    769
Pro Pro Asn Asn Leu Gln Leu Lys Pro Leu Lys Asn Ser Arg Gln Val
                240             245             250 gag gtc agc tgg gag tac cct gac acc tgg agt act cca cat tcc tac    817
Glu Val Ser Trp Glu Tyr Pro Asp Thr Trp Ser Thr Pro His Ser Tyr
            255             260             265 ttc tcc ctg aca ttc tgc gtt cag gtc cag ggc aag agc aag aga gaa    865
Phe Ser Leu Thr Phe Cys Val Gln Val Gln Gly Lys Ser Lys Arg Glu
        270             275             280 aag aaa gat aga gtc ttc acc gac aag acc tca gcc acg gtc atc tgc    913
Lys Lys Asp Arg Val Phe Thr Asp Lys Thr Ser Ala Thr Val Ile Cys
285             290             295             300 cgc aaa aat gcc agc att agc gtg cgg gcc cag gac cgc tac tat agc    961
Arg Lys Asn Ala Ser Ile Ser Val Arg Ala Gln Asp Arg Tyr Tyr Ser
                305             310             315 tca tct tgg agc gaa tgg gca tct gtg ccc tgc agt tag gttctgatcc    1010
Ser Ser Trp Ser Glu Trp Ala Ser Val Pro Cys Ser
                320             325 aggatgaaaa tttggaggaa aagtggaaga tattaagcaa aatgtttaaa gacacaacgg  1070
aatagaccca aaaagataat ttctatctga tttgctttaa aacgtttttt taggatcaca  1130
```

```
atgatatctt tgctgtatttt gtatagttcg atgctaaatg ctcattgaaa caatcagcta   1190
atttatgtat agattttcca gctctcaagt tgccatgggc cttcatgcta tttaaatatt   1250
taagtaattt atgtatttat tagtatatta ctgttattta acgtttgtct gccaggatgt   1310
atggaatgtt tcatactctt atgacctgat ccatcaggat cagtccctat tatgcaaaat   1370
gtgaatttaa ttttatttgt actgacaact tttcaagcaa ggctgcaagt acatcagttt   1430
tatgacaatc aggaagaatg cagtgttctg ataccagtgc catcatacac ttgtgatgga   1490
tgggaacgca agatacttt acatggaaac ctgacaatgc aaacctgttg agaagatcca   1550
ggagaacaag atgctagttc ccatgtctgt gaagacttcc tggagatggt gttgataaag   1610
caatttaggg ccacttacac ttctaagcaa gtttaatctt tggatgcctg aattttaaaa   1670
gggctagaaa aaaatgattg accagcctgg gaaacataac aagaccccgt ctctacaaaa   1730
aaaatttaaa attagccagg cgtggtggct catgcttgtg gtcccagctg ttcaggagga   1790
tgaggcagga ggatctcttg agcccaggag gtcaaggcta tggtgagccg tgattgtgcc   1850
actgcatacc agcctaggtg acagaatgag accctgtctc aaaaaaaaaa atgattgaaa   1910
ttaaaattca gctttagctt ccatggcagt cctcaccccc acctctctaa aagacacagg   1970
aggatgacac agaaacaccg taagtgtctg gaaggcaaaa agatcttaag attcaagaga   2030
gaggacaagt agttatggct aaggacatga aattgtcaga atggcaggtg gcttcttaac   2090
agccatgtga gaagcagaca gatgcaaaga aaatctggaa tcccttctc attagcatga   2150 atgaacctga tacacaatta tgaccagaaa atatggctcc atgaaggtgc acttttaag   2210 taatgtatgt gcgctctgta aagtgattac atttgttttcc tgtttgttta tttatttatt   2270 tattttttgca ttctgaggct gaactaataa aaactcttct ttgtaatc                2318
```

<210> SEQ ID NO 8
<211> LENGTH: 328
<212> TYPE: PRT
<213> ORGANISM: Homo sapiens

<400> SEQUENCE: 8

```
Met Cys His Gln Gln Leu Val Ile Ser Trp Phe Ser Leu Val Phe Leu
 1               5                  10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
        50                  55                  60

Ser Ser Glu Val Leu Gly Ser Gly Lys Thr Leu Thr Ile Gln Val Lys
 65                 70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160
```

```
Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Ser Leu Pro Ile
        195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Asn Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 9
<211> LENGTH: 939
<212> TYPE: DNA
<213> ORGANISM: Mus musculus
<220> FEATURE:
<221> NAME/KEY: CDS
<222> LOCATION: (48)..(557)

<400> SEQUENCE: 9
atcacccttg ctaatcactc ctcacagtga cctcaagtcc tgcaggc atg tac agc       56
                                                   Met Tyr Ser
                                                     1 atg cag ctc gca tcc tgt gtc aca ttg aca ctt gtg ctc ctt gtc aac     104
Met Gln Leu Ala Ser Cys Val Thr Leu Thr Leu Val Leu Leu Val Asn
  5                  10                  15 agc gca ccc act tca agc tcc act tca agc tct aca gcg gaa gca cag     152
Ser Ala Pro Thr Ser Ser Ser Thr Ser Ser Ser Thr Ala Glu Ala Gln
 20                  25                  30                  35 cag cag cag cag cag cag cag cag cag cag cac ctg gag cag ctg         200
Gln Gln Gln Gln Gln Gln Gln Gln Gln Gln His Leu Glu Gln Leu
                 40                  45                  50 ttg atg gac cta cag gag ctc ctg agc agg atg gag aat tac agg aac     248
Leu Met Asp Leu Gln Glu Leu Leu Ser Arg Met Glu Asn Tyr Arg Asn
             55                  60                  65 ctg aaa ctc ccc agg atg ctc acc ttc aaa ttt tac ttg ccc aag cag     296
Leu Lys Leu Pro Arg Met Leu Thr Phe Lys Phe Tyr Leu Pro Lys Gln
         70                  75                  80 gcc aca gaa ttg aaa gat ctt cag tgc cta gaa gat gaa ctt gga cct     344
Ala Thr Glu Leu Lys Asp Leu Gln Cys Leu Glu Asp Glu Leu Gly Pro
 85                  90                  95 ctg cgg cat gtt ctg gat ttg act caa agc aaa agc ttt caa ttg gaa     392
Leu Arg His Val Leu Asp Leu Thr Gln Ser Lys Ser Phe Gln Leu Glu
100                 105                 110                 115 gat gct gag aat ttc atc agc aat atc aga gta act gtt gta aaa cta     440
Asp Ala Glu Asn Phe Ile Ser Asn Ile Arg Val Thr Val Val Lys Leu
                 120                 125                 130
```

```
aag ggc tct gac aac aca ttt gag tgc caa ttc gat gat gag tca gca     488
Lys Gly Ser Asp Asn Thr Phe Glu Cys Gln Phe Asp Asp Glu Ser Ala
            135                 140                 145 act gtg gtg gac ttt ctg agg aga tgg ata gcc ttc tgt caa agc atc     536
Thr Val Val Asp Phe Leu Arg Arg Trp Ile Ala Phe Cys Gln Ser Ile
    150                 155                 160 atc tca aca agc cct caa taa ctatgtacct cctgcttaca acacataagg        587
Ile Ser Thr Ser Pro Gln
        165 ctctctattt atttaaatat ttaactttaa tttatttttg gatgtattgt ttactatctt   647 ttgtaactac tagtcttcag atgataaata tggatcttta aagattcttt ttgtaagccc   707 caagggctca aaatgttttt aaactattta tctgaaatta tttattatat tgaattgtta   767 aatatcatgt gtaggtagac tcattaataa aagtatttag atgattcaaa tataaataag   827 ctcagatgtc tgtcattttt aggacagcac aaagtaagcg ctaaaataac ttctcagtta   887 ttcctgtgaa ctctatgtta atcagtgttt tcaagaaata aagctctcct ct           939

<210> SEQ ID NO 10
<211> LENGTH: 169
<212> TYPE: PRT
<213> ORGANISM: Mus musculus

<400> SEQUENCE: 10

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln
                165

<210> SEQ ID NO 11
<211> LENGTH: 844
<212> TYPE: DNA
<213> ORGANISM: Homo sapiens
<220> FEATURE:
<221> NAME/KEY: CDS
<222> LOCATION: (180)..(569)

<400> SEQUENCE: 11
ccccataata ttttccaga attaacagta taaattgcat ctcttgttca agagttccct    60
```

-continued

```
atcactctct ttaatcacta ctcacagtaa cctcaactcc tgccacaatg tacaggatgc      120
aactcctgtc ttgcattgca ctaagtcttg cacttgtcac aaacagtgca cctacttca      179 agt tct aca aag aaa aca cag cta caa ctg gag cat tta ctg ctg gat       227
Ser Ser Thr Lys Lys Thr Gln Leu Gln Leu Glu His Leu Leu Leu Asp
1               5                  10                  15 tta cag atg att ttg aat gga att aat aat tac aag aat ccc aaa ctc       275
Leu Gln Met Ile Leu Asn Gly Ile Asn Asn Tyr Lys Asn Pro Lys Leu
            20                  25                  30 acc agg atg ctc aca ttt aag ttt tac atg ccc aag aag gcc aca gaa       323
Thr Arg Met Leu Thr Phe Lys Phe Tyr Met Pro Lys Lys Ala Thr Glu
        35                  40                  45 ctg aaa cat ctt cag tgt cta gaa gaa gaa ctc aaa cct ctg gag gaa       371
Leu Lys His Leu Gln Cys Leu Glu Glu Glu Leu Lys Pro Leu Glu Glu
    50                  55                  60 gtg cta aat tta gct caa agc aaa aac ttt cac tta aga ccc agg gac       419
Val Leu Asn Leu Ala Gln Ser Lys Asn Phe His Leu Arg Pro Arg Asp
65                  70                  75                  80 tta atc agc aat atc aac gta ata gtt ctg gaa cta aag gga tct gaa       467
Leu Ile Ser Asn Ile Asn Val Ile Val Leu Glu Leu Lys Gly Ser Glu
                85                  90                  95 aca aca ttc atg tgt gaa tat gct gat gag aca gca acc att gta gaa       515
Thr Thr Phe Met Cys Glu Tyr Ala Asp Glu Thr Ala Thr Ile Val Glu
            100                 105                 110 ttt ctg aac aga tgg att acc ttt tgt caa agc atc atc tca aca ctg       563
Phe Leu Asn Arg Trp Ile Thr Phe Cys Gln Ser Ile Ile Ser Thr Leu
        115                 120                 125 act tga taattaagtg cttcccactt aaaacatatc aggccttcta tttatttaaa        619
Thr tatttaaatt ttatatttat tgttgaatgt atggtttgct acctattgta actattattc     679
ttaatcttaa aactataaat atggatcttt tatgattctt tttgtaagcc ctaggggctc     739
taaaatggtt tcacttattt atcccaaaat atttattatt atgttgaatg ttaaatatag     799
tatctatgta gattggttag taaaactatt taataaattt gataa                    844
```

<210> SEQ ID NO 12
<211> LENGTH: 129
<212> TYPE: PRT
<213> ORGANISM: Homo sapiens

<400> SEQUENCE: 12

```
Ser Ser Thr Lys Lys Thr Gln Leu Gln Leu Glu His Leu Leu Leu Asp
1               5                  10                  15

Leu Gln Met Ile Leu Asn Gly Ile Asn Asn Tyr Lys Asn Pro Lys Leu
            20                  25                  30

Thr Arg Met Leu Thr Phe Lys Phe Tyr Met Pro Lys Lys Ala Thr Glu
        35                  40                  45

Leu Lys His Leu Gln Cys Leu Glu Glu Glu Leu Lys Pro Leu Glu Glu
    50                  55                  60

Val Leu Asn Leu Ala Gln Ser Lys Asn Phe His Leu Arg Pro Arg Asp
65                  70                  75                  80

Leu Ile Ser Asn Ile Asn Val Ile Val Leu Glu Leu Lys Gly Ser Glu
                85                  90                  95

Thr Thr Phe Met Cys Glu Tyr Ala Asp Glu Thr Ala Thr Ile Val Glu
            100                 105                 110

Phe Leu Asn Arg Trp Ile Thr Phe Cys Gln Ser Ile Ile Ser Thr Leu
        115                 120                 125
```

-continued

Thr

<210> SEQ ID NO 13
<211> LENGTH: 592
<212> TYPE: DNA
<213> ORGANISM: Homo sapiens

<400> SEQUENCE: 13

```
gcgtgaagag ctgcagtgtc actcttaaag ctgaattaat ctctgccatt ccttaaggaa      60
acaggcaact gtcttaaaac cgtggtttgg aaaatatttt gttcaagata aaactgtttt     120
aagatatatg tatatatatc ttatatatct gtattcgcat ggtaacatat cttcggtctt     180
cctgccgctg ggctctcagc ggccctccaa ggcagcccgc aggcccgtgc tcgcctcagg     240
gatcctccac agccccgggg agaccttgcc tctaaagttg ctgcttttgc agctctgcca     300
caaccgcgcg tcctcagagc cagccgggag gagctagaac cttccccgcg tttctttcag     360
cagccctgag tcagaggcgg gctggccttg caagtagccg cccagccttc ttcggtctca     420
cggaccgatc cgcccgaacc ttctcccggg gtcagcgccg cgctgcgccg cccggctgac     480
tcagcccggg cgggcgggcg ggaggctctc gactgggcgg gaaggtgcgg gaaggttcgc     540
ggcggcgggg tcggggaggt gcaaaaggat gaaaagcccg tggacggagc tg             592
```

METHOD FOR SELECTIVE EXPRESSION OF THERAPEUTIC GENES BY HYPERTHERMIA

RELATED APPLICATION INFORMATION

This application is based on and claims priority to U.S. Provisional Patent Application Ser. No. 60/298,305, filed Jun. 14, 2001, the entire contents of which are herein incorporated by reference.

GRANT STATEMENT

This work was supported by grant CA81512 from the U.S. National Cancer Institute to Dr. Chuan-Yuan Li, and grants CA40355 and CA42745 from the U.S. National Cancer Institute to Dr. Mark W. Dewhirst. Thus, the U.S. government has certain rights in the invention.

FIELD OF THE INVENTION

The present invention generally relates to control of gene expression in tumor cells. Specifically, the present invention provides methods for using a heat inducible promoter operatively linked to a therapeutic gene to preferably induce both immune and anti-angiogenic responses in vivo.

Table of Abbreviations

| | |
|---|---|
| 4TI cells | mouse mammary cancer cells |
| AdCMVIL12 | Adenoviral vector encoding IL12 under the control of a CMV promoter (AdmIL12) |
| AdGFP | Adenoviral vector encoding GFP under the control of a CMV promoter |
| AdhspEGFP | Adenoviral vector encoding EGFP under the control of a hsp70B promoter |
| AdhspIL12 | Adenoviral vector encoding IL12 under the control of a hsp70B promoter |
| AdhspTNFα | Adenoviral vector encoding TNF-α under the control of a hsp70B promoter |
| AdmIL12 | Adenoviral vector encoding murine IL12 under the control of a CMV promoter (AdCMVIL12) |
| AdIL12/B7.1 | Adenoviral vector encoding murine IL12 and B7.1 co-stimulatory molecule |
| AdmIL2 | Adenoviral vector encoding murine IL2 under the control of a CMV promoter |
| B16.F10 cells | murine melanoma cells |
| B7.1 | B lymphocyte activation antigen 7.1 |
| Balb/c | non-immunogenic mouse strain |
| β-gal | β-galactosidase |
| BSA | bovine serum albumin |
| C57BL/6 | non-immunogenic mouse strain |
| CEA | carcinoembryonic antigen |
| CMV | cytomegalovirus |
| EGFP | enhanced green fluorescent protein |
| EGR-1 | early growth response protein 1 |
| FACS | fluorescence-activated cell sorting |
| FACScan | fluorescence-activated cell sorter |
| FACStar | fluorescence-activated cell sorter |
| FITC | fluorescein isothiocyanate |
| GFP | green fluorescent protein |
| hsp70 | heat shock protein 70 |
| hsp70B | heat shock protein 70B |
| IFN-α | interferon gamma |
| IFN-γ | interferon gamma |
| IL12 | interleukin 12 |
| IL2 | interleukin 2 |
| IL4 | interleukin 4 |
| IL6 | interleukin 6 |
| IRES | internal ribosome entry site |
| LAK | lymphokine activated killer cells |
| MHC I | major histocompatability complex class I |

-continued

Table of Abbreviations

| | |
|---|---|
| mIL12 | murine IL12 |
| mIL2 | murine IL2 |
| MOI | multiplicity of infection |
| NGVL | National Gene Vector Laboratory |
| NK | natural killer cells |
| nu/nu | homozygous nude mice |
| PBS | phosphate-buffered saline |
| PEG | polyethylene glycol |
| Rho | rhodamine |
| Rho-PE | rhodamine-labeled phosphoethanolamine |
| $RTIA_{60}$ | relative tumor interstitial amount at 60 minutes |
| SKOV-3 | p53 null ovarian cancer cells |
| pfu | plaque-forming unit |
| Th1 | CD4+ T helper cells |
| TNF-α | tumor necrosis factor alpha |
| YAC-1 cells | tumor cells |

BACKGROUND ART

A substantial number of cancers fail to respond to conventional radiation and chemotherapy, and thus there exists a clear need for alternative non-surgical strategies. Development of gene therapy techniques is approaching clinical realization for the treatment of neoplastic and metabolic diseases, and numerous genes displaying anti-tumor activity have been identified. However, the usefulness of gene therapy methods has been limited due to systemic toxicity of anti-tumor polypeptides encoded by gene therapy constructs (Spriggs & Yates (1992) in Bentler, ed., *Tumor Necrosis Factor: The Molecules and Their Emerging Roles in Medicine*, pp. 383–406 Raven Press, New York, N.Y.; Sigel & Puri (1991) *J Clin Oncol* 9:694–704; Ryffel (1997) *Immunopathol* 83:18–20). A versatile mechanism for controllable gene expression is therefore highly desired for gene therapy.

A mechanism for controlling gene expression should ideally include both spatial and temporal control of gene expression. One existing strategy employs a chemically regulated signal, for example the tetracycline-inducible gene expression system (Gossen & Bujard (1992) *Proc Natl Acad Sci USA* 89:5547–5551; Gossen & Bujard (1993) *Nuc Acids Res* 21(18):4411–4412; Gossen et al. (1995) *Science* 268: 1766–1769). A similar approach involves the provision of ionizing radiation to activate a radiosensitive promoter, e.g. the EGR-1 promoter (Weischelbaum et al. (1994) *Cancer Res* 54:4266–4269; Hallahan et al. (1995) *Nat Med* 1(8): 786–791; Joki et al. (1995) *Hum Gen Ther* 6:1507–1513). An alternative design relies on endogenous control of gene expression. For example, the CEA promoter is selectively expressed in cancer cells (Hauck & Stanners (1995) *J Biol Chem* 270:3602; Richards et al. (1995) *Human Gene Ther* 6:881–893). Although each of the afore-mentioned systems display inducibility, a lack of temporal and spatial precision of gene induction, an ineffective magnitude of gene induction, a background level of non-induced gene expression, or an inability to regulate termination of gene expression, can still prohibit their usefulness.

Thus, there remains substantial need for improvement of gene therapy methods, particularly with regards to the design of gene therapy constructs adapted for inducible expression and to the development of vector systems for delivery of a therapeutic transgene to target tissues.

To meet this need, the present invention discloses a gene therapy construct comprising a heat-inducible promoter operatively linked to a nucleic acid molecule encoding a polypeptide that can induce immunological and/or anti-angiogenic activity. When employed according to the methods of the present invention, the disclosed gene therapy construct provides precise temporally- and spatially-regulated expression of a therapeutic gene that can promote tumor regression.

SUMMARY OF INVENTION

The present invention discloses a method for promoting anti-tumor activity in a mammal. The method comprises: (a) providing a construct comprising a polynucleotide encoding a therapeutic polypeptide, wherein the polynucleotide is operatively linked to a heat-inducible promoter; (b) administering the construct to a mammal at a site at or near the tumor; and (c) applying heat to the site to express the therapeutic polypeptide, whereby anti-tumor activity is observed. Preferred embodiments of the construct comprise an adenoviral vector, an adeno-viral associated vector, a liposome, or a plasmid.

The polynucleotide employed in the method can encode a polypeptide having an ability to elicit an immunostimulatory response, an anti-angiogenic response, an anti-proliferative response, a cell suicide response, or combinations thereof. In a preferred embodiment, the polynucleotide encodes a polypeptide having an ability to elicit both an immunostimulatory response and an anti-angiogenic response.

In a preferred embodiment, the polynucleotide employed by the disclosed method encodes a functional interleukin 12 (IL12) polypeptide. Preferably, the functional IL12 polypeptide comprises a first subunit and a second subunit. The first subunit can comprise: (a) a polypeptide encoded by a nucleic acid molecule of SEQ ID NO:1 or 5; (b) a polypeptide encoded by a nucleic acid substantially identical to SEQ ID NO:1 or 5; (c) a polypeptide having an amino acid sequence set forth as SEQ ID NO:2 or 6; (d) a polypeptide having an amino acid sequence substantially identical to SEQ ID NO:2 or 6; or (e) a polypeptide that is a biological equivalent of SEQ ID NO:2 or 6. The second subunit can comprise: (a) a polypeptide encoded by a nucleic acid molecule of SEQ ID NO:3 or 7; (b) a polypeptide encoded by a nucleic acid substantially identical to SEQ ID NO:3 or 7; (c) a polypeptide having an amino acid sequence set forth as SEQ ID NO:4 or 8; (d) a polypeptide having an amino acid sequence substantially identical to SEQ ID NO:4 or 8; or (e) a polypeptide that is a biological equivalent of SEQ ID NO:4 or 8. Preferably, the polynucleotide encoding an IL12 polypeptide comprises: (a) a nucleotide sequence set forth as SEQ ID NO:1, 3, 5, or 7; or (b) a nucleotide sequence that is substantially identical to SEQ ID NO:1, 3, 5, or 7.

In another preferred embodiment, the polynucleotide employed by the methods of the present invention comprises a functional interleukin 2 (IL2) polynucleotide. Preferably, the IL2 polypeptide comprises: (a) a polypeptide encoded by a nucleic acid molecule of SEQ ID NO:9 or 11; (b) a polypeptide encoded by a nucleic acid substantially identical to SEQ ID NO:9 or 11; (c) a polypeptide having an amino acid sequence set forth as SEQ ID NO:10 or 12; (d) a polypeptide having an amino acid sequence substantially identical to SEQ ID NO:10 or 12; or (e) a polypeptide that is a biological equivalent of SEQ ID NO:10 or 12. Preferably, the polynucleotide encoding an IL2 polypeptide comprises: (a) a nucleotide sequence set forth as SEQ ID NO:9 or 11; or (b) a nucleotide sequence that is substantially identical to SEQ ID NO:9 or 11.

In a preferred embodiment, the heat-inducible promoter comprises an hsp70 promoter. The hsp70 promoter can comprise a human hsp70B promoter. Preferably, the human hsp70B promoter comprises: (a) the nucleotide sequence set forth as SEQ ID NO:13, or functional portion thereof; or (b) a nucleotide sequence substantially identical to SEQ ID NO:13.

In one embodiment, administering the construct comprises intratumoral injection of the construct.

In another embodiment, administration of the vector can comprise intravenous injection in combination with heat-facilitated extravasation at a tumor site. Preferably, the pre-heating of the tumor is performed about 0–4 hours prior to administering the construct, more preferably about 0–2 hours prior to administering the construct. Preferably, pre-heating comprises an increase in the temperature of the tumor to about 40° C.–42° C., more preferably about 42° C. In this case, the tumor is also heat-treated following administration of the construct to induce expression of the therapeutic nucleic acid.

In a preferred embodiment, applying heat to express the therapeutic polypeptide comprises an increase in temperature at the site in need of treatment to about 39° C.–43° C., or more preferably about 42° C.–43° C.

In a preferred embodiment, the anti-tumor activity is characterized by an immune response and an anti-angiogenic response. In another preferred embodiment, the method for promoting anti-tumor activity can further comprise providing radiotherapy at the site at or near the tumor, whereby anti-tumor activity is enhanced when compared to anti-tumor activity observed in response to radiotherapy alone.

The present invention also provides a method for treating a disorder or condition in a mammal using a heat-inducible IL12 gene therapy construct. The method comprises: (a) providing a construct comprising a polynucleotide encoding a polypeptide encoding a functional IL12 polypeptide, wherein the polynucleotide is operatively linked to a heat-inducible promoter; (b) administering the construct to a mammal at or near a site in need of treatment; and (c) applying heat to the site to express the polypeptide, whereby the disorder is treated. Preferably, the disorder or condition to be treated is a proliferative or angiogenic disorder or condition.

Preferred constructs comprise an adenoviral vector, an adeno-viral associated vector, a liposome, or a plasmid.

Preferably, the functional IL12 polypeptide comprises a first subunit and a second subunit. The first subunit can comprise: (a) a polypeptide encoded by a nucleic acid molecule of SEQ ID NO:1 or 5; (b) a polypeptide encoded by a nucleic acid substantially identical to SEQ ID NO:1 or 5; (c) a polypeptide having an amino acid sequence set forth as SEQ ID NO:2 or 6; (d) a polypeptide having an amino acid sequence substantially identical to SEQ ID NO:2 or 6; or (e) a polypeptide that is a biological equivalent of SEQ ID NO:2 or 6. The second subunit can comprise: (a) a polypeptide encoded by a nucleic acid molecule of SEQ ID NO:3 or 7; (b) a polypeptide encoded by a nucleic acid substantially identical to SEQ ID NO:3 or 7; (c) a polypeptide having an amino acid sequence set forth as SEQ ID NO:4 or 8; (d) a polypeptide having an amino acid sequence substantially identical to SEQ ID NO:4 or 8; or (e) a polypeptide that is a biological equivalent of SEQ ID NO:4 or 8. Preferably, the polynucleotide encoding an IL12 polypeptide comprises: (a) a nucleotide sequence set forth as SEQ ID NO:1, 3, 5, or 7; or (b) a nucleotide sequence that is substantially identical to SEQ ID NO:1, 3,5, or 7.

In a preferred embodiment, the heat-inducible promoter comprises an hsp70 promoter. The hsp70 promoter can comprise a human hsp70B promoter. Preferably, the human hsp70B promoter comprises: (a) the nucleotide sequence set forth as SEQ ID NO:13; or (b) a nucleotide sequence substantially identical to SEQ ID NO:13.

In a preferred embodiment, applying heat to express the therapeutic polypeptide comprises an increase in temperature at the site in need of treatment to about 39° C.–43° C., or more preferably about 42° C.–43° C.

In one embodiment, the site in need of treatment is a tumor. Preferably, the anti-tumor activity comprises tumor regression. More preferably, the tumor regression is characterized by an immune response and an anti-angiogenic response.

In one embodiment, administering the construct comprises intratumoral injection of the construct.

In another embodiment, administration of the vector can comprise intravenous injection in combination with heat-facilitated extravasation at a tumor site. Preferably, the pre-heating of the tumor is performed about 0–4 hours prior to administering the construct, more preferably about 0–2 hours prior to administering the construct. Preferably, the pre-heating comprises an increase in temperature of the tumor to about 40° C.–42° C., or more preferably about 42° C. In this case, the tumor is also heat-treated following administration of the construct to induce expression of the therapeutic nucleic acid.

In another preferred embodiment, the disclosed method for promoting anti-tumor activity further comprises providing radiotherapy at the site at or near the tumor, whereby anti-tumor activity is enhanced when compared to anti-tumor activity observed in response to radiotherapy alone.

The present invention also provides a method for treating a disorder or condition in a mammal using an IL2 gene therapy construct. The method comprises: (a) providing a construct comprising a polynucleotide encoding a polypeptide encoding a functional IL2 polypeptide, wherein the polynucleotide is operatively linked to a heat-inducible promoter; (b) administering the construct to a mammal at or near a site in need of treatment; and (c) applying heat to the site to express the polypeptide whereby the disorder is treated. Preferably, the disorder or condition to be treated is a proliferative or angiogenic disorder or condition.

Preferred constructs comprise an adenoviral vector, an adeno-viral associated vector, a liposome, or a plasmid.

Preferably, the functional IL2 polypeptide employed in the method comprises: (a) a polypeptide encoded by a nucleic acid molecule of SEQ ID NO:9 or 11; (b) a polypeptide encoded by a nucleic acid substantially identical to SEQ ID NO:9 or 11; (c) a polypeptide having an amino acid sequence set forth as SEQ ID NO:10 or 12; (d) a polypeptide having an amino acid sequence substantially identical to SEQ ID NO:10 or 12; or (e) a polypeptide that is a biological equivalent of SEQ ID NO:10 or 12. Preferably, the polynucleotide encoding the functional IL2 polypeptide comprises: (a) a nucleotide sequence set forth as SEQ ID NO:9 or 11; or (b) a nucleotide sequence that is substantially identical to SEQ ID NO:9 or 11.

In a preferred embodiment, the heat-inducible promoter comprises an hsp70 promoter. The hsp70 promoter can comprise a human hsp70B promoter. Preferably, the human hsp70B promoter comprises: (a) the nucleotide sequence set forth as SEQ ID NO:13, or functional portion thereof; or (b) a nucleotide sequence substantially identical to SEQ ID NO:13.

In a preferred embodiment, applying heat to express the therapeutic polypeptide comprises an increase in temperature at the site in need of treatment to about 39° C.–43° C., or more preferably about 42° C.–43° C.

In one embodiment, the site in need of treatment is a tumor. Preferably, the anti-tumor activity comprises tumor regression. More preferably, the tumor regression is characterized by an immune response and an anti-angiogenic response.

In one embodiment, administering the construct comprises intratumoral injection of the construct.

In another embodiment, administration of the vector can comprise intravenous injection in combination with heat-facilitated extravasation at a tumor site. Preferably, the pre-heating of the tumor is performed about 0–4 hours prior to administering the construct, more preferably about 0–2 hours prior to administering the construct. Preferably, pre-heating comprises an increase in temperature of the tumor to about 40° C.–42° C., or more preferably about 42° C. In this case, the tumor is also heat-treated following administration of the construct to induce expression of the therapeutic nucleic acid.

In another preferred embodiment, the disclosed methods for promoting anti-tumor activity further comprise providing radiotherapy at the site at or near the tumor, whereby anti-tumor activity is enhanced when compared to anti-tumor activity observed in response to radiotherapy alone.

Accordingly, it is an object of the present invention to provide a therapeutic method that employs heat-inducible expression of a therapeutic gene. The object is achieved in whole or in part by the present invention.

An object of the invention having been stated herein above, other objects will become evident as the description proceeds. when taken in connection with the accompanying Drawings and Laboratory Examples as best described herein below.

BRIEF DESCRIPTION OF THE DRAWINGS

FIG. 3A: EGFP plasmid injection without electroporation; FIG. 3B: EGFP plasmid injection with electroporation; FIG. 3C: β-gal plasmid injection without electroporation; FIG. 3D: β-gal plasmid injection with electroporation. The EGFP signal in FIGS. 3A and 3B appears white, and β-gal is detected as a dark staining precipitate in FIGS. 3C and 3D.

FIG. 5A shows graphs of flow cytometry analysis. 4TI cells were infected with adenovirus carrying a hsp70B-GFP transgene and treated 24 hours later at the indicated temperatures for 20 minutes. GFP expression was quantitated 24 hours later using FACS analysis. X-axis, fluorescence intensity; Y-axis, cell counts.

FIG. 5B is a Western blot that has been used to detect GFP protein. 4TI cells were infected with adenovirus carrying a hsp70B-GFP transgene and treated 24 hours later at 41° C. for 20 minutes. Proteins were extracted from heat-treated cells or non-heat treated control cells 24 hours later. GFP protein was detected using a polyclonal anti-GFP antibody (Clontech of Palo Alto, Calif.).

FIG. 5C shows fluorescence micrographs of cells infected with adenovirus carrying a hsp70B-GFP transgene. 4TI cells were infected with adenovirus carrying a hsp70B-GFP transgene and treated 24 hours later at the 43° C. for 20 minutes. Cells were observed at the indicated times (top to bottom: 0 hours, 3 hours, 9 hours, 24 hours, 48 hours) following treatment using a fluorescence microscope equipped with a FITC filter. GFP expression is observed as regions of white signal.

BRIEF DESCRIPTION OF SEQUENCES IN THE SEQUENCE LISTING

Figure 1A:
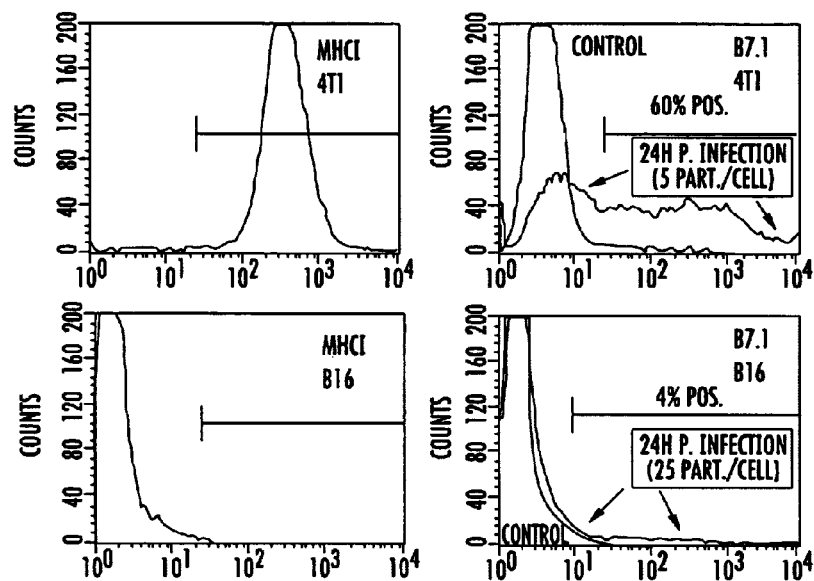
FIG. 1A presents four graphs depicting FACS analysis of the expression of MHC I (in non-infected cells) and B7.1 (in non-infected control cells and AdIL12/B7.1 infected cells) in 4T1 and B16F10 cells. The X-axis represents fluorescence intensity, and the Y-axis represents cell counts. B7.1 expression was measured before and 24 hours after infection (24 h p.infection) with AdIL/B7.1 (MOI 5 or 25/cell).

Odd-numbered SEQ ID NOs:1–11 are nucleotide sequences described in Table 1 below.

Even-numbered SEQ ID NOs:2–12 are protein sequences encoded by the immediately preceding nucleotide sequence, e.g., SEQ ID NO:2 is the protein encoded by the nucleotide sequence of SEQ ID NO:1, SEQ ID NO:4 is the protein encoded by the nucleotide sequence of SEQ ID NO:3.

SEQ ID NO:13 is a nucleotide sequence comprising a human hsp70B promoter.

TABLE 1

Summary of Sequences in the Sequence Listing

| SEQ ID NO. | description | GenBank Accession No. |
|---|---|---|
| 1 | mouse interleukin 12 p35 subunit | M86672 |
| 3 | mouse interleukin 12 p40 subunit | M86671 |
| 5 | human interleukin 12 p35 subunit | M65271 |

TABLE 1-continued

Summary of Sequences in the Sequence Listing

| SEQ ID NO. | description | GenBank Accession No. |
|---|---|---|
| 7 | human interleukin 12 p40 subunit | M65290 |
| 9 | mouse interleukin 2 | X01772 |
| 11 | human interleukin 2 | X01586 |
| 13 | human hsp70B promoter | X13229 |

DETAILED DESCRIPTION OF THE INVENTION

I. Definitions

While the following terms are believed to be well understood by one of ordinary skill in the art, the following definitions are set forth to facilitate explanation of the invention.

I.A. Nucleic Acids

The nucleic acid molecules employed in accordance with the present invention include but are not limited to the isolated nucleic acid molecules of any one of SEQ ID NOs:1, 3, 5, 7, and 9; sequences substantially identical to sequences of any one of SEQ ID NOs:1, 3, 5, 7, and 9; conservative variants thereof, subsequences and elongated sequences thereof, complementary DNA molecules, and corresponding RNA molecules. The present invention also encompasses genes, cDNAs, chimeric genes, and vectors comprising disclosed interleukin nucleic acid sequences. Preferably, the polypeptides employed in accordance with the present invention include but are not limited to the isolated polypeptides set forth as SEQ ID NOs:2, 4, 6, and 8; polypeptides substantially identical to SEQ ID NOs:2, 4, 6, and 8; functional interleukin polypeptide fragments, fusion proteins comprising the disclosed amino acid sequences, biologically functional analogs, and polypeptides that cross-react with an antibody that specifically recognizes a disclosed polypeptide.

The term "nucleic acid molecule" refers to deoxyribonucleotides or ribonucleotides and polymers thereof in either single- or double-stranded form. Unless specifically limited, the term encompasses nucleic acids containing known analogues of natural nucleotides that have similar properties as the reference natural nucleic acid. Unless otherwise indicated, a particular nucleotide sequence also implicitly encompasses conservatively modified variants thereof (e.g., degenerate codon substitutions), complementary sequences, subsequences, elongated sequences, as well as the sequence explicitly indicated. The terms "nucleic acid molecule" or "nucleotide sequence" can also be used in place of "gene", "cDNA", or "mRNA". Nucleic acids can be derived from any source, including any organism.

The term "isolated", as used in the context of a nucleic acid molecule, indicates that the nucleic acid molecule exists apart from its native environment and is not a product of nature. An isolated DNA molecule can exist in a purified form or can exist in a non-native environment such as a transgenic host cell.

The term "substantially identical", in the context of two nucleotide sequences, refers to two or more sequences or subsequences that have at least 60%, preferably about 70%, more preferably about 80%, more preferably about 90–95%, and most preferably about 99% nucleotide identity, when compared and aligned for maximum correspondence, as measured using one of the following sequence comparison algorithms (described herein below under the heading "Nucleotide and Amino Acid Sequence Comparisons") or by visual inspection. Preferably, the substantial identity exists in nucleotide sequences of at least 50 residues, more preferably in nucleotide sequence of at least about 100 residues, more preferably in nucleotide sequences of at least about 150 residues, and most preferably in nucleotide sequences comprising complete coding sequences. In one aspect, polymorphic sequences can be substantially identical sequences. The term "polymorphic" refers to the occurrence of two or more genetically determined alternative sequences or alleles in a population. An allelic difference can be as small as one base pair.

Another indication that two nucleotide sequences are substantially identical is that the two molecules specifically or substantially hybridize to each other under stringent conditions. In the context of nucleic acid hybridization, two nucleic acid sequences being compared can be designated a "probe" and a "target". A "probe" is a reference nucleic acid molecule, and a "target" is a test nucleic acid molecule, often found within a heterogeneous population of nucleic acid molecules. A "target sequence" is synonymous with a "test sequence".

A preferred nucleotide sequence employed for hybridization studies or assays includes probe sequences that are complementary to or mimic at least an about 14 to 40 nucleotide sequence of a nucleic acid molecule of the present invention. Preferably, probes comprise 14 to 20 nucleotides, or even longer where desired, such as 30, 40, 50, 60, 100, 200, 300, or 500 nucleotides or up to the full length of any of those set forth as SEQ ID NOs:1, 3, 5, 7, and 9. Such fragments can be readily prepared by, for example, directly synthesizing the fragment by chemical synthesis, by application of nucleic acid amplification technology, or by introducing selected sequences into recombinant vectors for recombinant production.

The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA).

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes*, part I chapter 2, Elsevier, New York, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize specifically to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1×SSC, SM NaCl at 65° C. An example of stringent wash conditions is 15 minutes in 0.2×SSC buffer at 65° C. (See Sambrook et al., eds. (1989) *Molecular Cloning: A Laboratory Manual*, Cold Spring Harbor Laboratory Press, Cold Spring Harbor, N.Y. for a description of SSC buffer). Often, a high stringency wash is preceded by a low stringency wash to remove background probe signal. An example of medium stringency wash conditions for a duplex of more than about 100 nucleotides, is 15 minutes in 1×SSC at 45° C. An example of low stringency wash for a duplex of more than about 100 nucleotides, is 15 minutes in 4–6×SSC at 40° C. For short probes (e.g., about 10 to 50 nucleotides), stringent conditions typically involve salt concentrations of less than about 1M $Na^+$ ion, typically about 0.01 to 1M $Na^+$ ion concentration (or other salts) at pH 7.0–8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

The following are examples of hybridization and wash conditions that can be used to clone homologous nucleotide sequences that are substantially identical to reference nucleotide sequences of the present invention: a probe nucleotide sequence preferably hybridizes to a target nucleotide sequence in 7% sodium dodecyl sulfate (SDS), 0.5M $NaPO_4$, 1 mM EDTA at 50° C. followed by washing in 2×SSC, 0.1% SDS at 50° C.; more preferably, a probe and target sequence hybridize in 7% sodium dodecyl sulfate (SDS), 0.5M $NaPO_4$, 1 mM EDTA at 50° C. followed by washing in 1×SSC, 0.1% SDS at 50° C.; more preferably, a probe and target sequence hybridize in 7% sodium dodecyl sulfate (SDS), 0.5M $NaPO_4$, 1 mM EDTA at 50° C. followed by washing in 0.5×SSC, 0.1% SDS at 50° C.; more preferably, a probe and target sequence hybridize in 7% sodium dodecyl sulfate (SDS), 0.5M $NaPO_4$, 1 mM EDTA at 50° C. followed by washing in 0.1×SSC, 0.1% SDS at 50° C.; more preferably, a probe and target sequence hybridize in 7% sodium dodecyl sulfate (SDS), 0.5M $NaPO_4$, 1 mM EDTA at 50° C. followed by washing in 0.1×SSC, 0.1% SDS at 65° C.

A further indication that two nucleic acid sequences are substantially identical is that proteins encoded by the nucleic acids are substantially identical, share an overall three-dimensional structure, are biologically functional equivalents, or are immunologically cross-reactive. These terms are defined further under the heading "Polypeptides" herein below. Nucleic acid molecules that do not hybridize to each other under stringent conditions are still substantially identical if the corresponding proteins are substantially identical. This can occur, for example, when two nucleotide sequences are significantly degenerate as permitted by the genetic code.

The term "conservatively substituted variants" refers to nucleic acid sequences having degenerate codon substitutions wherein the third position of one or more selected (or all) codons is substituted with mixed-base and/or deoxyinosine residues (Batzer et al. (1991) *Nuc Acids Res* 19:5081; Ohtsuka et al. (1985) *J Biol Chem* 260:2605–2608; Rossolini et al. (1994) *Mol Cell Probes* 8:91–98).

The term "subsequence" refers to a sequence of nucleic acids that comprises a part of a longer nucleic acid sequence.

An exemplary subsequence is a probe, described herein above, or a primer. The term "primer" as used herein refers to a contiguous sequence comprising about 8 or more deoxyribonucleotides or ribonucleotides, preferably 10–20 nucleotides, and more preferably 20–30 nucleotides of a selected nucleic acid molecule. The primers of the invention encompass oligonucleotides of sufficient length and appropriate sequence so as to provide initiation of polymerization on a nucleic acid molecule of the present invention.

The term "elongated sequence" refers to an addition of nucleotides (or other analogous molecules) incorporated into the nucleic acid. For example, a polymerase (e.g., a DNA polymerase) can add sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

The term "complementary sequences", as used herein, indicates two nucleotide sequences that comprise antiparallel nucleotide sequences capable of pairing with one another upon formation of hydrogen bonds between base pairs. As used herein, the term "complementary sequences" means nucleotide sequences which are substantially complementary, as can be assessed by the same nucleotide comparison set forth above, or is defined as being capable of hybridizing to the nucleic acid segment in question under relatively stringent conditions such as those described herein. A particular example of a complementary nucleic acid segment is an antisense oligonucleotide.

The term "gene" refers broadly to any segment of DNA associated with a biological function. A gene encompasses sequences including but not limited to a coding sequence, a promoter region, a cis-regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The term "gene expression" generally refers to the cellular processes by which a biologically active polypeptide is produced from a DNA sequence.

The present invention can also employ chimeric genes. The term "chimeric gene", as used herein, refers to a promoter region operatively linked to a nucleotide sequence encoding a therapeutic polypeptide; a nucleotide sequence producing an antisense RNA molecule; a RNA molecule having tertiary structure, such as a hairpin structure; or a double-stranded RNA molecule.

The term "operatively linked", as used herein, refers to a promoter region that is connected to a nucleotide sequence in such a way that the transcription of that nucleotide sequence is controlled and regulated by that promoter region. Techniques for operatively linking a promoter region to a nucleotide sequence are known in the art.

The terms "heterologous gene", "heterologous DNA sequence", "heterologous nucleotide sequence", "exogenous nucleic acid molecule", or "exogenous DNA segment", as used herein, each refer to a sequence that originates from a source foreign to an intended host cell or, if from the same source, is modified from its original form. Thus, a heterologous gene in a host cell includes a gene that is endogenous to the particular host cell but has been modified, for example by mutagenesis or by isolation from native cis-regulatory sequences. The terms also include non-naturally occurring multiple copies of a naturally occurring nucleotide sequence. Thus, the terms refer to a DNA segment that is foreign or heterologous to the cell, or homologous to the cell but in a position within the host cell nucleic acid wherein the element is not ordinarily found.

The term "construct" as used herein means a DNA sequence capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression.

The term "promoter" or "promoter region" each define a nucleotide sequence within a gene that is positioned 5' to a coding sequence of a same gene and functions to direct transcription of the coding sequence. The promoter region includes a transcriptional start site and at least one cis-regulatory element. The methods of the present invention preferably use a heat-inducible promoter.

The term "cis-acting regulatory sequence" or "cis-regulatory motif" or "response element", as used herein, each refer to a nucleotide sequence within the promoter region that enables responsiveness to a regulatory transcription factor. Responsiveness can encompass a decrease or an increase in transcriptional output and is mediated by binding of the transcription factor to the DNA molecule comprising the response element.

The term "transcription factor" generally refers to a protein that modulates gene expression by interaction with the cis-regulatory element and cellular components for transcription, including RNA Polymerase, Transcription Associated Factors (TAFs), chromatin-remodeling proteins, and any other relevant protein that impacts gene transcription.

A "functional portion" of a promoter gene fragment is a nucleotide sequence within a promoter region that is required for normal gene transcription. To determine nucleotide sequences that are functional, the expression of a reporter gene is assayed when variably placed under the direction of a promoter region fragment.

Promoter region fragments can be conveniently made by enzymatic digestion of a larger fragment using restriction endonucleases or DNAse I. Preferably, a functional promoter region fragment comprises about 5000 nucleotides, more preferably 2000 nucleotides, more preferably about 1000 nucleotides. Even more preferably a functional promoter region fragment comprises about 500 nucleotides, even more preferably a functional promoter region fragment comprises about 100 nucleotides, and even more preferably a functional promoter region fragment comprises about 20 nucleotides.

The terms "reporter gene" or "marker gene" or "selectable marker" each refer to a heterologous gene encoding a product that is readily observed and/or quantitated. A reporter gene is heterologous in that it originates from a source foreign to an intended host cell or, if from the same source, is modified from its original form. Non-limiting examples of detectable reporter genes that can be operatively linked to a transcriptional regulatory region can be found in Alam & Cook (1990) *Anal Biochem* 188:245–254 and PCT International Publication No. WO 97/47763. Preferred reporter genes for transcriptional analyses include the lacZ gene (See, e.g., Rose & Botstein (1983) *Meth Enzymol* 101:167–180), Green Fluorescent Protein (GFP) (Cubitt et al. (1995) *Trends Biochem Sci* 20:448–455), luciferase, or chloramphenicol acetyl transferase (CAT). Preferred reporter genes for methods to produce transgenic animals include but are not limited to antibiotic resistance genes, and more preferably the antibiotic resistance gene confers neomycin resistance. Any suitable reporter and detection method can be used, and it will be appreciated by one of skill in the art that no particular choice is essential to or a limitation of the present invention.

An amount of reporter gene can be assayed by any method for qualitatively or preferably, quantitatively determining presence or activity of the reporter gene product. The amount of reporter gene expression directed by each test promoter region fragment is compared to an amount of reporter gene expression to a control construct comprising the reporter gene in the absence of a promoter region fragment. A promoter region fragment is identified as having promoter activity when there is significant increase in an amount of reporter gene expression in a test construct as compared to a control construct. The term "significant increase", as used herein, refers to an quantified change in a measurable quality that is larger than the margin of error inherent in the measurement technique, preferably an increase by about 2-fold or greater relative to a control measurement, more preferably an increase by about 5-fold or greater, and most preferably an increase by about 10-fold or greater.

The present invention further includes vectors comprising the disclosed nuclear sequences, including plasmids, cosmids, and viral vectors. The term "vector", as used herein refers to a DNA molecule having sequences that enable its replication in a compatible host cell. A vector also includes nucleotide sequences to permit ligation of nucleotide sequences within the vector, wherein such nucleotide sequences are also replicated in a compatible host cell. A vector can also mediate recombinant production of a therapeutic polypeptide, as described further herein below.

Nucleic acids of the present invention can be cloned, synthesized, recombinantly altered, mutagenized, or combinations thereof. Standard recombinant DNA and molecular cloning techniques used to isolate nucleic acids are known in the art. Exemplary, non-limiting methods are described by Sambrook et al., eds. (1989) *Molecular Cloning*, Cold Spring Harbor Laboratory Press, Cold Spring Harbor, N.Y.; by Silhavy et al. (1984) *Experiments with Gene Fusions*, Cold Spring Harbor Laboratory Press, Cold Spring Harbor, N.Y.; by Ausubel et al. (1992) *Current Protocols in Molecular Biology*, John Wylie and Sons, Inc., New York, N.Y.; and by Glover, ed (1985) *DNA Cloning: A Practical Approach*, MRL Press, Ltd., Oxford, United Kingdom. Site-specific mutagenesis to create base pair changes, deletions, or small insertions is also known in the art as exemplified by publications. See, e.g., Adelman et al. (1983) *DNA* 2:183; Sambrook et al., eds. (1989) *Molecular Cloning*, Cold Spring Harbor Laboratory Press, Cold Spring Harbor, N.Y.

I.B. Polypeptides

The polypeptides employed in accordance with the present invention include but are not limited to a therapeutic polypeptide as defined herein below; a polypeptide substantially identical to a therapeutic polypeptide as defined herein below; a polypeptide fragment of a therapeutic polypeptide as defined herein below (preferably biologically functional fragments), fusion proteins comprising a therapeutic polypeptide as defined herein below, biologically functional analogs thereof, and polypeptides that cross-react with an antibody that specifically recognizes a therapeutic polypeptide as defined herein below.

Preferably, the polypeptides employed in accordance with the present invention include but are not limited to the isolated polypeptides set forth as SEQ ID NOs:2, 4, 6, and 8; polypeptides substantially identical to SEQ ID NOs:2, 4, 6, and 8; functional interleukin polypeptide fragments, fusion proteins comprising the disclosed amino acid sequences, biologically functional analogs, and polypeptides that cross-react with an antibody that specifically recognizes a disclosed polypeptide.

The term "isolated", as used in the context of a polypeptide, indicates that the polypeptide exists apart from its native environment and is not a product of nature. An isolated polypeptide can exist in a purified form or can exist in a non-native environment such as, for example, in a transgenic host cell.

The term "substantially identical" in the context of two or more polypeptide sequences is measured as polypeptide sequences having about 35%, or 45%, or preferably from 45–55%, or more preferably 55–65% of identical or functionally equivalent amino acids. Even more preferably, two or more "substantially identical" polypeptide sequences will have about 70%, or even more preferably about 80%, still more preferably about 90%, still more preferably about 95%, and most preferably about 99% identical or functionally equivalent amino acids. Percent "identity" and methods for determining identity are defined herein below under the heading "Nucleotide and Amino Acid Sequence Comparisons".

Substantially identical polypeptides also encompass two or more polypeptides sharing a conserved three-dimensional structure. Computational methods can be used to compare structural representations, and structural models can be generated and easily tuned to identify similarities around important active sites or ligand binding sites. See Henikoff et al. (2000) *Electrophoresis* 21(9):1700–1706; Huang et al. (2000) *Pac Symp Biocomput* 230–241; Saqi et al. (1999) *Bioinformatics* 15(6):521–522; and Barton (1998) *Acta Crystallogr D Biol Crystallogr* 54: 1139–1146.

The term "functionally equivalent" in the context of amino acid sequences is known in the art and is based on the relative similarity of the amino acid side-chain substituents. See Henikoff & Henikoff (2000) *Adv Protein Chem* 54:73–97. Relevant factors for consideration include side-chain hydrophobicity, hydrophilicity, charge, and size. For example, arginine, lysine, and histidine are all positively charged residues; that alanine, glycine, and serine are all of similar size; and that phenylalanine, tryptophan, and tyrosine all have a generally similar shape. By this analysis, described further herein below, arginine, lysine, and histidine; alanine, glycine, and serine; and phenylalanine, tryptophan, and tyrosine; are defined herein as biologically functional equivalents.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (–0.4); threonine (–0.7); serine (–0.8); tryptophan (–0.9); tyrosine (–1.3); proline (–1.6); histidine (–3.2); glutamate (–3.5); glutamine (–3.5); aspartate (–3.5); asparagine (–3.5); lysine (–3.9); and arginine (–4.5).

The importance of the hydropathic amino acid index in conferring interactive biological function on a protein is generally understood in the art (Kyte et al. (1982) *J Mol Biol* 157:105). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those that are within ±1 of the original value are particularly preferred, and those within ±0.5 of the original value are even more particularly preferred.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with its immunogenicity and antigenicity, e.g., with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (–0.4); proline (–0.5±1); alanine (–0.5); histidine (–0.5); cysteine (–1.0); methionine (–1.3); valine (–1.5); leucine (–1.8); isoleucine (–1.8); tyrosine (–2.3); phenylalanine (–2.5); tryptophan (–3.4).

In making changes based upon similar hydrophilicity values, the substitution of amino acids whose hydrophilicity values are within ±2 of the original value is preferred, those that are within ±1 of the original value are particularly preferred, and those within ±0.5 of the original value are even more particularly preferred.

The methods of the present invention can also employ polypeptide fragments or functional portions of a polypeptide, such as an interleukin polypeptide. Such functional portion need not comprise all or substantially all of the amino acid sequence of a native gene product. The term "functional" includes any biological activity or feature of the polypeptide. In the case of an interleukin polypeptide, the biological activity is preferably an immunostimulatory or anti-angiogenic activity in vivo as disclosed herein.

The present invention also includes longer sequences of a interleukin polypeptide. For example, one or more amino acids can be added to the N-terminus or C-terminus of a interleukin polypeptide. Fusion proteins comprising therapeutic polypeptide sequences (for example, interleukin polypeptide sequences) are also provided within the scope of the present invention. Methods of preparing such proteins are known in the art. Preferably, the fusion protein includes any biological activity of a therapeutic polypeptide. In the case of an interleukin polypeptide, the biological activity is preferably any biological activity of a native interleukin, for example, an immunostimulatory or anti-angiogenic activity in vivo as disclosed herein. Optionally, a fusion protein can have additional biological activities provided by the fused heterologous sequence.

The present invention also encompasses functional analogs of a therapeutic polypeptide. Functional analogs share at least one biological function with a therapeutic polypeptide (for example, an interleukin polypeptide). In the context of amino acid sequence, biologically functional analogs, as used herein, are peptides in which certain, but not most or all, of the amino acids can be substituted. Functional analogs can be created at the level of the corresponding nucleic acid molecule, altering such sequence to encode desired amino acid changes. In one embodiment, changes can be introduced to improve a biological function of the polypeptide, e.g., to improve the therapeutic effectiveness of the polypeptide (for example, an interleukin polypeptide).

The present invention also encompasses recombinant production of the disclosed polypeptides. Briefly, a nucleic acid sequence encoding a therapeutic polypeptide, is cloned into a construct, the construct is introduced into a host organism, where it is recombinantly produced.

The term "host organism" refers to any organism into which the disclosed gene therapy constructs have been introduced. Preferably, the host organism is a warm-blooded vertebrate, more preferably, a mammal.

I.C. Nucleotide and Amino Acid Sequence Comparisons

The terms "identical" or percent "identity" in the context of two or more nucleotide or polypeptide sequences, refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection.

The term "substantially identical" in regards to a nucleotide or polypeptide sequence means that a particular sequence varies from the sequence of a naturally occurring sequence by one or more deletions, substitutions, or additions, the net effect of which is to retain at least some of biological activity of the natural gene, gene product, or sequence. Such sequences include "mutant" sequences, or sequences wherein the biological activity is altered to some degree but retains at least some of the original biological activity. The term "naturally occurring", as used herein, is used to describe a composition that can be found in nature as distinct from being artificially produced by man. For example, a protein or nucleotide sequence present in an organism, which can be isolated from a source in nature and which has not been intentionally modified by man in the laboratory, is naturally occurring.

For sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison can be conducted, e.g., by the local homology algorithm of Smith & Waterman (1981) *Adv Appl Math* 2:482, by the homology alignment algorithm of Needleman & Wunsch (1970) *J Mol Biol* 48:443, by the search for similarity method of Pearson & Lipman (1988) *Proc Natl Acad Sci USA* 85:2444–2448, by computerized implementations of these algorithms (GAP, BESTFIT, FASTA, and TFASTA in the Wisconsin Genetics Software Package, Genetics Computer Group, Madison, Wis.), or by visual inspection. See generally, Ausubel et al. (1992) *Current Protocols in Molecular Biology*, John Wylie & Sons, Inc., New York, N.Y.

A preferred algorithm for determining percent sequence identity and sequence similarity is the BLAST algorithm, which is described in Altschul et al. (1990) *J Mol Biol* 215: 403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff (1989) *Proc Natl Acad Sci USA* 89:10915.

In addition to calculating percent sequence identity, the BLAST algorithm also performs a statistical analysis of the similarity between two sequences. See, e.g., Karlin & Altschul (1993) *Proc Natl Acad Sci USA* 90:5873–5887. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

I.D. Immune Responses

The term "immune response" is meant to refer to any response to an antigen or antigenic determinant by the immune system of a vertebrate subject. Exemplary immune responses include humoral immune responses (e.g. production of antigen-specific antibodies) and cell-mediated immune responses (e.g. lymphocyte proliferation), as defined herein below. Representative molecules that can elicit an immune response and that can be used in accordance with the present invention include interleukins, for example interleukin 2 (IL2) and interleukin 12 (IL12), and the B lymphocyte activation antigen B7.1.

The term "immune system" includes all the cells, tissues, systems, structures and processes, including non-specific and specific categories, which provide a defense against antigenic molecules, including potential pathogens, in a vertebrate subject. As is well known in the art, the non-specific immune system includes phagocytic cells such as neutrophils, monocytes, tissue macrophages, Kupffer cells, alveolar macrophages, dendritic cells and microglia. The specific immune system refers to the cells and other structures that impart specific immunity within a host. Included among these cells are the lymphocytes, particularly the B cell lymphocytes and the T cell lymphocytes. These cells also include natural killer (NK) cells and lymphokine activated killer (LAK) cells. Additionally, antibody-producing cells, like B lymphocytes, and the antibodies produced by the antibody-producing cells are also included within the term "immune system".

The term "systemic immune response" is meant to refer to an immune response in the lymph node-, spleen-, or gut-associated lymphoid tissues wherein cells, such as B lymphocytes, of the immune system are developed. For example, a systemic immune response can comprise the production of serum IgG's. Further, systemic immune response refers to antigen-specific antibodies circulating in the blood stream and antigen-specific cells in lymphoid tissue in systemic compartments such as the spleen and lymph nodes.

The terms "humoral immunity" or "humoral immune response" are meant to refer to the form of acquired immunity in which antibody molecules are secreted in response to antigenic stimulation.

The terms "cell-mediated immunity" and "cell-mediated immune response" are meant to refer to the immunological defense provided by lymphocytes, such as that defense provided by T cell lymphocytes when they come into close proximity to their target cells. A cell-mediated immune response also comprises lymphocyte proliferation. When "lymphocyte proliferation" is measured, the ability of lymphocytes to proliferate in response to specific antigen is measured. Lymphocyte proliferation is meant to refer to B cell, T-helper cell, or CTL cell proliferation.

The term "CTL response" is meant to refer to the ability of an antigen-specific cell to lyse and kill a cell expressing the specific antigen. As described herein below, standard, art-recognized CTL assays are performed to measure CTL activity.

Representative therapeutic proteins with immunostimulatory effects include but are not limited to cytokines (e.g., IL2, IL4, IL7, IL12, interferons, granulocyte-macrophage colony-stimulating factor (GM-CSF), tumor necrosis factor alpha (TNF-α)), immunomodulatory cell surface proteins (e.g., human leukocyte antigen (HLA proteins), co-stimulatory molecules, and tumor-associated antigens. See Mackensen et al. (1997) *Cytokine Growth Factor Rev* 8(2): 119–128; Walther & Stein (1999) *Mol Biotechnol* 13(1): 21–28; Kirk & Mule (2000) *Hum Gene Ther* 11(6):797–806; and references cited therein.

I.E. Anti-angiogenic Activity

The term "angiogenesis" refers to the process by which new blood vessels are formed. The term "anti-angiogenic response" and "anti-angiogenic activity" as used herein, each refer to a biological process wherein the formation of new blood vessels is inhibited.

Representative proteins with anti-angiogenic activities that can be used in accordance with the present invention include: thrombospondin I (Kosfeld et al (1993) *J Biol Chem* 267:16230–16236; Tolsma et al. (1993) *J. Cell Biol.*, 122: 497–511; Dameron et al. (1995) *Science* 265:1582–1584), metallospondin proteins (Carpizo & Iruela-Arispe (2000) *Cancer Metastasis Rev* 19(1–2):159–165), class I interferons (Albini et al. (2000) *Am J Pathol* 156(4):1381–1393), IL12 (Voest et al. (1995) *J Natl Cancer Inst*, 87:581–586), protamine (Ingber et al. (1990) *Nature,* 348:555–557), angiostatin (O'Reilly et al. (1994) *Cell* 79:315–328), laminin (Sakamoto et al. (1991) *Cancer Res.*,5:903–906), endostatin (O'Reilly et al. (1997) *Cell* 88:277–285), and a prolactin fragment (Clapp et al. (1993) *Endocrinol.*, 133: 1292–1299). In addition, several anti-angiogenic peptides have been isolated from these proteins (Maione et al. (1990) *Science* 247:77–79; Woltering et al. (1991) *J Surg Res.,* 50:245–251; and Eijan et al. (1991) *Mol Biother* 3:38–40).

II. Therapeutic Genes

The methods of the present invention employ a gene therapy construct comprising a nucleic acid molecule that encodes a polypeptide having a therapeutic biological activity (also referred to herein as a "therapeutic polypeptide"), including but not limited to immunostimulatory molecules, tumor suppressor gene products/antigens, antimetabolites, suicide gene products, and anti-angiogenic factors. See Mackensen et al. (1997) *Cytokine Growth Factor Rev* 8(2): 119–128; Walther & Stein (1999) *Mol Biotechnol* 13(1): 21–28; Kirk & Mule (2000) *Hum Gene Ther* 11(6):797–806; and references cited therein.

Angiogenesis and suppressed immune response play a central role in the pathogenesis of malignant disease and tumor growth, invasion, and metastasis. Thus, preferably, the therapeutic polypeptide has an ability to induce an immune response and/or an anti-angiogenic response in vivo. In one embodiment, a gene therapy construct of the present invention encodes a therapeutic gene that displays both immunostimulatory and anti-angiogenic activities, for example, IL12 (see Dias et al. (1998) *Int J Cancer* 75(1): 151–157, and references cited herein below), interferon-α (O'Byrne et al. (2000) *Eur J Cancer* 36(2):151–169, and references cited therein), or a chemokine (Nomura & Hasegawa (2000) *Anticancer Res* 20(6A):4073–4080, and references cited therein). In another embodiment, a gene therapy construct of the present invention encodes a gene product with immunostimulatory activity and a gene product having anti-angiogenic activity. See, e.g. Narvaiza et al. (2000) *J Immunol* 164:3112–3122.

IL12, optionally in combination with the co-stimulatory agent B7.1, is a preferred therapeutic polypeptide because local application of virus encoding IL12 or B7.1, as well as the combination of IL12 and B7.1, appear to improve immune responses against tumors (Pützer et al. (1997) *Proc Natl Acad Sci USA* 94:10889–10894).

In one embodiment, the present invention comprises a gene therapy construct encoding an IL12 polypeptide capable of eliciting an immune response and/or an anti-angiogenic response. Interleukin-12 (IL12) is a disulfide linked heterodimer composed of 2 subunits, p35 and p40. IL12 stimulates T and NK cells to secrete interferon-gamma (IFN-γ) and augments T and NK cell proliferation and cytolytic activity (Kobayashi et al. (1989) *J Exp Med* 1708:827; Wolf et al. (1991) *J Immunol* 146:3074; D'Andre et al. (1992) *J Exp Med* 176:1387; Gately et al. (1994) *Int Immunol* 6:157; Robertson et al. (1992) *J Exp Med* 175: 779). Through these functions, IL12 promotes early inflammatory responses and the development of CD4+ T helper (Th1) cells that favor cell-mediated immunity (Manetti et al. (1993) *J Exp Med* 177:1199; Hsieh et al. (1993) *Science* 260:547). IL12 further inhibits angiogenesis, possibly through a NK cell-mediated mechanism (Voest et al. (1995) *J Natl Cancer Inst* 87(8):581–586; Majewski et al. (1996) *J Invest Dermatol* 106(5):1114–1118; Yao et al. (1999) *Blood* 93(5):1612–1621).

Preferably, the IL12 polypeptide encoded by a gene therapy construct of the present invention displays one or more biological properties of a naturally occurring IL12 polypeptide. Such biological activity can be assessed using methods described in the foregoing publications and using methods disclosed in Examples 7–14 herein below.

Preferably, the functional IL12 polypeptide comprises a first subunit and a second subunit. The first subunit can comprise: (a) a polypeptide encoded by a nucleic acid molecule of SEQ ID NO:1 or 5; (b) a polypeptide encoded by a nucleic acid substantially identical to SEQ ID NO:1 or 5; (c) a polypeptide having an amino acid sequence set forth as SEQ ID NO:2 or 6; (d) a polypeptide having an amino acid sequence substantially identical to SEQ ID NO:2 or 6; or (e) a polypeptide that is a biological equivalent of SEQ ID NO:2 or 6. The second subunit can comprise: (a) a polypeptide encoded by a nucleic acid molecule of SEQ ID NO:3 or 7; (b) a polypeptide encoded by a nucleic acid substantially identical to SEQ ID NO:3 or 7; (c) a polypeptide having an amino acid sequence set forth as SEQ ID NO:4 or 8; (d) a polypeptide having an amino acid sequence substantially identical to SEQ ID NO:4 or 8; or (e) a polypeptide that is a biological equivalent of SEQ ID NO:4 or 8. Preferably, the polynucleotide encoding an IL12 polypeptide comprises: (a) a nucleotide sequence set forth as SEQ ID NO:1, 3, 5, or 7; or (b) a nucleotide sequence that is substantially identical to SEQ ID NO:1, 3, 5, or 7.

In another embodiment, the invention comprises a gene therapy construct encoding an IL2 polypeptide. IL12 is an immunostimulatory molecule that shows therapeutic activity in a variety of cancers, including renal cancer, breast cancer, bladder cancer, and malignant melanoma. The anti-tumor activity of IL2 is related to its capacity to expand and activate NK cells and T cells that express IL2 receptors. See, e.g., Margolin (2000) *Semin Oncol* 27(2):194–203; Gore (1996) *Cancer Biother Radiopharm* 11 (5):281–283; Deshmukh et al. (2001) *J Neurosurgery* 94(2):287–292; Larchian et al. (2000) *Clin Cancer Res* 6(7):2913–2920; Horiguchi et al. (2000) *Gene Ther* 7(10):844–851; and references cited therein. IL2 has also been used successfully when co-administered with anti-tumor vaccines. See Overwijk et al. (2000) *Cancer J Sci Am* 6 Suppl 1:S76–80, and references cited therein.

Preferably, the IL2 polypeptide encoded by a gene therapy construct of the present invention displays one or more biological properties of a naturally occurring IL2 polypeptide. IL2-induced proliferation can be measured, for example, by $^3$H-thymidine incorporation in CTLL-2 cells, as described in European Patent No. 0 439 095. The biological properties of an IL2 polypeptide can further be assessed using methods described in the foregoing publications and using methods disclosed in Examples 7–14 herein below.

Preferably, the IL2 polypeptide employed in a method of the present invention comprises: (a) a polypeptide encoded by a nucleic acid molecule of SEQ ID NO:9 or 11; (b) a polypeptide encoded by a nucleic acid substantially identical to SEQ ID NO:9 or 11; (c) a polypeptide having an amino acid sequence set forth as SEQ ID NO:10 or 12; (d) a polypeptide having an amino acid sequence substantially identical to SEQ ID NO:10 or 12; or (e) a polypeptide that is a biological equivalent of SEQ ID NO:10 or 12. Preferably, the polynucleotide encoding an IL2 polypeptide comprises: (a) a nucleotide sequence set forth as SEQ ID NO:9 or 11; or (b) a nucleotide sequence that is substantially identical to SEQ ID NO:9 or 11.

Despite the evidence that immunostimulatory and anti-angiogenic molecules can be useful as anti-tumor agents, the advancement of such knowledge to effective gene therapy methods is unpredictable in the art, and the mere suggestion is not instructive for performing gene therapy treatments. By contrast, the present invention discloses in vivo models of inhibition of tumor growth using inducible expression of a therapeutic gene.

The present invention also encompasses IL12 or IL2 polypeptides that are engineered to differ in activity from naturally occurring IL12 or IL2. For example, IL12 can be engineered to more potently inhibit angiogenesis. Similarly, IL2 can be engineered to selectively stimulate a subset of NK and/or T cells. See Shanafelt et al. (2000) *Nat Biotechnol* 18(11):1197–1202.

III. Gene Therapy Delivery Systems

The present invention also provides gene therapy constructs or vectors. The particular vector employed in accordance with the methods of the present invention is not intended to be a limitation of the method for heat-induced expression of therapeutic genes by hyperthermia. Thus, any suitable vector for delivery of the gene therapy construct can be used.

The vector can be a viral vector or a non-viral vector. Suitable viral vectors include adenoviruses, adeno-associated viruses (AAVs), retroviruses, pseudotyped retroviruses, herpes viruses, vaccinia viruses, Semiliki forest virus, and baculoviruses. Suitable non-viral vectors comprise plasmids, water-oil emulsions, polethylene imines, dendrimers, micelles, microcapsules, liposomes, and cationic lipids. Polymeric carriers for gene therapy constructs can be used as described in Goldman et al (1997) *Nat Biotechnol* 15:462 and U.S. Pat. Nos. 4,551,482 and 5,714,166. Peptide carriers are described in U.S. Pat. No. 5,574,172. Where appropriate, two or more types of vectors can be used together. For example, a plasmid vector can be used in conjunction with liposomes. Currently, a preferred embodiment of the present invention envisions the use of an adenovirus, a plasmid, or a liposome, each described further herein below.

As desired, vectors, especially viral vectors, can be selected to achieve integration of the nucleic acid of the construct of the invention, into the genome of the cells to be transformed or transfected. Including a ligand in the complex having affinity for a specific cellular marker can also enhance delivery of the complexes to a target in vivo. Ligands include antibodies, cell surface markers, viral peptides, and the like, which act to home the complexes to tumor vasculature or endothelial cells associated with tumor vasculature, or to tumor cells themselves. A complex can comprise a construct or a secreted therapeutic polypeptide encoded by a construct. An antibody ligand can be an antibody or antibody fragment specific towards a tumor marker such as Her2/neu (v-erb-b2 avian erythroblastic leukemia viral oncogene homologue 2), CEA (carcinoembryonic antigen), ferritin receptor, or a marker associated with tumor vasculature (integrins, tissue factor, or β-fibronectin isoform). Antibodies or other ligands can be coupled to carriers such as liposomes and viruses, as is known in the art. See, e.g., Neri et al. (1997) *Nat BioTechnology* 15:1271; Kirpotin et al. (1997) *Biochemistry* 36:66; Cheng (1996) *Human Gene Therapy* 7:275; Pasqualini et al. (1997) *Nat Biotechnology* 15:542; Park et al. (1997) *Proc Am Ass Canc Res* 38:342 (1997); Nabel (1997) "Vectors for Gene Therapy" in *Current Protocols in Human Genetics* on CD-ROM, John Wiley & Sons, New York, N.Y.; U.S. Pat. No. 6,071,890; and European Patent No. 0 439 095. Alternatively, pseudotyping of a retrovirus can be used to target a virus towards a particular cell (Marin et al. (1997) *Mol Med Today* 3:396).

Suitable methods for introduction of a gene therapy construct into cells include direct injection into a cell or cell mass, particle-mediated gene transfer, electroporation, DEAE-Dextran transfection, liposome-mediated transfection, viral infection, and combinations thereof. A delivery method is selected based considerations such as the vector type, the toxicity of the encoded gene, and the condition to be treated.

III.A. Viral Gene Therapy Vectors

Viral vectors of the invention are preferably disabled, e.g. replication-deficient. That is, they lack one or more functional genes required for their replication, which prevents their uncontrolled replication in vivo and avoids undesirable side effects of viral infection. Preferably, all of the viral genome is removed except for the minimum genomic elements required to package the viral genome incorporating the therapeutic gene into the viral coat or capsid. For example, it is desirable to delete all the viral genome except the Long Terminal Repeats (LTRs) or Invented Terminal Repeats (ITRs) and a packaging signal. In the case of adenoviruses, deletions are typically made in the E1 region and optionally in one or more of the E2, E3 and/or E4 regions. In the case of retroviruses, genes required for replication, such as env and/or gag/pol can be deleted. Deletion of sequences can be achieved by recombinant means, for example, involving digestion with appropriate restriction enzymes, followed by religation. Replication-competent self-limiting or self-destructing viral vectors can also be used.

Nucleic acid constructs of the invention can be incorporated into viral genomes by any suitable means known in the art. Typically, such incorporation will be performed by ligating the construct into an appropriate restriction site in the genome of the virus. Viral genomes can then be packaged into viral coats or capsids by any suitable procedure. In particular, any suitable packaging cell line can be used to generate viral vectors of the invention. These packaging lines complement the replication-deficient viral genomes of the invention, as they include, typically incorporated into their genomes, the genes which have been deleted from the replication-deficient genome. Thus, the use of packaging lines allows viral vectors of the invention to be generated in culture.

Suitable packaging lines for retroviruses include derivatives of PA317 cells, ψ-2 cells, CRE cells, CRIP cells, E-86-GP cells, and 293GP cells. Line 293 cells can be used for adenoviruses and adeno-associated viruses.

Figure 1B:
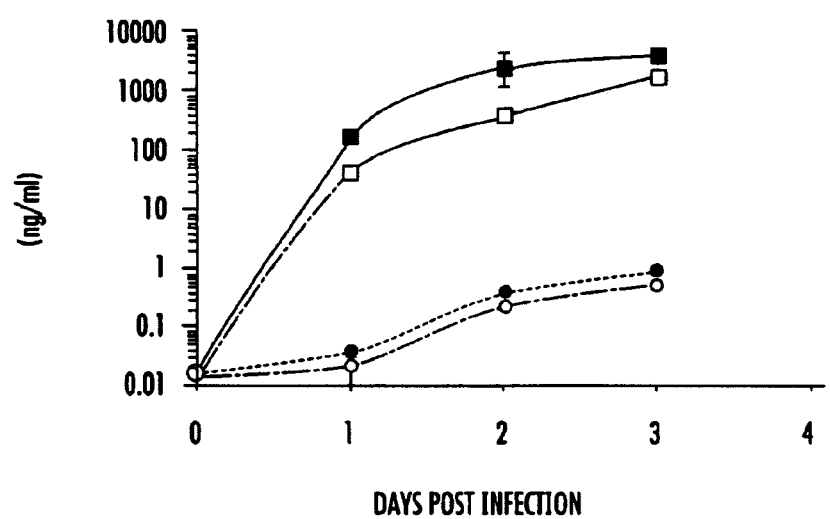
FIG. 1B is a graph depicting the concentration (ng IL/g tumor) of IL12 in cell culture supernatants of 4T1 and B16.F10 cells at 24, 48, and 72 hours post-infection with AdIL12/B7.1 (MOI 10/cell or 25/cell). (□) 4T1, MOI 25/cell; (■) 4T1, MOI 25/cell; (○) B16.F10, MOI 10/cell; (●) B16.F10, MOI 25/cell.

In a preferred embodiment of the invention, the vector is an adenoviral vector. In vitro gene expression of an adenoviral gene therapy construct was assessed in 4T1 and B16.F10 cells as described in Example 1. The immunophenotype for the two tumor lines used is different. While both are negative for B.71, 4T1 is positive for MHC-I while B16.F10 is negative for MHC-I (FIG. 1A). Both B7.1 and IL12 were effectively expressed in AdIL12/B7.1 infected 4T1 cells grown in vitro with 40–60% of cells positive for B7.1 24 hours after infection (FIG. 1A) and a maximal IL12 concentration of 4.5 μg/ml in the supernatant 72 hours after infection (FIG. 1B). The infection efficiency was lower for B16.F10 with 2–4% of cells being B7.1 positive 24 hours after infection (FIG. 1A). The maximal IL12 concentration (FIG. 1B) was 1 ng/ml in the supernatant at 72 hours post-infection.

Gene therapy with intratumorally-injected constructs offers the potential to restrict therapeutic gene expression in the tumor. However, intratumoral versus systemic levels of transgene following intratumoral injection has not been clearly established. Leakage of an empty adenoviral vector does not introduce systemic toxicity unless exceedingly high doses are administered. However, systemic toxicity of therapeutic proteins has limited the usefulness of therapeutic constructs encoding such proteins. Thus, an important feature of a gene therapy system of the present invention pertains to a method for effectively limiting the vector distribution and expression to the site of provision.

Figure 2:
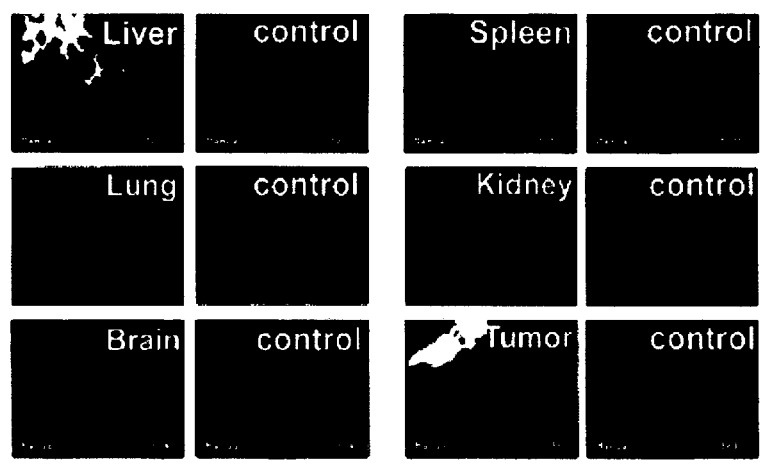
FIG. 2 presents fluorescence micrographs (magnification 20×) depicting systemic dissemination of adenovirus after intratumoral injection. Expression of GFP is observed as regions of white signal. Micrographs of organs derived from tumor-bearing C57BL/6 mice after intratumoral injection of adenovirus constitutively expressing GFP (AdGFP) are labeled as "Liver", "Lung", "Brain", "Spleen", "Kidney", and "Tumor". Micrographs of organs derived from non-injected animals are labeled "control" and are presented adjacent to the corresponding organ derived from the injected animal.

In vivo intratumoral and leakage-related systemic expression of an adenoviral reporter gene construct was assessed in a murine melanoma model as described in Example 2. A substantial amount of adenoviral vector was observed to disseminate into the systemic circulation and to infect parenchymal organs (FIG. 2), in addition to infecting a fraction of the tumor following intratumoral injection. This observation is similar to that described by Emtage et al. (1999) *Hum Gene Ther* 10:697–709; by Nasu et al. (1999) *Gene Ther* 6:338–349; by Bramson et al. (1997) *Gene Ther* 4:1069–1076; and by Zhang et al. (1999) *Endocrinology* 140:2152–2158.

III.B. Plasmid Gene Therapy Vectors

In a preferred embodiment of the invention, a therapeutic gene is encoded by a naked plasmid. The toxicity of plasmid DNA is generally low and large-scale production is relatively easy. A major obstacle that has prevented the widespread application of plasmid DNA is its relative inefficiency in gene transduction. Electroporation has been used to effectively transport molecules including DNA into living cells in vitro (Neumann et al. (1982) *EMBO J* 1:841–845). Recent reports have demonstrated the use of electroporation in vivo, for example to enhance local efficiency of chemotherapeutic agents (Hofmann et al. (1999) *Crit Rev Ther Drug Carrier Syst* 16:523–569; Sersa et al. (2000) *Clin Cancer Res* 6:863–867).

Figures 3A, 3B:
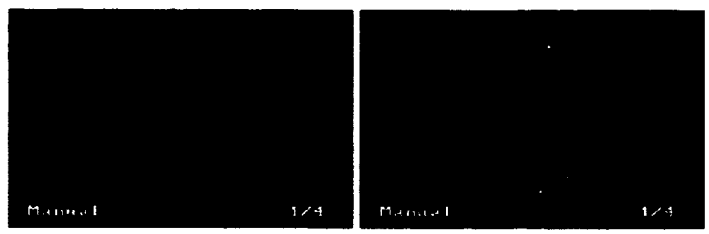
FIGS. 3A–3D present photomicrographs depicting in vivo expression of reporter genes in B16.F10 melanoma 48 hours after injection of 50%g EGFP or β-gal plasmid (in 50 μl PBS) into tumors (at 5–7 mm in diameter or 65–179 mm$^3$ in volume) with or without consecutive electroporation. 250 µm sections were prepared using fresh tumor tissues that had not been fixed or frozen, and were viewed at 500× magnification.
Figures 3C, 3D:
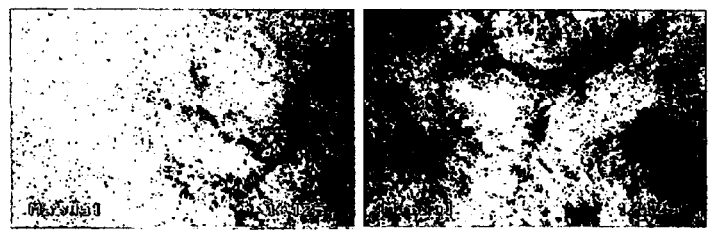
Figure 4:
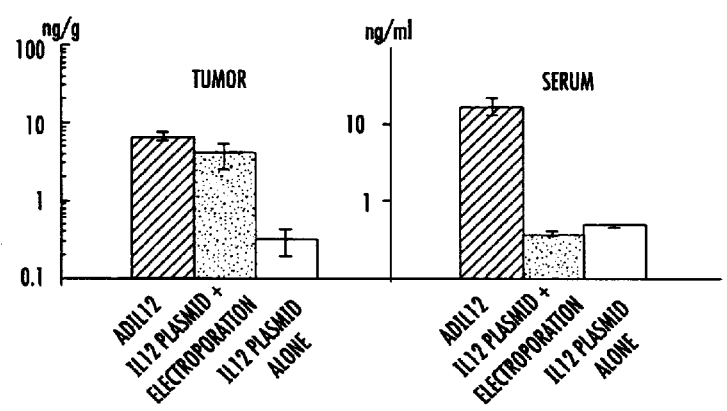
FIG. 4 is a bar graph illustrating maximum IL12 levels in tumor (ng IL/g tumor) and serum (ng IL/ml serum) after intratumoral injection of IL12 plasmid (50 µg in 50 µl) with consecutive electroporation or after intratumoral injection of recombinant adenovirus encoding IL12 ($3 \times 10^8$ pfu AdIL12). For adenovirus, the samples were taken 2 days after viral injections. For plasmids, the samples were taken 5 days after plasmid injection. The results are plotted as mean±standard error. Each data point represents results from 2–4 animals. Hatched bar, AdIL12; stippled bar, IL12 plasmid+electroporation; open bar, IL12 plasmid without electroporation.

Disclosed herein is a novel approach to anti-tumor immuno-gene therapy that combines plasmid delivery of a therapeutic construct and in vivo electroporation. Significant intratumoral gene transduction was achieved by electroporation of tumors that had been injected with naked plasmids encoding reporter genes and cytokine genes (IL2 and IL12) under the control of a constitutive cytomegalovirus promoter as described in Examples 3 and 4 (FIGS. 3 and 4). In addition, significant tumor growth delay could be achieved in a murine melanoma line B16.F10 with the cytokine genes, discussed further herein below under the heading "Gene Therapy in Animal Models".

An important feature of gene therapy methods is provision of effective doses of the gene therapy construct in the tumor while minimizing deleterious systemic expression or leakage of the construct. For example, even with strictly local adenoviral infection, there can be systemic toxicity due to virus leaking into the systemic circulation, and subsequently infecting the liver with high efficiency (Emtage et al. (1999) *Hum Gene Ther* 10:697–709; Nasu et al. (1999) *Gene Ther* 6:338–349). Systemic and intratumoral transgene levels were compared following adenoviral or plasmid/electroporation delivery as described in Example 4. Systemic transgene levels were negligible when compared to intratumoral adenovirus-mediated IL12 gene delivery, which leads to significantly higher systemic cytokine levels (FIG. 4).

Thus, the methods disclosed herein demonstrate that naked plasmid and in vivo electroporation mediated gene therapy can be therapeutically efficacious while maintaining low systemic toxicity. Another advantage of plasmid-based delivery is its inherent low immunogenicity, which facilitates multiple, repeated administration as necessary in some treatment protocols.

Plasmid transfection efficiency in vivo encompasses a multitude of parameters, such as the amount of plasmid, time between plasmid injection and electroporation, temperature during electroporation, and electrode geometry and pulse parameters (field strength, pulse length, pulse sequence, etc.). The methods disclosed herein can be optimized for a particular application by methods known to one of skill in the art, and the present invention encompasses such variations. See, e.g., Heller et al. (1996) *FEBS Lett* 389:225–228; Vicat et al. (2000) *Hum Gene Ther* 11:909–916; Miklavcic et al. (1998) *Biophys J* 74:2152–2158.

III.C. Liposomes

The present invention also envisions the use of gene therapy constructs comprising liposomes. A representative method for liposome preparation is described in Example 19. Liposomes can also be prepared by any of a variety of techniques that are known in the art. See e.g., Betageri et al. (1993) *Liposome Drug Delivery Systems*, Technomic Publishing, Lancaster; Gregoriadis, ed. (1993) *Liposome Technology*, CRC Press, Boca Raton, Fla.; Janoff, ed. (1999) *Liposomes: Rational Design*, M. Dekker, New York, N.Y.; Lasic & Martin (1995) *Stealth Liposomes*, CRC Press, Boca Raton, Fla.; Nabel (1997) "Vectors for Gene Therapy" in *Current Protocols in Human Genetics* on CD-ROM, John Wiley & Sons, New York, N.Y.; and U.S. Pat. Nos. 4,235, 871; 4,551,482; 6,197,333; and 6,132,766. Temperature-sensitive liposomes can also be used, for example THERMOSOMES™ as disclosed in U.S. Pat. No. 6,200,598. Entrapment of an active agent within liposomes of the present invention can also be carried out using any conventional method in the art. In preparing liposome compositions, stabilizers such as antioxidants and other additives can be used.

For predictable delivery, a liposome preparation can comprise liposomes of substantially similar size by repeated passing of the preparation through polycarbonate filters having the desired pore size. Liposome size can be confirmed by dynamic light scattering as is known in the art (Kong et al. (2000) *Cancer Research* 60:4440–4445; Kong et al. (2001) *Cancer Research* 61:3027–3032). Preferably, liposomes are about 100 nm–600 nm in diameter, more preferably about 100 nm–400 nm in diameter, and more preferably about 100 nm in diameter. When administered intravenously, 100 nm–600 nm are not observed to cross vascular barriers in normal tumors. However, abnormal blood vessels within a tumor can permit liposome extravasation. See e.g., Rome et al. (1994) *Arterioscler Thromb* 14(1):148–161; Yuan et al. (1995) *Cancer Research* 555 (17):3752–3756; and U.S. Pat. No. 5,213,804. In addition, heat treatment of the tissue can facilitate such delivery as described further herein below under the heading *Administration* and in Example 19. See also Kong et al. (2000) *Cancer Research* 60:4440–4445; Kong et al. (2001) *Cancer Research* 61:3027–3032.

Other lipid carriers can also be used in accordance with the claimed invention, such as lipid microparticles, micelles, lipid suspensions, and lipid emulsions. See, e.g., Labat-Moleur et al. (1996) *Gene Therapy* 3:1010–1017; U.S. Pat. Nos. 5,011,634; 6,056,938; 6,217886; 5,948,767; and 6,210, 707.

IV. Heat-Inducible Gene Therapy Vectors

In an effort to maximize intratumoral levels of a gene product encoded by a gene therapy vector, and concomitantly minimize potentially toxic systemic levels of the same encoded gene product, constructs were developed that employ a heat-inducible promoter. As disclosed herein, high intratumoral levels of a therapeutic transgene can be achieved while systemic expression is substantially eliminated. Thus, in one embodiment of the present invention, the combination of intratumoral, adenovirus-mediated provision of a gene therapy vector and inducible expression of a therapeutic gene can increase the safety and efficacy of adenovirus-based tumor gene therapy.

Any heat-inducible promoter can be used in accordance with the methods of the present invention, including but not limited to a heat-responsive element in a heat shock gene (e.g., hsp20–30, hsp27, hsp40, hsp60, hsp70, and hsp90). See Easton et al. (2000) *Cell Stress Chaperones* 5(4): 276–290; Csermely et al. (1998) *Pharmacol Ther* 79(2): 129–168; Ohtsuka & Hata (2000) *Int J Hyperthermia* 16(3): 231–245; and references cited therein. Sequence similarity to heat shock proteins and heat-responsive promoter elements have also been recognized in genes initially characterized with respect to other functions, and the DNA sequences that confer heat inducibility are suitable for use in the disclosed gene therapy vectors. For example, expression of glucose-responsive genes (e.g., grp94, grp78, mortalin/grp75) (Merrick et al. (1997) *Cancer Lett* 119(2):185–190; Kiang et al. (1998) *FASEB J* 12(14):1571–16–579), *calreticulin* (Szewczenko-Pawlikowski et al. (1997) *Mol Cell Biochem* 177(1–2):145–152); *clusterin* (Viard et al. (1999) *J Invest Dermatol* 112(3):290–296; Michel et al. (1997) *Biochem J* 328(Ptl):45–50; Clark & Griswold (1997) *J Androl* 18(3):257–263), histocompatibility class *I* gene (HLA-G) (Ibrahim et al. (2000) *Cell Stress Chaperones* 5(3):207–218), and the Kunitz protease isoform of amyloid precursor protein (Shepherd et al. (2000) *Neuroscience* 99(2):317–325) are up-regulated in response to heat.

In the case of *clusterin*, a 14 base pair element that is sufficient for heat-inducibility has been delineated (Michel et al. (1997) *Biochem J* 328(Pt1):45–50). Similarly, a two-sequence unit comprising a 10- and a 14-base pair element in the *calreticulin* promoter region has been shown to confer heat-inducibility (Szewczenko-Pawlikowski et al. (1997) *Mol Cell Biochem* 177(1–2):145–152).

For genes that are up-regulated in response to heat, wherein the precise sequence that confers heat inducibility has not been determined, the responsive sequence can be defined by methods known to one of ordinary skill in the art. Within a candidate promoter region or response element, the presence of regulatory proteins bound to a nucleic acid sequence can be detected using a variety of methods well known to those skilled in the art (Ausubel et al. (1992) *Current Protocols in Molecular Biology*, John Wylie and Sons, Inc., New York, N.Y.). Briefly, in vivo footprinting assays demonstrate protection of DNA sequences from chemical and enzymatic modification within living or permeabilized cells. Similarly, in vitro footprinting assays show protection of DNA sequences from chemical or enzymatic modification using protein extracts. Nitrocellulose filter-binding assays and gel electrophoresis mobility shift assays (EMSAs) track the presence of radiolabeled regulatory DNA elements based on provision of candidate transcription factors. Computer analysis programs, for example TFSEARCH version 1.3 (Yutaka Akiyama: "TFSEARCH: Searching Transcription Factor Binding Sites", http://www.rwcp.or.jp/papia/), can also be used to locate consensus sequences of known cis-regulatory elements within a genomic region.

A heat-inducible promoter of the present invention can be concatamerized or combined with additional elements to amplify transcriptional activity, such as the GAGA element described by Bevilacqua et al. (2000) *Development* 127(7): 1541–1551. Alternatively or in addition, the heat inducible promoter can be combined with an element that acts as an enhancer of mRNA translation. Vivinus et al. (2001) *Eur J Biochem* 268(7):1908–1917 describe an element from the 5'UTR of human hsp70 that increases the efficiency of mRNA translation unaccompanied by any alteration in mRNA levels, suggesting that the element facilitates translation.

A heat-inducible promoter of the present invention can further be responsive to non-heat stimuli that can be used in combined therapy treatments as disclosed herein. For example, the mortalin promoter is induced by low doses of ionizing radiation (Sadekova (1997) *Int J Radiat Biol* 72(6): 653–660), the hsp27 promoter is activated by 17β-estradiol and estrogen receptor agonists (Porter et al. (2001) *J Mol Endocrinol* 26(1):31–42), the HLA-G promoter is induced by arsenite, hsp promoters can be activated by photodynamic therapy (Luna et al. (2000) *Cancer Res* 60(6):1637–1644). Thus, a heat-inducible promoter used in accordance with the present invention can comprise additional inducible features or additional DNA elements that support combined therapy treatments.

A heat-inducible promoter can be derived from any biological source, including form a source that is heterologous to the intended subject to be treated. As one example, the myobacterial hsp60 promoter can direct efficient heat-inducible expression in human mononuclear cells (Luo et al. (2001) *Clin Exp Immunol* 123(2):264–470).

In accordance with the present invention, selection of a heat-inducible promoter can incorporate factors such as tissue-specific activation. For example, hsp70 is transcriptionally impaired in stressed neuroblastoma cells (Drujan & De Maio (1999) 12(6):443–448). Thus, a modified hsp70 or an alternate heat-inducible promoter, such as the mortalin promoter, which is up-regulated in human brain tumors (Takano et al. (1997) *Exp Cell Res* 237(1):38–45), might be more effective for this application. A heat-inducible promoter employed in methods of the present invention can show selective up-regulation in tumor cells as described, for example, for mortalin (Takano et al. (1997) *Exp Cell Res* 237(1):38–45), hsp27 and *calreticulin* (Szewczenko-Pawlikowski et al. (1997) *Mol Cell Biochem* 177(1–2):145–152; Yu et al. (2000) *Electrophoresis* 21(14):3058–3068), grp94 and grp78 (Gazit et al. (1999) *Breast Cancer Res Treat* 54(2):135–146), hsp27, hsp70, hsp73, and hsp90 (Cardillo et al. (2000) *Anticancer Res* 20(6B):4579–4583; Strik et al. (2000) *Anticancer Res* 20(6B):4457–4552). Effective expression of a therapeutic gene operatively linked to a heat-inducible promoter, as disclosed herein, requires heat treatment by any one of several methods, optionally in combination with tissue-specific transcriptional features of the promoter.

In a preferred embodiment of the present invention, the heat-inducible promoter comprises: (a) the nucleotide sequence set forth as SEQ ID NO:13; or (b) a nucleotide sequence substantially identical to SEQ ID NO:13. In another preferred embodiment, the heat-inducible promoter comprises a human heat-inducible promoter, for example, the 225 base pair region of human hsp70B that is sufficient for heat induction (International Publication No. WO 95/00178).

Figure 5A:
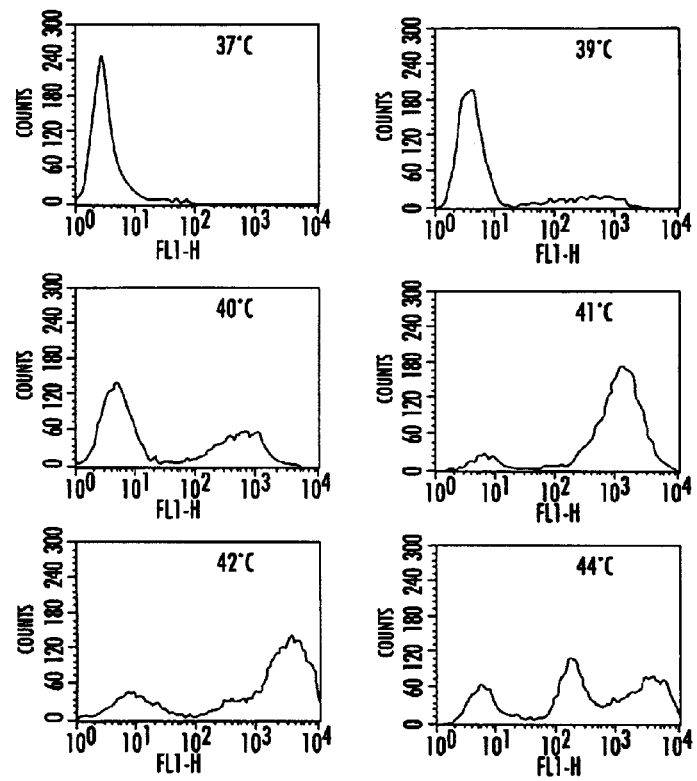
FIGS. 5A–5C present fluorescence micrographs and graphs of flow cytometry analysis that demonstrate the induction kinetics of the hsp70B promoter.
Figure 5B:
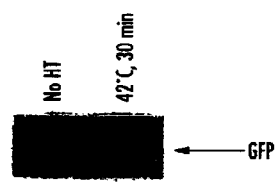

IV.A. Temperature Response and Kinetics of Heat-Induced Gene Expression In vitro A 400-bp promoter from the hsp70B promoter region (SEQ ID NO:13) Dreano et al. (1986) *Genes* 49:1–8; Voellmy et al. (1985) *Proc Natl Acad Sci USA* 82:4949–4953; Blackburn et al. (1992) *Cancer Res* 1358–1362) was chosen because its small size permitted the cloning of relatively large therapeutic genes in size-limited gene delivery vectors. The temperature response and induction kinetics of the hsp70B promoter was determined by assaying expression of reporter genes and levels of reporter gene products, as described in Example 5 (FIGS. 5A–5B).

Promoter activation was first observed at 39° C. and reached a peak level of 500–1000-fold GFP induction following heat treatment at about 42° C.–43° C. (gene induction at 43° C. is similar to that observed at 42° C.) (FIG. 5A). At 44° C., GFP expression dropped significantly. A careful examination indicated that most cells died within hours following this thermal exposure. The heat inducibility of the hsp70B promoter was also demonstrated in the B16F10 melanoma cell line. Western blot analysis of gene expression in heat-treated cells revealed a 27-fold induction of GFP protein (FIG. 5B). The difference in fold induction of GFP expression assayed by FACS analysis (500–1000-fold) versus Western blot analysis (27-fold) could reflect the nonlinear relationship between the amount of GFP protein and its fluorescence intensity.

Figure 5C:
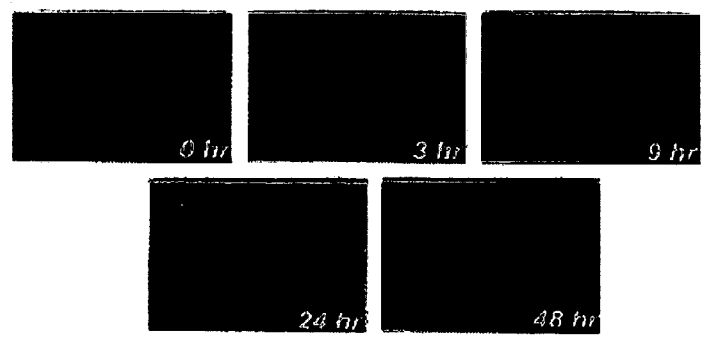

The kinetic profile of hsp70 activation in 4T1 and B16.F10 cells was determined by assessing GFP expression at multiple time points following heat provision as described in Example 6 (FIG. 5C). At 3 hours following hyperthermia treatment, GFP expression was observed to increase, and peak expression was observed at about 18–24 hours following heat exposure. GFP expression was reduced to background levels by 72 hours. Similar kinetics of hsp70 induction were observed in B16.F10 melanoma cells.

Figure 6:
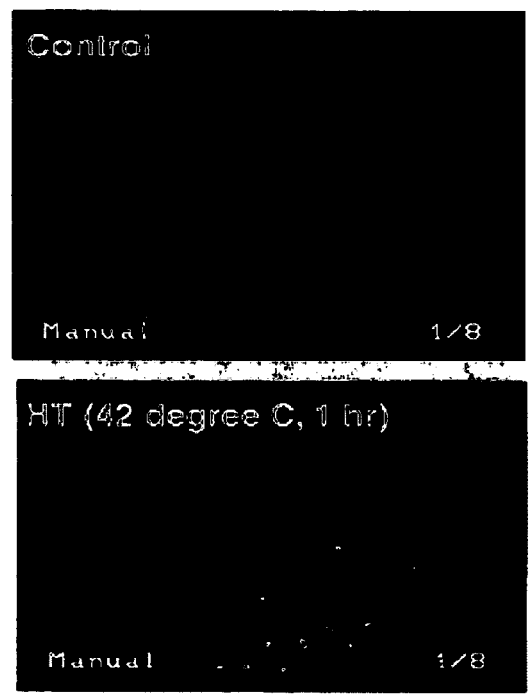
FIG. 6 shows fluorescence images of a feline sarcoma following intratumoral injection of AdhspGFP. GFP expression is observed as regions of white signal. Heat treatment of the sarcoma induced GFP expression (bottom panel), whereas GFP expression was not observed in control animals that did not receive a heat treatment (top panel).

The infectiveness and expression of AdhspGFP was also examined in a feline sarcoma model as described in Example 7. Consistent with observations in model murine tumors, intratumoral injection of AdhspGFP followed by heat treatment of the tumor induced GFP expression (FIG. 6). By contrast, GFP was not detected in non-heat treated control sarcomas (FIG. 6).

Figure 7:
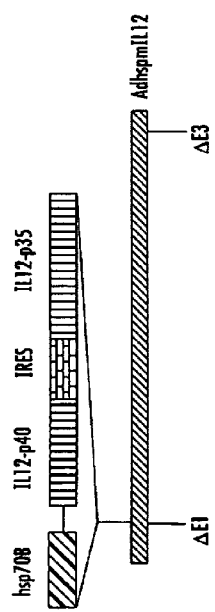
FIG. 7 is a diagram of the genetic structure of the recombinant adenovirus vector encoding the murine interleukin 12 gene. A murine hsp70B promoter is operatively linked to a nucleotide sequence encoding the IL12 p40 and p35 subunits. The coding regions for each subunit are separated by an IRES sequence. ΔE1 and ΔE3 identify represent deletions in E1 and E3 regions, respectively, of adenovirus that render the virus replication-deficient.

IV.B. Adenovirus-Mediated, Heat-Induced Expression of a Therapeutic Gene In vitro and In vivo To examine the efficacy of the heat-inducible gene therapy approach in experimental tumor models, two recombinant adenovirus vectors encoding the mouse IL12 gene and the human TNF-α gene under the control of the hsp70B promoter were constructed (AdhspmIL12 and AdhspTNFα, respectively). As an example, the genetic structure of AdhspIL12 is diagrammed schematically in FIG. 7. In this case, the hsp70B promoter is operatively linked to sequences encoding the IL12 p40 and p35 subunits, the coding regions separated by an IRES sequence.

The AdhspmIL12 and AdhspTNFα viruses were used to infect 4T1 mouse mammary adenocarcinoma cells and the resulting abundance of recombinantly produced TNF-α and IL12 was measured, as described in Example 7. Representative levels of TNF-α and IL12 are presented in Table 2.

Heat treatment caused the induction of TNF-α and IL12 to greater than $6.8 \times 10^5$-fold and greater than 13,600-fold over background, respectively, in infected cells. The non-heated control showed cytokine levels that were below detectable limits, similar to that observed for non-infected control cells. The non-heated and non-infected controls demonstrate the low leakiness of the hsp70B promoter.

For measurement of heat-inducible gene induction in vivo, the viral vectors were injected intratumorally into a mouse model of melanoma and animals were heat-treated as described in Example 8. Representative results are presented in Table 3. Heat treatment of tumors infected with AdhspTNF-α showed 835-fold induction of TNF-α. Heat treatment of tumors infected with AdhspmIL12 showed 33-fold induction of IL12. Non-heat treated cells infected with either virus showed cytokine levels comparable to control cells infected with an adenoviral vector encoding GFP, demonstrating the low leakiness of the hsp70B promoter in vivo.

TABLE 2

Heat-induced Gene Expression in Recombinant Adenovirus-Infected Cells in vitro measurement

| Adenovirus construct | no heat treatment | heat treatment 42° C. for 30 min | fold increase |
|---|---|---|---|
| AdhspTNF-α | <2 pg/ml | 1.85 µg/ml | >6.8 × 10$^5$ |
| AdhspIL-12 | <5 pg/ml | 68 ng/ml | >13,600 |

TABLE 3

Heat-Induced Gene Expression in Adenovirus-Infected Tumors in vivo measurement

| Adenovirus construct | no heat treatment | heat treatment 42.5° C. for 40 min | fold increase |
|---|---|---|---|
| AdhspTNF-α | 9.5 pg/g tumor | 7.94 ng/g tumor | 835 |
| AdhspIL-12 | 0.18 ng/g tumor | 6 ng/g tumor | 33 |

The observed levels of induction in vivo were lower than observed levels of gene induction in vitro, possibly as a result of the inaccessibility of many tumor cells to the virus. To support this explanation, tumors that had been injected with AdhspEGFP and heat treated to induce GFP expression were sectioned. This analysis revealed that only a small fraction of cells in the tumor mass, typically less than 5%, was infected by the virus. Despite the low infectivity rate, the observed induction of gene expression following heat treatment, clearly demonstrates the operability of the heat-inducible gene expression system in vivo.

The AdhspIL12 construct was also used to evaluate heat inducibility of a therapeutic gene in a feline subject. Intratumoral injections of AdhspIL12 were performed in feline sarcoma patients as described in Example 9. Similar to the results observed in mouse, levels of IL12 in the tumor tissue were below the sensitivity of detection (75 pg/g of tumor tissue) prior to heat treatment, and reached a peak level of 2700 pg/g of tumor tissue following heat treatment.

Figure 8:
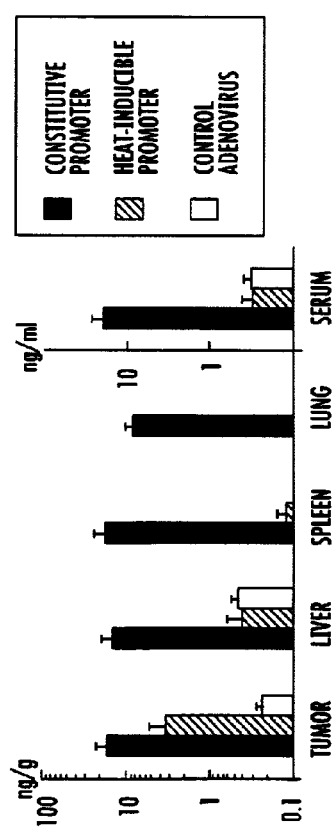
FIG. 8 is a graph depicting intratumoral (ng IL/g tumor) and systemic (ng IL/ml serum) levels of murine interleukin 12 (mIL12) after intratumoral vector injection. Intratumoral and systemic expression of murine interleukin 12 (mIL12) after intratumoral injection of either control adenovirus (AdGFP was used as a control in this experiment) (open bar), adenovirus constitutively expressing mIL12 (AdCMVIL12) (solid bar), or adenovirus expressing mIL12 controlled by a heat inducible promoter (AdhspIL12) combined with heat treatment in subcutaneous B16.F10 melanomas (hatched bar). The results are plotted as mean±standard error. Each data point represents results obtained from 2–4 animals.

Importantly, the gene therapy constructs and methods disclosed herein provide substantial intratumoral levels of IL12 and minimal serum levels of IL12. The utility of heat-inducible gene therapy vectors in restricting therapeutic gene expression to the tumor was assessed as described in Example 10. Adenovirus-mediated intratumoral expression of IL12 under the control of a heat inducible promoter in combination with hyperthermia is almost as effective in elevating IL12 levels when compared to heterologous expression using the strong constitutive promoter CMV (FIGS. 8 and 9). Heat-inducible IL12 expression further affords low serum levels of the transgene, while CMV-IL12 constructs produce deleterious serum levels of IL12 (FIGS. 8 and 9).

In addition to high inducibility by heat, many hsp promoters are also responsive to various intrinsic microenvironmental stresses such as hypoxia or oxidative free radicals. Stress exposure can induce stress gene promoter-controlled therapeutic gene expression in the tumor mass without the application of hyperthermia. For example, transient exposure to 1% hypoxia results can produce a 0.5–3-fold induction of gene expression (Dacha et al. (1997) Nature Med 3:515–520; Gazit et al. (1995) Cancer Res 55:1660–1663). Thus, tumor-specific stimuli can synergize with heat exposure to amplify gene expression.

V. Gene Therapy in Animal Models

V.A. Adenovirus-mediated, Hyperthermia-Controlled Gene Therapy

Figure 10:
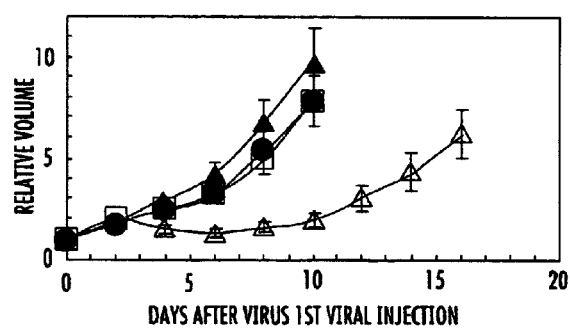
FIG. 10 is a graph that depicts tumor growth delay conferred by adenovirus-mediated, hyperthermia-controlled gene therapy. Experimental tumors were established in syngeneic C57BL/6 black mice by implanting $10^6$ tissue cultured B16.F10 melanoma cells. Viral injections were performed 1 week later, when the tumor had grown to 5–7 mm in diameter. (●) mice injected with adenovirus encoding heat-inducible EGFP, no heat treatment; (□) mice injected with adenovirus encoding heat-inducible EGFP, heat treated; (▲) mice injected with heat-inducible IL12, no heat treatment; (Δ) mice injected with heat-inducible IL 12, heat treated.

The efficacy of the heat-inducible cancer gene therapy approach was tested using the AdhspIL12 virus in an animal model of tumor growth, as described in Example 11. Briefly, the B16F10 melanoma tumor cell line grown in syngeneic C57BL/6 mice was used as the tumor model. AdhspIL12 virus was injected in combination with moderate hyperthermia treatment comprising a first heat treatment at 42.5° C. for 40 minutes, followed by a second identical heat treatment 7 days later. Animals receiving such injections and heat treatments displayed inhibited tumor growth (FIG. 10). By contrast, control animals receiving injections of AdhspIL12 in the absence of heat treatment showed tumor growth at a comparable rate to control animals receiving injections of AdhspEGFP, with or without heat treatment (FIG. 10). Immunohistological analysis of slow-growing tumors indicated the existence of a central necrotic area of the tumor that was devoid of blood vessels. This necrotic area was not observed in tumors from control animals. Thus, heat-inducible IL12 adenovirus is effective in controlling the growth of the B16F10 melanoma in C57BL/6 mice.

V.B. Plasmid-Mediated Gene Therapy

The anti-tumor effect of plasmid gene therapy vectors, when administered in conjunction with electroporation was tested in a mouse melanoma model, as described in Example 12. Administration of plasmid gene therapy vectors encoding murine IL2 or murine IL12 resulted in significant tumor growth delay (FIG. 11). Electroporation in conjunction with control plasmid (pEGFP-N1) did not result in significant growth delay compared to control plasmid alone or non-treated controls. In addition, injections of naked mIL2 or mIL12 plasmid alone did not result in any significant growth delay compared to control plasmid. The combination of electroporation with either mIL2 or mIL12 plasmid resulted in a significant growth delay of approximately 5–15 days when compared to both control plasmid plus electroporation (p<0.01) and the respective naked cytokine plasmids (p<0.05), with mIL12 plus electroporation being the most effective. These experiments were conducted three times to ensure the reproducibility of the experiments. In all three experiments, a similar pattern of tumor growth delays was observed.

VI. Tumor Growth Delay Following Combined Gene Therapy and Radiation Treatment

Disclosed herein are methods for combining radiation and gene therapy treatments. Radiotherapy followed by intratumoral injection of an adenovirus the constitutively expression IL12/B7.1 resulted in significantly more tumor growth delay than radiation or gene therapy alone in two murine tumor models.

VI.A. Combined Radiotherapy and Constitutive Gene Expression Treatments

The therapeutic effect of combined radiation treatment and gene therapy was examined. One possible outcome of combined treatment was that radiotherapy could enhance or potentiate expression of the therapeutic gene. Alternatively or in addition, combined radiation and gene therapy treatments could provide increased beneficial effect by separate mechanisms for promoting tumor regression.

To determine whether ionizing radiation can enhance expression of an adenovirus construct, levels of IL12 were measured up to day 9 after AdIL12/B7.1 injection with or without immediate exposure to ionizing radiation (18 Gy). No significant difference in IL12 expression profiles was detected between the two groups of animals. In both groups, the level of IL12 in the tumor was negligible at 9 days post-injection, indicating that the combination of AdIL12/B7.1 injection and exposure to ionizing radiation did not result in prolonged transgene expression. Although IL12 expression was not enhanced by radiotherapy, the combined treatment provided increased therapeutic value compared to gene therapy or radiation treatment alone, as described herein below.

Figure 12A:
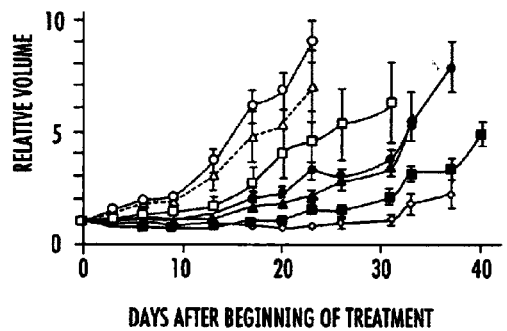
FIG. 12A presents a graph depicting mean relative volumes (±standard error) for different combinations of radiotherapy and adenovirus gene therapy in 4T1 tumors in Balb/c mice. (Δ) untreated control; (○) injection of AdGFP on day 7 after transplantation, no radiotherapy; (□) injection of AdIL12/B7.1 on day 7 after transplantation, no radiotherapy; (●) initiation of radiotherapy on day 7 after transplantation, injection of AdGFP after the last (third) radiotherapy fraction; (■) initiation of radiotherapy on day 7 after transplantation, injection of AdIL12/B7.1 after the first radiotherapy fraction; (◇) initiation of radiotherapy on day 7 after transplantation, injection of AdIL12/B7.1 after the last (third) radiotherapy fraction; (▲) injection of AdIL12/B7.1 on day 7 after transplantation, initiation of radiotherapy on day 9 after transplantation. The virus dose injected was $3 \times 10^8$ pfu in 50 µl PBS, except for the injection after the third radiation fraction when $3 \times 10^7$ pfu were used.
Figure 12B:
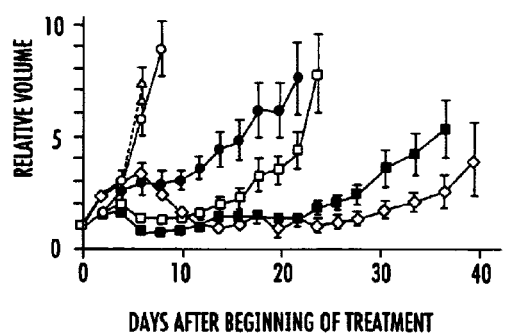
FIG. 12B presents a graph depicting mean relative volumes (±standard error) for different combinations of radiotherapy and adenovirus gene therapy in B16.F10 tumors in C57BL/6 mice. (Δ) untreated control; (○) injection of AdGFP on day 7 after transplantation, no radiotherapy; (□) injection of AdIL12/B7.1 on day 7 after transplantation, no radiotherapy; (●) initiation of radiotherapy on day 7 after transplantation, injection of AdGFP after the last (third) radiotherapy fraction; (■) initiation of radiotherapy on day 7 after transplantation, injection of AdIL12/B7.1 after the first radiotherapy fraction; (◇) initiation of radiotherapy on day 7 after transplantation, injection of AdIL12/B7.1 after the last (third) radiotherapy fraction; (▲) injection of AdIL12/B7.1 on day 7 after transplantation, initiation of radiotherapy on day 9 after transplantation. The virus dose injected was $3 \times 10^8$ pfu in 50 µl PBS.
Figure 13A:
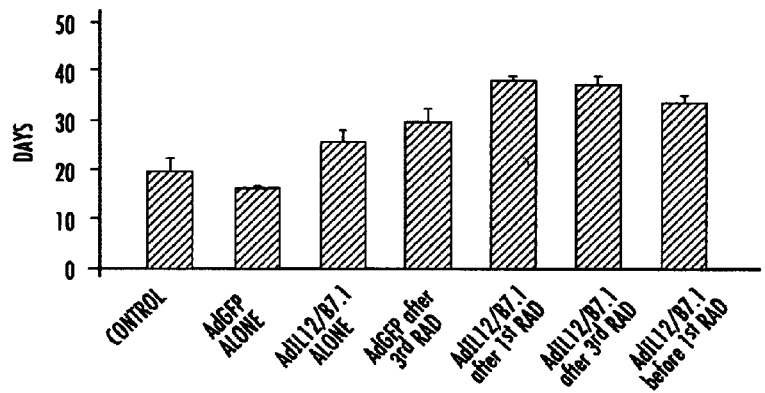
FIG. 13A is a graph depicting the number of days (mean±standard error) for tumor growth to four times tumor volume at the time of initial treatment for the indicated different combinations of radiotherapy (RAD) and adenovirus gene therapy in 4T1 tumors in Balb/c mice. Bars from left to right, control, AdGFP administered without radiation treatment, AdIL12/BL7.1 administered without radiation treatment, AdGFP injection after third radiation treatment, AdIL12/B7.1 injected after first radiation treatment, AdIL12/B7.1 injected after third radiation treatment, AdIL12/B7.1 injected before first radiation treatment.
Figure 13B:
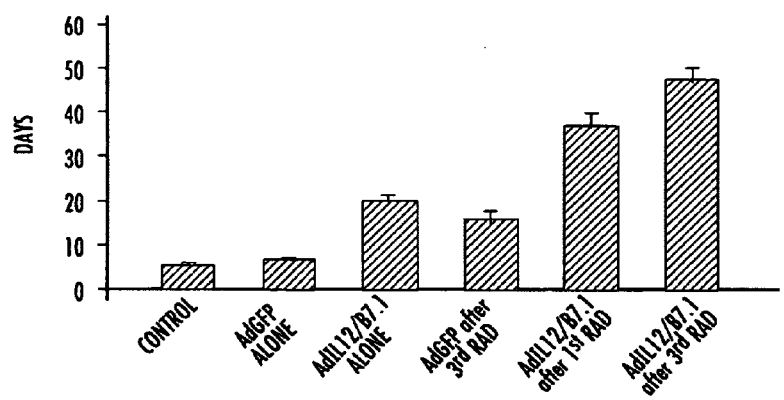
FIG. 13B is a graph depicting the number of days (mean±standard error) for tumor growth to four times tumor volume at the time of initial treatment for the indicated different combinations of radiotherapy (RAD) and adenovirus gene therapy in B16.F10 tumors in C57BL/6 mice. Bars from left to right, control, AdGFP administered without radiation treatment, AdIL12/BL7.1 administered without radiation treatment, AdGFP injection after third radiation treatment, AdIL12/B7.1 injected after first radiation treatment, AdIL12/B7.1 injected after third radiation treatment.

The anti-tumor effect of combined adenoviral-mediated gene therapy and radiation treatment was assessed in 4T1 tumors in Balb/c mice and B16.F10 tumors in C57BL/6 mice, as described in Example 13. Tumor volume and growth rate were reduced in response to radiotherapy alone, and this reduction was enhanced by adenovirus-mediated IL12/B7.1 gene expression (FIGS. 12 and 13). AdGFP was injected as a control and did not cause growth delay in either tumor model. Exposure to ionizing radiation and AdGFP injection resulted in a distinct, statistically significant ($P<0.01$) growth delay of tumors compared to control tumors injected with AdGFP and not exposed to ionizing radiation. AdIL12/B7.1 injection alone caused significant growth delay in both tumor models. All combination treatments, with the exception of the 4T1 group in which radiotherapy was initiated 2 days after virus injection, were significantly ($P<0.05$ for 4T1 and $P<0.01$ for B16.F10) more effective to radiation plus AdGFP injection. For both models, intratumoral injection of AdIL12/B7/1 immediately after the last radiation fraction was more effective than any other treatment schedule, especially when compared with the addition of AdIL12/B7.1 after the first fraction or with postponement of radiotherapy to 2 days after virus injection. The most effective treatment in 4T1 bearing Balb/c mice included radiotherapy and injection of a 10-fold reduced dose of AdIL12/B7.1, supporting a synergistic effect of the combined treatment. Although several complete regression responses were observed, all tumors eventually regrew.

The combined treatments were generally tolerated without any increase in local toxicity (skin reaction) as assessed by inspection. However, animals receiving both radiotherapy and AdIL12/B7.1 injection displayed systemic toxicity during the first week following virus injection, including symptoms of weight loss and apathy. Symptoms were substantially absent (>90%) after 1 week. Animals injected with AdIL12/B7.1 also showed splenomegaly (mean splenic weight of 0.7 g in AdIL12/B7.1 injected compared to 0.07 g in uninjected animals).

VI.B. Combined Radiotherapy and Heat-Inducible Gene Expression Treatments

Figure 14:
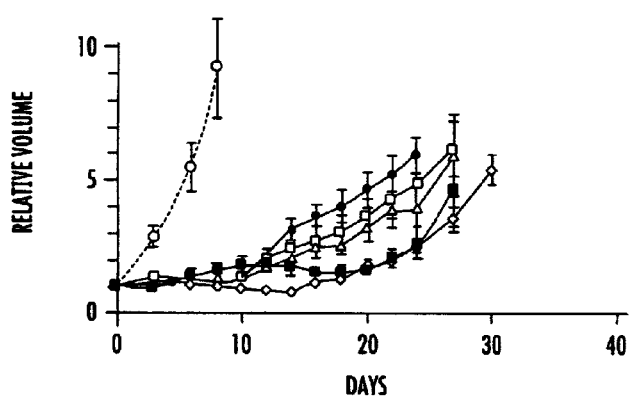
FIG. 14 is a graph depicting enhanced tumor growth delay when both radiation and gene therapy treatments are employed as described in Example 13. Relative tumor volumes (±standard error) following various therapeutic regimens are shown: (○) injection of AdGFP; (●) injection of AdGFP 24 hours prior to last radiation fraction, no anesthesia, no heat treatment; (Δ) injection of $3 \times 10^8$ pfu AdhspIL12 prior to third radiation fraction, anesthesia, heat treatment at 34° C. 24 hours after virus injection; (□) injection of AdGFP 24 hours prior to third radiation fraction, anesthesia, heat treatment at 42.5° C. 24 hours after virus injection; (◇) injection of AdhspIL12 24 hours prior to third radiation fraction, anesthesia, heat treatment at 42.5° C. 24 hours after virus injection; (■) injection of AdhspIL12 3 days prior to third radiation treatment, anesthesia, heat treatment at 42.5° C. 24 hours after virus injection.
Figure 15:
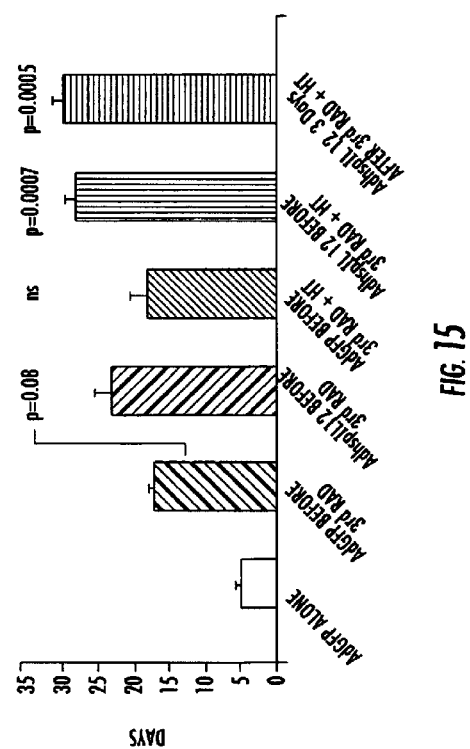
FIG. 15 is a bar graph that illustrates enhanced tumor growth delay when both radiation and gene therapy treatments are employed as described in Example 14. The indicated groups were treated with radiotherapy and/or heat-inducible adenovirus-mediated gene therapy in B16 tumors, and the time required for growth of the tumor to 3-fold its initial volume was calculated. P values above columns were derived by comparison with animals injected with AdGFP prior to the third radiation treatment. HT, heat treatment; RAD, radiotherapy; bars from left to right, control, AdGFP administered without radiation treatment, AdGFP injected before third radiation treatment, AdhspIL12 injected before third radiation treatment, AdGFP injected before third radiotherapy and heat treatment, AdhspIL12 injected before third radiotherapy and heat treatment, AdhspIL12 injected and heat treated three days after third radiotherapy.

Hyperthermia can be used as an adjuvant for radiation and chemotherapy, and thus the combined effect of fractionated radiotherapy, hyperthermia, and heat-inducible gene therapy was studied as described in Example 14. Briefly, hyperthermia-regulated gene therapy was tested in a non-immunogenic B16.F10 melanoma line that is syngeneic with C57BL/6 mice. For hyperthermic gene therapy, an adenoviral vector encoding 1L12 under the control of the human hsp70B promoter was used. One week after transplantation of B16.F10 cells (tumor dimension approximately 5–7 mm in diameter), tumors were exposed to ionizing radiation three times (Monday-Wednesday-Friday) with 11 Gy. Adenovirus was injected at $3\times10^8$ pfu/tumor 24 hours prior to the last radiation fraction or 3 days following the last radiation fraction. Hyperthermia was performed 24 hours later at 42.5° C. Growth delay was assessed in terms of the time required to triple initial tumor volume. The response to radiotherapy was improved when combined with heat-inducible gene therapy without apparent systemic toxicity (FIGS. 14 and 15).

VII. Factors Contributing to IL12 Anti-tumor Activity

To decipher the mechanisms of the anti-tumor effects observed following the treatment regimens disclosed herein, several experiments assessed the role of immune cells in promoting IL12 or IL2 therapeutic activity. The evaluation of biological changes that mediate IL12 immunotherapy assists in predicting the efficacy of the treatment and in determining recovery progress during treatment.

VII.A. Immunization Studies

Figure 16:
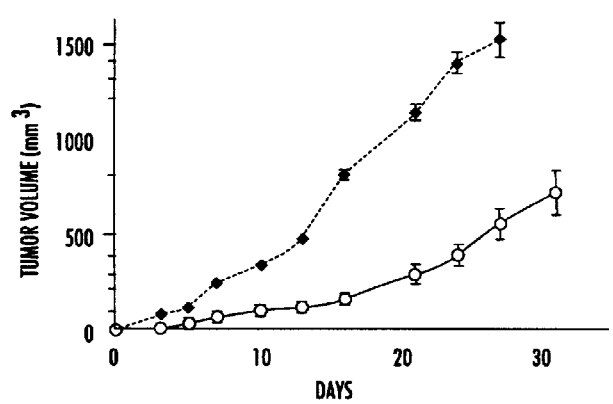
FIG. 16 is a graph depicting tumor growth after transplantation of $10^6$ vital, wild type 4T1 tumor cells in immunized mice. Immunizations were performed once in each of three consecutive weeks by subcutaneous injection with lethally irradiated 4T1 cells that were either (♦) unmanipulated or (○) infected with AdIL12/B7.1 (group means±SE).

4T1 cells infected with AdIL12/B7.1 and control non-infected cells were used to immunize mice as described in Example 15. When challenged with $10^6$ untreated 4T1 cells 1 week after the last of three weekly immunizations, animals immunized with AdIL12 infected cells showed a significant tumor growth delay compared to animals immunized with control cells (FIG. 16). This result indicates that immunological memory (possibly CTL activity, although no CTL assay was performed in this case) was stimulated by the AdIL12/B7.1 infected 4T1 cells.

VII.B. Gene Therapy in Mice Lacking T Cells

To address the role of T cells in IL12 gene therapy, experiments were carried out in nude mice bearing 4T1 or B16.F19 tumors as described in Example 16. Both tumor lines grew faster than in their respective syngeneic hosts (FIG. 17), consistent with a role of T cells in delaying tumor growth even in those formally non-immunogenic tumor models. In both B16.F10 and the 4T1 lines, the injection of AdIL12/B7.1 still resulted in significant growth delay ($P<0.05$) when compared to AdGFP injection. Although not unequivocally assessable because of the difference in tumor growth rate between immunocompetent and nude animals, the effect, however, seemed to be diminished in nude mice when compared to immunocompetent mice (FIG. 17). The growth delay effect was especially pronounced in 4T1, where even the treatment group grew faster than the control in immunocompetent mice. Viral injection caused a more pronounced growth delay in B16.F10. As the absence of T cells did not completely abolish the effects of the adenovirus in either group, a further group was employed comprising nude mice that had been depleted of NK cells using an anti-NK antibody. NK-depletion in nude mice further reduced the therapeutic effect of AdIL12/B7.1 in B16.F10 significantly ($P<0.05$). However, the therapeutic benefit is still not completely abolished. In 4T1 melanomas, there also appears to be a further reduction in growth delay, the statistical significance of which is unclear ($P=0.07$). Therefore, it appears that both T cells and NK cells play important roles in AdIL12/B7.1 mediated tumor growth delay for B16.F10 melanomas, but neither T cells nor NK cells are completely accountable for the total effect. While depletion of both T and NK abolished the therapeutic effects in the 4T1 model, it did not completely abolish the therapeutic effects in the B16.F10 model.

VII.C. CTL Assays

Figure 18:
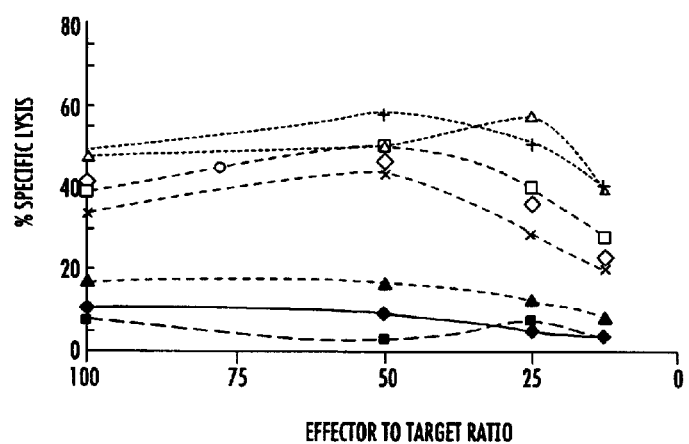
FIG. 18 is a graph depicting percentage specific lysis response of splenocytes from differently treated, B16.F10 tumor-bearing C57 mice against B16.F10, Tramp, or YAC1 cells. (solid line without symbol), (x), (+), splenocytes of untreated control animals against B16.F10 (solid line without symbol), Tramp (X), or YAC1 (+); (◇), (□), (Δ), splenocytes of animals injected intratumorally with AdGFP against B16.F10 (◇), Tramp (□), or YAC1 (Δ); (♦), (■), (▲), splenocytes of animals injected intratumorally with AdIL12/B7.1 against B16.F10 (♦), Tramp (■), or YAC1 (▲).

To further address the role of T and NK cells, CTL assays were conducted using splenocytes from AdIL12/B7.1 treated, syngeneic tumor bearing mice, as described in Example 17. The splenocytes were incubated with irradiated tumor cells for restimulation and subsequently tested for CTL activities against the tumor cells using the $^{51}$chromium ($^{51}$Cr) release assay. Although T-cells were necessary for maximum IL12 therapeutic effects, neither lymphocyte proliferation nor CTL response could be detected against naive B16.F10 or 4T1 tumor cells in animals bearing the respective tumors 7 days after in control or AdIL12/B7.1 treated mice if IL2 is not added to the restimulation process. When IL2 was added during the restimulation (FIG. 18), splenocytes of B16.F10 tumor bearing C57BL/6 mice from control and AdGFP injected animals proliferated and showed activity against B16.F10 cells. However, the activity was also observed against Tramp-C cells (Foster et al. (1997) *Cancer Res* 57:3325–3330), a prostate carcinoma line syngeneic with C57BL/6 and Yac-1 (an NK- and LAK-sensitive cell line) in splenocytes from the C57BL/6 mice, thus implicating nonspecific LAK activity instead of cell specific cytotoxic T-cell response. Interestingly, splenocytes from AdIL12/B7.1 injected C57BL/6 mice bearing B16.F10 showed no response (neither proliferation, nor any CTL activity) with or without IL2 addition, indicating a suppressive rather than the expected stimulatory effect on T cells by the IL12/B7.1 treatment (FIG. 18). One indication of immune activity against melanocyte antigens, depigmentation, was observed in AdIL12/B7.1 treated C57BL/6 mice, mainly locally. In a few cases mild depigmentation was also noticed several weeks after treatment at distant sites.

VII.D. Angiogenesis Activity

Figure 19A:
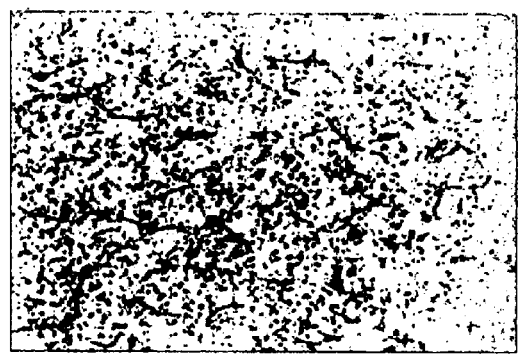
FIG. 19A is a photomicrograph (25× magnification) depicting a central region of a B16.F10 melanoma treated by intratumoral injection of the control vector AdGFP. The tumor tissue has been stained with an anti-collagen IV antibody to detect blood vessels, and an extensive network of blood vessels is observed as a dark staining product precipitate.
Figure 19B:
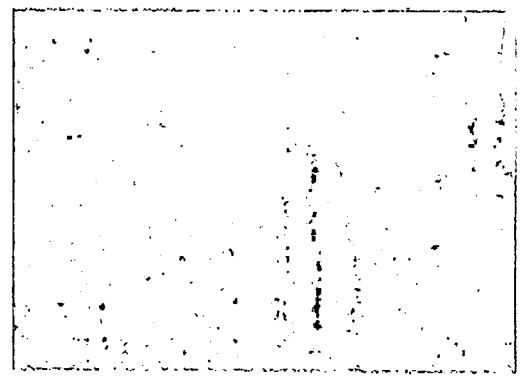
FIG. 19B is a photomicrograph of a center region of a tumor treated by intratumoral injection of AdIL12/B7.1. The tumor tissue has been stained with an anti-collagen IV antibody to detect blood vessels. Blood vessels are notably absent (fewer regions of dark staining product precipitate), and tumor necrosis is evidenced by the disrupted tissue morphology.

As IL12 has also been indicated to possess potent anti-angiogenesis effects (Voest et al. (1995) *J Natl Cancer Inst* 87:581–586; Coughlin et al. (1998) *J Clin Invest* 101: 1441–1452), vascular density was examined in B16 tumors that were treated with AdIL12/B7.1, as described in Example 18. Frozen sections of B16.F10 tumors 7 days after treatment with either AdGFP or AdIL12/B7.1 were stained with hematoxylin-eosin or with an antibody against collagen IV to detect blood vessels (Guffrey et al. (1995) *J Cutan Pathol* 22:122–127). AdGFP treated tumors showed an even distribution of vessel density throughout the tumor (FIG. 19A). By contrast, AdIL12/B7.1 treated tumors showed central necrosis with substantially reduced vessels centrally compared to AdGFP-treated tumors (FIG. 19B). Similar results were observed when an anti-CD13 antibody was used to detect blood vessels. These results indicate that anti-angiogenic activity can play a role in the observed anti-tumor effects of the viral construct.

VIII. Gene Therapy Methods

A therapeutic method according to the present invention comprises administering to a subject in need thereof a gene therapy construct. Preferably, the gene therapy construct encodes a polypeptide having an ability to elicit both an immune response and an anti-angiogenic response.

VIII.A. Therapeutic Applications

The therapeutic methods of the present invention are relevant to disorders that are caused by or exacerbated by unregulated angiogenesis or cell growth. For example, the disclosed gene therapy constructs can be useful in the treatment of both primary and metastatic solid tumors and carcinomas of the breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries, choriocarcinoma and gestational trophoblastic disease; male genital tract including prostate, seminal vesicles, testes and germ cell tumors; endocrine glands including thyroid, adrenal, and pituitary; skin including hemangiomas, melanomas, sarcomas arising from bone or soft tissues and Kaposi's sarcoma; tumors of the brain, nerves, eyes, and meninges including astrocytomas, gliomas, glioblastomas, retinoblastomas, neuromas, neuroblastomas, Schwannomas and meningiomas; solid tumors arising from hematopoietic malignancies such as leukemias and including chloromas, plasmacytomas, plaques and tumors of mycosis fungoides and cutaneous T-cell lymphoma/leukemia; lymphomas including both Hodgkin's and non-Hodgkin's lymphomas.

The compositions of the present invention can also be useful for the prevention of metastases from the tumors described above either when used alone or in combination with radiotherapy and/or other chemotherapeutic treatments conventionally administered to patients for treating angiogenic diseases. For example, a tumor can be treated conventionally with surgery, radiation or chemotherapy followed by administration to extend the dormancy of micrometastases and to stabilize and inhibit the growth of any residual primary tumor.

The invention also pertains to administration of the disclosed gene therapy vector to individuals at enhanced risk of cancer due to familial history or environmental risk factors.

The gene therapy constructs of the present invention can also be used in the treatment of angiogenic and proliferative disorders such as abnormal neovascularization conditions of the eye; skin diseases including psoriasis; blood vessel diseases including hemagiomas and capillary proliferation within atherosclerotic plaques; Osler-Webber Syndrome; myocardial angiogenesis; plaque neovascularization; telangiectasia; hemophiliac joints; angiofibroma; wound granulation; diseases characterized by excessive or abnormal stimulation of endothelial cells including intestinal adhesions, Crohn's disease, atherosclerosis, scleroderma and hypertrophic scars (i.e. keloids); and diseases which have angiogenesis as a pathologic consequence including cat scratch disease (Rochele minalia quintosa) and ulcers (*Helicobacter pylori*).

The heat-inducible gene therapy vectors of the present invention are also useful for treating any condition that could benefit from the biological properties of IL12 or IL2. In one embodiment, the condition to be treated is a proliferative or angiogenic disorder. IL12 displays anti-tumor activity when evaluated in murine models representing a variety of carcinomas, sarcomas, melanomas, and lymphomas, although systemic activity limits the usefulness of existing vectors. See Melero et al. (2001) *Trends Immunol* 22(3):113–115, and references cited therein. The present invention provides heat-inducible expression of IL12 to treat a similar broad spectrum of IL12-responsive cancers, as well as other proliferative or angiogenic disorders, with minimal systemic toxicity.

The heat-inducible gene therapy vectors of the present invention are also useful for treating any condition that could benefit from the biological properties of IL12 or IL2 activity, such as the anti-proliferative or anti-angiogenic activity of IL12, wherein the condition is not a disease or disorder. For example, a gene therapy construct of the present invention can be used as a birth control agent that inhibits ovulation and establishment of the placenta.

VIII.B. Subjects

The subject treated in the present invention in its many embodiments is desirably a human subject, although it is to be understood that the principles of the invention indicate that the invention is effective with respect to invertebrate and to all vertebrate species, including mammals, which are intended to be included in the term "subject". Moreover, a mammal is understood to include any mammalian species in which treatment or prevention of cancer or infectious diseases is desirable, particularly agricultural and domestic mammalian species.

The methods of the present invention are particularly useful in the treatment of warm-blooded vertebrates. Thus, the invention concerns mammals and birds.

More particularly, contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

VIII.C. Formulation

The gene therapy constructs and cells of the present invention preferably comprise a pharmaceutical composition that includes a pharmaceutically acceptable carrier. Any suitable pharmaceutical formulation can be used to prepare the gene therapy constructs for administration to a subject.

For example, suitable formulations can include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some preferred ingredients are SDS, for example in the range of 0.1 to 10 mg/ml, preferably about 2.0 mg/ml; and/or mannitol or another sugar, for example in the range of 10 to 100 mg/ml, preferably about 30 mg/ml; and/or phosphate-buffered saline (PBS).

It should be understood that in addition to the ingredients particularly mentioned above the formulations of this invention can include other agents conventional in the art having regard to the type of formulation in question. Of the possible formulations, sterile pyrogen-free aqueous and non-aqueous solutions are preferred.

The therapeutic regimens and pharmaceutical compositions of the invention can be used with additional adjuvants or biological response modifiers including, but not limited to, the cytokines IFN-α, IFN-γ, IL2, IL4, IL6, TNF, or other cytokine affecting immune cells. In accordance with this aspect of the invention, the disclosed gene therapy construct can be administered in combination therapy with one or more of these cytokines.

VIII.D. Administration

Suitable methods for administration of a gene therapy construct of the present invention include but are not limited to intravenous, subcutaneous, or intratumoral injection. Alternatively, a gene therapy construct can be deposited at a site in need of treatment in any other manner, for example by spraying a composition comprising a gene therapy vector within the pulmonary pathways. The particular mode of administering a therapeutic composition of the present invention depends on various factors, including the distribution and abundance of cells to be treated, the vector employed, additional tissue- or cell-targeting features of the vector, and mechanisms for metabolism or removal of the vector from its site of administration. For example, relatively superficial tumors are preferably injected intratumorally. By contrast, tumors that are relatively inaccessible to injection are preferably treated by intravenous injection.

Preferably, the method of administration encompasses features for regionalized vector delivery or accumulation at the site in need of treatment. In one embodiment, a gene therapy vector is delivered intratumorally. When employing intratumoral delivery, the gene therapy construct preferably comprises a viral vector, or more preferably a plasmid.

In another embodiment, selective delivery of a gene therapy construct to a tumor is accomplished by intravenous injection of the construct in combination with hyperthermia pre-treatment as described in Example 19. See also Kong et al. (2001) *Cancer Research* 61:3027–3032). Briefly, a range of temperatures (34° C.–42° C.) and hyperthermia treatment scheduling (the time between hyperthermia and drug administration) were considered for their effect on extravasation of nanoparticles (e.g., liposomes or viral vectors) from tumor vasculature in a human tumor model. Under normothermic conditions (34° C.) and at 39° C., nanoparticles were unable to extravasate into the tumor interstitium. At 40° C.–42° C., nanoparticle extravasation increased with temperature, reaching maximal extravasation at 42° C. Temperatures higher than 42° C. led to hemorrhage and stasis in tumor vessels. Enhanced nanoparticle extravasation was observed several hours after heating, and the effect was minimal at 6 hours post-heating. Hyperthermia did not enable nanoparticle extravasation from normal vasculature. These experiments indicate that hyperthermia can enable and augment delivery of gene therapy vectors to tumors, and potentially help target such vectors specifically to tumors.

Thus, the disclosed methods can further comprise pre-heating the tumor prior to intravenous administration of the construct to facilitate delivery of the construct. Preferably, the pre-heating is performed about 0–4 hours, and more preferably about 0–2 hours, prior to administering the construct. Preferably, the heating comprises an increase in intratumoral temperature to about 40° C.–42° C., and more preferably about 42° C. Heating can be accomplished by any suitable technique as described herein below under the heading *Methods for Heat Induction of Gene Expression*. In this case, the tumor would also be heated subsequent to administration of the gene therapy construct to induce gene expression.

For delivery of gene therapy constructs to pulmonary pathways, gene therapy constructs of the present invention can be formulated as an aerosol or coarse spray. Methods for preparation and administration of aerosol or spray formulations can be found, for example, in Cipolla et al. (2000) *Hum Gene Ther* 11(2):361–371; U.S. Pat. Nos. 5,858,784; 6,013,638; 6,022,737; and 6,136,295.

VIII.E. Dose

An effective dose of a gene therapy composition of the present invention is administered to a subject in need thereof. A "therapeutically effective amount" is an amount of the therapeutic composition sufficient to produce a measurable response (e.g., an immunostimulatory or anti-angiogenic response in a subject being treated). In one embodiment, an activity that inhibits tumor growth is measured. Actual dosage levels of active ingredients in the pharmaceutical compositions of this invention can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved.

The potency of a therapeutic composition can vary, and therefore a "therapeutically effective" amount can vary. However, using the assay methods described herein below, one skilled in the art can readily assess the potency and efficacy of a candidate modulator of this invention and adjust the therapeutic regimen accordingly.

After review of the disclosure herein of the present invention, one of ordinary skill in the art can tailor the dosages to an individual patient, taking into account the particular formulation, method of administration to be used with the composition, and tumor size. Further calculations of dose can consider patient height and weight, severity and stage of symptoms, and the presence of additional deleterious physical conditions. Such adjustments or variations, as well as evaluation of when and how to make such adjustments or variations, are well known to those of ordinary skill in the art of medicine.

For local administration of viral vectors, previous clinical studies have demonstrated that up to $10^{13}$ pfu of virus can be injected with minimal toxicity. In human patients, $1\times10^9$–$1\times10^{13}$ pfu are routinely used. See Habib et al. (1999) *Human Gene Therapy* 12:2019–2034. To determine an appropriate dose within this range, preliminary treatments can begin with $1\times10^9$ pfu, and the dose level can be escalated in the absence of dose-limiting toxicity. Toxicity can be assessed using criteria set forth by the National Cancer Institute and is reasonably defined as any grade 4 toxicity or any grade 3 toxicity persisting more than 1 week. Dose is also modified to maximize anti-tumor and/or antiangiogenic activity. Representative criteria and methods for assessing anti-tumor and/or anti-angiogenic activity are described herein below.

VIII.F. Adoptive Immunotherapy

Adoptive immunotherapy refers to a therapeutic approach for treating cancer or infectious diseases in which immune cells are administered to a host with the aim that the cells mediate either directly or indirectly specific immunity to tumor cells and/or antigenic components or regression of the tumor or treatment of infectious diseases, as the case can be. Thus, a therapeutic composition of the present invention can comprise cells transformed with the disclosed gene therapy construct, for example cells comprising ex vivo, in vivo, and in vitro gene transfer systems. See e.g. Yang (1992) *Crit Rev Biotech* 12(4):335–356. Ex vivo gene transfer involves the procurement of cells from the patient, growth of such cells in culture. The gene therapy construct is transfected into the cells, the transfected cells are expanded to a population suitable size, and the expanded population is subsequently re-implanted in the patient. In vitro gene transfer is similar, although the derivation of the transformed cells is not particular to cells from a particular patient. These "laboratory cells" are transfected, and the transfected cells are selected and expanded to a population suitable for implantation into a patient. In vivo gene transfer involves introducing the DNA into the cells of the patient when the cells are within the patient. The methods for gene therapy using a gene therapy vector disclosed herein encompass in vivo, ex vivo, and in vitro gene transfer.

The cells can be of any type that is compatible with the recipient's immune system. As with any transplantation of cells or tissue, the major tissue transplantation antigens of the administered cells will match the major tissue transplantation antigens of the recipient's cells.

Preferably the cells administered are derived from a tumor of the intended recipient, e.g. tumor cells can be removed from the intended recipient, transformed or transfected as appropriate then returned, in order to effect cell therapy. Alternatively, they can be derived from other individuals with compatible tissue transplantation antigens, such as close relatives, Similarly, they can be HLA matched cells, e.g. HLA matched fibroblasts, which do not give rise to adverse immune reaction.

For the purposes of cell therapy, it is preferred to deliver the cells by intradermal or subcutaneous administration. A person of skill in the art will be able to choose an appropriate dosage e.g. the number and concentration of cells, to take into account the fact that only a limited volume of fluid can be administered in this manner.

VIII.G. Methods for Heat Induction of Gene Expression

The present invention provides methods for inducible gene expression using a gene therapy construct comprising an heat-inducible promoter. In a preferred embodiment of the invention, the heat-inducible promoter is a hsp70 promoter.

The hsp70 promoter is activated by a variety of external stimuli, including but not limited to thermal energy, radiative energy, photodynamic therapy, low frequency magnetic fields, toxins and other chemical compounds, and heavy metal ions. See Kiang & Tsokos (1998) *Pharmacol Ther* 80(2):183–201; Blank & Goodman (1999) *J Cell Biochem* 75(3):369–374; Luna et al. (2000) *Cancer Res* 60(6):1637–1644. Representative heat sources include but are not limited to heated water, as disclosed in Examples 8–11 and 14, focused ultrasound heating (International Publication No. WO 98/0684), or DC voltage (International Publication No. WO 99/42137). hsp70 activation by endogenous factors can occur at sites of physiological stress, for example, changes in intracellular pH or cyclic AMP, hypoxia/ischaemia, seizure, and hemorrhage. Development of a pathophysiological condition, for example a tumor, can create cell stress conditions. An endogenous mediator of the response is IFN-γ, which can activate hsp70 (Stephanou & Latchman (1999) *Gene Expr* 7(4–6):311–319). The gene therapy methods of the present invention can utilize hsp70 activation by any suitable method.

A preferred embodiment of the invention employs thermal treatment based on its efficacious and easily modulatable control of gene expression. Preferably, heat induction of gene expression comprises an increase in the temperature of the site in need of treatment to 39° C.–43° C., more preferably about 42° C.–43° C.

In a clinical setting, thermal treatment can be accomplished by any one of several methods. Most methods involve delivery of energy into the body, using either microwaves, ultrasound, radiofrequency, or radiant heat (infrared). Methods for delivery of hyperthermia are roughly broken down into the following categories: whole body hyperthermia, local hyperthermia and regional hyperthermia and interstitial hyperthermia. The methods for achieving these types of heating will be discussed separately herein below. Detailed descriptions of these methods are known to one of skill in the art. See Samulski (1999) in Hendee, ed., *Biomedical Uses of Radiation*, pp. 1133–1233, VCH Publishers, Weinheim, Germany.

For all hyperthermia applications, it is necessary to measure temperature of the site being heated. A brief description of the types of thermometry used is also discussed for individual methods herein below.

In brief, the distribution of temperatures achieved during hyperthermia treatment is variable, depending on the method used to deliver the treatment. The most uniform temperatures are achieved with whole body hyperthermia, but this method does not achieve a differential temperature between the tumor and the surrounding normal tissue. Typical variations throughout the body are about 0.5° C. (Thrall et al. (1986) *Cancer Res* 46(12 Pt 1):6229–6235). In some cases, uniform hyperthermia can nevertheless provoke a tumor-specific response. For example, as disclosed in Example 19, increased nanoparticle extravasation following hyperthermia occurs preferentially in tumor microvessels. Thus heating of normal tissue, in addition to heating of tumorous tissue, is acceptable. In other cases, local provision of heat is preferable and can be accomplished by the techniques described below. The temperature distributions that are achieved with methods of restricted heating are more variable. It is not unusual to see temperatures that range from 39° C. to nearly 50° C. in the same tumor. Thus, a method for heat treatment can be selected for a particular application, and parameters of the method (e.g., device, temperature, duration) can be tailored to achieve effective expression of the therapeutic gene.

Using such methods, tumors of the extremities and other sites, including ovary (Leopold et al. (1993) *Int J Radiat Oncol Biol Phys* 27:1245–1251), brain (Sneed et al. (1991) *Neurosurgery* 28:206–215), breast (Vernon et al. (1996) *Int J Radiat Oncol Biol Phys* 35:731–744), prostate (Anscher et al. (1997) *Int J Radiat Oncol Biol Phys* 37:1059–1065), and head and neck (Valdagni & Amicetti (1994) *Int J Radiat Oncol Biol Phys* 28:163–169), can be heated to a temperature range that is adequate for heat-inducible gene expression. Total body hyperthermia can be used for heat-induced gene therapy in any body region, in particular those tissues that are not amenable to local heating (e.g., pulmonary passages).

As disclosed herein, expression of the heat-inducible gene therapy constructs of the present invention is observed following heat treatment at temperatures 39° C. Thus, total body hyperthermia or regional heat provision at 39° C. is sufficient to induce expression of the disclosed gene therapy constructs. Thus, it will be understood that any suitable method for heat provision can be used in accordance with the methods of the present invention and that the method for heat provision is not a limitation of the method.

Total Body Hyperthermia. Total body hyperthermia is most commonly administered using radiant heating devices. These chamber type devices surround the entire body and emit infrared energy from their surface, which is absorbed in the superficial skin layers (Robins et al. (1985) *Cancer Res* 45(8):3937–3944. This energy is in turn transferred to the blood, which as it circulates, leads to an increase in total body temperature. Typically, a humidified chamber is used so that heat loss from evaporative cooling does not occur. Other devices that have been used for total body heating involve direct heat transfer through the skin. For example, external hot air or delivery of microwave energy can heat deeper portions of the body while minimizing evaporative cooling. The maximum total body temperature that can be safely reached when using these methods is 41.8° C. in humans. High temperature heating is usually restricted to a duration of 1–2 hours. However, a longer duration of heating at lower temperatures, for example heating at 41° C. for several hours, can also be employed (Toyota et al. (1997) *Int J Hyperthermia* 13(5):497–506; Repasky et al. (1999) *Infect Dis Obstet Gynecol* 7(1–2):91–97).

Thermometry for this type of heating is performed by simple placement of several skin sensors to monitor skin surface temperature. In addition, thermometers can be placed orally or intrarectally to monitor deep body temperature.

Local Hyperthermia. Local hyperthermia refers to heating tumors or other lesions that are typically less than 4–5 cm from the body surface. Tumors that fit into this category would be skin lesions, such as melanoma, squamous cell carcinoma, basal cell carcinoma, neck nodes resulting from head and neck cancer, and chest wall recurrences following breast cancer. Radiofrequency, microwave, and ultrasound applicators have been developed that are specifically designed for heating these types of tumors. Typically, the hyperthermia applicator is positioned immediately on top of the region of interest, and power is applied directly to the skin surface overlying the tumor. With these types of tumors, there is no attempt to focus power. Skin cooling is sometimes used to protect the skin. Local hyperthermia approximates tumor-specific heating in that there is predominantly tumorous tissue in the heated field, and occasionally a limited amount of normal tissue at the edge of the tumor.

In a case where local heat is applied, thermometry usually involves use of a fiber optic, or other specialized thermometer, that is transparent to microwave or radiofrequency power deposition. Thermometers are usually placed on the skin surface as well as into the tumor for monitoring deeper tissue temperature. Guidelines for thermometer placement have been set forth by the Radiation Therapy Oncology Group and by the European Society of Hyperthermic Oncology and are known to one of skill in the art. See Dewhirst et al. (1990) *Int J Radiat Oncol Biol Phys* 18(5):1249–1259 and Waterman et al. (1991) *Int J Radiat Oncol Biol Phys* 20(5):1099–1107.

Regional/Deep Hyperthermia. Regional hyperthermia refers to methods that deliver power to large portions of the body, such as a portion of the body where a tumor resides. Examples of tumors that fit into this category include tumors of the pelvis and abdomen, such as cancers of the rectum, cervix, prostate and ovary. Other examples include large tumors of the extremity, such as sarcomas and primary breast cancers. Radiofrequency, microwave, and ultrasound methods are also used for this type of heating, but require devices specifically designed for a particular application. For example, one method for heating the pelvis or abdomen uses a phased microwave array. This device delivers power from several antennas that are positioned circumferentially around the body. Power can be steered toward the region of interest by varying the phase and amplitude of each of the antennas in the array. Similarly, ultrasound devices can be designed to focus energy directly into deep lesions by using multiple beams that enter into the body from several positions.

Thermometry devices that are used to monitor regional heating are the same as those described herein above for superficial tumors, with the exception that guidelines for thermometer placement are different. Thermometry guidelines for regional heating methods are known in the art and can be found, for example, in Sapozink et al. (1991) *Int J Radiat Oncol Biol Phys* 20(5):1109–1115.

Interstitial/Intraluminal Hyperthermia. This type of hyperthermia is different from total body hyperthermia, local hyperthermia, and regional/deep hyperthermia, wherein the heating device is external to the tumor, in that the heating device is placed directly into the tumor. Radiofrequency, microwave and ultrasound devices have been designed for this type of application. Tumors that are located in hollow organs, such as the bladder, esophagus, and rectum are amenable to intraluminal hyperthermia, if the tumor is less than a few cm in size. Interstitial heating has been successfully applied to tumors of the brain, prostate, cervix, and other sites that are accessible for interstitial implants.

Thermometry guidelines are also available to direct monitoring when using interstitial/intraluminal devices and are known to one of skill in the art. See Emami et al. (1991) *Int J Radiat Oncol Biol Phys* 20(5):1117–1124.

VIII.H. Monitoring of Effects During Cancer Prevention and Immunotherapy

The effect of immunotherapy with a gene therapy construct of the present invention on development and progression of neoplastic diseases can be monitored by any methods known to one skilled in the art, including but not limited to measuring: 1) delayed hypersensitivity as an assessment of cellular immunity; 2) activity of cytolytic T-lymphocytes in vitro; 3) levels of tumor specific antigens, e.g., carcinoembryonic antigens (CEA); 4) changes in the morphology of tumors using techniques such as a computed tomographic (CT) scan; 5) changes in levels of putative biomarkers of risk for a particular cancer in individuals at high risk, and 6) changes in the morphology of tumors using a sonogram.

Delayed Hypersensitivity Skin Test. Delayed hypersensitivity skin tests are of great value in the overall immunocompetence and cellular immunity to an antigen. Inability to react to a battery of common skin antigens is termed anergy (Sato et al. (1995) *Clin Immunol Pathol* 74:35–43). Proper technique of skin testing requires that the antigens be stored sterile at 4° C., protected from light and reconstituted shortly before use. A 25- or 27-gauge needle ensures intradermal, rather than subcutaneous, administration of antigen. Twenty-four and forty-eight hours after intradermal administration of the antigen, the largest dimensions of both erythema and induration are measured with a ruler. Hypoactivity to any given antigen or group of antigens is confirmed by testing with higher concentrations of antigen or, in ambiguous circumstances, by a repeat test with an intermediate concentration.

Activity of Cytolytic T-lymphocytes In vitro. $8 \times 10^6$ peripheral blood derived T lymphocytes isolated by the Ficoll-Hypaque centrifugation gradient technique, are restimulated with $4 \times 10^4$ mitomycin C treated tumor cells in 3 ml RPMI medium containing 10% fetal calf serum. In some experiments, 33% secondary mixed lymphocyte culture supernatant or IL2, is included in the culture medium as a source of T cell growth factors.

In order to measure the primary response of cytolytic T-lymphocytes after immunization, T cells are cultured without the stimulator tumor cells. In other experiments, T cells are restimulated with antigenically distinct cells. After six days, the cultures are tested for cytotoxicity in a 4 hour $^{51}$Cr-release assay. The spontaneous $^{51}$Cr-release of the targets should reach a level less than 20%. For the anti-MHC class I blocking activity, a tenfold concentrated supernatant of W6/32 hybridoma is added to the test at a final concentration of about 12.5% (Heike et al. (1994) *J Immunotherapy* 15:165–174).

Levels of Tumor Specific Antigens. Although it can not be possible to detect unique tumor antigens on all tumors, many tumors display antigens that distinguish them from normal cells. Monoclonal antibody reagents have permitted the isolation and biochemical characterization of the antigens and have been invaluable diagnostically for distinction of transformed from nontransformed cells and for definition of the cell lineage of transformed cells. The best-characterized human tumor-associated antigens are the oncofetal antigens. These antigens are expressed during embryogenesis, but are absent or very difficult to detect in normal adult tissue. The prototype antigen is carcinoembryonic antigen (CEA), a glycoprotein found on fetal gut an human colon cancer cells, but not on normal adult colon cells. Since CEA is shed from colon carcinoma cells and found in the serum, it was originally thought that the presence of this antigen in the serum could be used to screen subjects for colon cancer. However, subjects with other tumors, such as pancreatic and breast cancer, also have elevated serum levels of CEA. Therefore, monitoring the fall and rise of CEA levels in cancer patients undergoing therapy has proven useful for predicting tumor progression and responses to treatment.

Several other oncofetal antigens have been useful for diagnosing and monitoring human tumors, e.g., alpha-fetoprotein, an alpha-globulin normally secreted by fetal liver and yolk sac cells, is found in the serum of subjects with liver and germinal cell tumors and can be used as a matter of disease status.

Computed Tomographic (CT) Scan. CT remains the choice of techniques for the accurate staging of cancers. CT has proved more sensitive and specific than any other imaging techniques for the detection of metastases.

Measurement of Putative Biomarkers. The levels of a putative biomarker for risk of a specific cancer are measured to monitor the effect of a gene therapy construct of the present invention. For example, in individuals at enhanced risk for prostate cancer, serum prostate-specific antigen (PSA) is measured by the procedure described by Brawer et al. (1992) *J Urol* 147:841–845 and Catalona et al. (1993) *JAMA* 270:948–958; or in individuals at risk for colorectal cancer CEA is measured as described above; and in individuals at enhanced risk for breast cancer, 16-α-hydroxylation of estradiol is measured by the procedure described by Schneider et al. (1982) *Proc Natl Acad Sci USA* 79:3047–3051. The references cited above are incorporated by reference herein in their entirety.

Sonogram. A Sonogram remains an alternative choice of technique for the accurate staging of cancers.

VIII.I. Monitoring of Anti-Angiogenic Activity during Gene Therapy

The anti-angiogenic activity of a gene therapy construct of the present invention can be monitored using a variety of techniques known to one of skill in the art, including but not limited to histological examination of blood vessels at the tumor site, quantitation of blood vessels in an implantable and extractable matrix gel (U.S. Pat. No. 5,382,514), detection of molecular markers associated with angiogenesis, for example vascular endothelial growth factor and the Tie receptor tyrosine kinase (U.S. Pat. Nos. 5,942,385 and 5,955,291), ultrasound estimation of blood volume (U.S. Pat. Nos. 6,059,727 and 5,860,929), and infared imaging that can resolve changes in vasculature (International Publication No. WO 00/78211).

EXAMPLES

The following Examples have been included to illustrate modes of the invention. Certain aspects of the following Examples are described in terms of techniques and procedures found or contemplated by the present co-inventors to work well in the practice of the invention. These Examples illustrate standard laboratory practices of the co-inventors. In light of the present disclosure and the general level of skill in the art, those of skill will appreciate that the following Examples are intended to be exemplary only and that numerous changes, modifications, and alterations can be employed without departing from the scope of the invention.

Materials and Methods Used in the Examples

Cell Culture. 4TI mouse mammary cancer cells were obtained from Dr. Fred Miller (Michigan Cancer Foundation of Detroit, Mich.). See Aslakson & Miller (1992) *Cancer Res* 52:1399–1405. B16F10 cells were obtained from American Type Culture Collection (Manassas, Va.). 293 cells (ATCC of Manassas, Va.) were used for adenovirus propagation. All cells were maintained in DMEM (Life Technologies, Inc. of Rockville, Md.) supplemented with 10% FBS (Hyclone of Logan, Utah) and 1 gram each of Penicillin/Streptomycin (Gibco/Life Technologies of Grand Island, N.Y. ). Cells were kept in a Forma cell culture humidity chamber (available from Global Medical Instrumentation, Inc. of St. Paul Minn.) at 37° C. with 5% $CO_2$.

Tumor Models. Tumors were formed by injecting $1 \times 10^6$ cells subcutaneously into a hind leg of C57BL/6 mice. Unless indicated otherwise, tumors were treated (injected or exposed to ionizing radiation) following tumor growth to a diameter of 5–7 mm in 7 days.

Adenoviral Vectors. The adenoviral vector AdIL12 (kindly provided by Dr. Frank L. Graham, McMaster University, Hamilton, Ontario, Canada) used in this study was described previously and is based on an Ad5 recombinant system (Pützer et al. (1997) *Proc Natl Acad Sci USA* 94:10889–10894). In short, both mIL12 subunit cDNAs were inserted in the E1 region and placed under control of the murine cytomegalovirus (MCMV) promoter. Efficient expression of both IL12 subunits was achieved by placing an internal ribosome entry site in between. Viruses were propagated in 293 cells and purified by CsCI-banding according to a standard protocol (Graham & Prevec (1995) *Mol Biotech* 3:207–220).

Heat-inducible adenoviral constructs were prepared using a set of commercially available plasmids (Microbix of Toronto, Canada) according to methods described by Graham & Prevec (1995) *Mol Biotech* 9:207–220. Briefly, the EGFP gene, a human TNF-α gene, and a murine IL12 gene were each cloned into the plasmid pDEsp1A such that the open reading frame of each gene was operatively linked to the hsp70B promoter (Dreano et al. (1986) *Genes* 49:1–8; Voellmy et al. (1985) *Proc Natl Acad Sci USA* 82:4949–4953). The EGFP gene was excised from the pEGFP-N1 plasmid (Clontech of Palo Alto, Calif.). The TNF-α gene was derived from plasmid pE4 (American Type Culture Collection) and the murine IL12 gene was derived from a plasmid obtained from the National Gene Vector Laboratory (University of Michigan of Ann Arbor, Mich.). The two subunits of IL12, p40 and p35, were cloned such that an internal ribosome entry site sequence (Morgan et al. (1992) *Nuc Acids Res* 20:1293–1299) was positioned between the open reading frames of p40 and p35. This vector construction enabled both IL12 subunits to be transcribed under the control of a same promoter. Recombinant adenovirus was obtained by co-transfection of pDEsp1A and pBHG10 into 293 cells according to the procedure described by Zhang et al. (1993) *Biotechniques* 15:868–872. After plaque purification, the virus was amplified in 293 cells to a titer of $0.5$–$3.0 \times 10^{11}$ pfu/ml and purified by CsCI-banding according to the method of Graham & Prevec (1995) *Mol Biotech* 3:207–220.

Plasmids. The pEGFP-N1 plasmid is obtained from the Clontech Corporation (Palo Alto, Calif.). It encodes the EGFP protein under the control of a cytomegalyvirus (CMV) promoter. Plasmid pNGVL-mIL2, and pNGVL-mIL12 were obtained from the National Gene Vector Laboratory (NGVL) at the University of Michigan, Ann Arbor, Mich. They encode murine IL2 and murine IL12 gene under the control of the CMV promoters respectively. Plasmid pNGVL-β-gal was also obtained from the NGVL. It encodes a nuclear targeted β-galactosidase (β-gal) gene under the control of the CMV promoter.

Histological Detection of β-galactosidase. Animals were anesthetized and sacrificed by cervical dislocation. Tumors injected with β-gal plasmid were fixed in 4% paraformaldehyde/PBS for 48 hours at 4° C. Tumors were sectioned at 250 µm. Sections were rinsed three times for thirty minutes each in rinse buffer (100 mM sodium phosphate, 2 mM $MgCl_2$, 0.01% deoxycholic acid and 0.02% NP-40) at room temperature. Sections were stained for 24 hours at room temperature. Staining solution comprised rinse buffer, 5 mM potassium ferricyanide, 5 mM potassium ferrocyanide and 1 mg/ml X-gal. After 24 hours, staining solution was removed and sections were stored in 70% ethanol before mounting (in 70% ethanol) for light microscopy.

Fluorescence Microscopy. EGFP fluorescence was visualized using a Zeiss Axioskop (Carl Zeiss, Inc. of Thornwood, N.Y.) equipped with Xenon-arc-lamp, a FITC filter, and optionally a 40 watt tungsten source for transillumination. Images were acquired with a color CCD camera and framegrabbing software.

FACS Analysis. FACS analysis and sorting were performed at the Flow Cytometry Shared Resource at the Comprehensive Cancer Center of Duke University Medical Center (Durham, N.C.). For analysis, a FACScan apparatus from Becton Dickinson (Franklin Lakes, N.J.) was used. For sorting, a FACScan Star Plus from Becton Dickinson (Franklin Lakes, N.J.) was used. Both apparatuses employed a cooled argon blue laser for excitation of the samples at 488 nm.

Western Blot Analysis. Western blot analysis of GFP levels was carried out according to the methods described by Li et al. (1995) *J Biol Chem* 270:4971–4974. Briefly, cells were lysed in a Petri dish containing a lysis buffer (50 mM Tris-HCl pH 7.4, 250 mM NaCl, 0.5% NP40, 50 mM NaF, 1 mM DTT, 1 mM phenylmehtylsulfonyl fluoride, 25 mg/ml aprotinin, 1 mM bezamide, and 10 mg/ml trypsin inhibitor, all materials from Sigma of St. Louis, Mo.). Lysed cells were centrifuges at 16,000×g for 5 minutes, and the supernatants were analyzed. About 60 mg of protein were loaded into each lane in a 12% polyacrylamide gel, electrophoresed, and blotted onto polyvinylidene diflouride membrane (Millipore of Bedford, Mass.).

Measurement of Cytokine Levels. Murine IL12 levels in serum samples and tumor extracts were detected with a mIL12 ELISA kit (R&D Systems of Minneapolis, Minn.) that detects the heterodimer of p35 and p40 (p75) with a detection level of 8 pg/ml. Serum was obtained from blood samples drawn from the tail vein before and at different time points until 9 days after intratumoral AdIL12 injection or plasmid injection with consecutive electroporation. For detection of intratumoral mIL12, untreated control tumors and tumors at different time points after infection or plasmid injection/electroporation were harvested. Tumors were homogenized in PBS (with COMPLETE® protease inhibitor available from Roche Diagnostics, Inc. of Indianapolis, Ind.), spun down and supernatant was collected for measurement. Samples from animals in a same treatment group were pooled and expressed as a single data point.

Histological Examination of Tumors. Tumors from different treatment groups were excised at the end of experiments (15 days after initial treatment). They were then deep frozen in liquid nitrogen with TISSUE-TEK™ OCT compound (Sakura of Torrance, Calif.) as embedding medium, sectioned and mounted. They were then stained with hematoxylin-eosin and evaluated by light microscopy at 400× magnification.

Example 1

In vitro Expression of Adenoviral Gene Therapy Constructs

Eighty percent confluent 4T1 cells were infected with AdIL12/B7.1 at a MOI of 5/cell for 5 hours. Twenty-four hours after the beginning of infection, cells were detached with 0.05% trypsin (Gibco/Life Technologies of Rockville, Md.) and resuspended in PBS with 3% normal rat serum. Cells were incubated with monoclonal biotin-labeled anti-mouse B7.1 antibody (Caltag of Burlingame, Calif.) for 30 minutes, washed in PBS, and incubated in streptavidin-phycoerythrin (Pharmingen of San Diego, Calif.) for 30 minutes. Incubations and washes were performed at 4° C. Samples were measured on a FACStar flow cytometer (Becton-Dickinson of Franklin Lakes, N.J.).

FIG. 1A presents levels of expression of the reporter gene GFP in cell cultures infected with an adenovirus encoding GFP. Levels of GFP were measured using FACS analysis. FIG. 1B presents levels of expression of IL12 in cell cultures infected with an adenoviral construct encoding IL12. Levels of IL12 were quantitated using immunodetection methods described herein above.

Example 2

In vivo Expression and Systemic Dissemination of Reporter Gene Adenovirus $3 \times 10^8$ pfu (plaque forming unit) of AdGFP in 50 µl PBS were intratumorally injected when subcutaneous B16.F10 melanoma tumors reached a diameter of 5–7 mm. The mice were sacrificed 24 hours later. Fluorescence microscopy of harvested tumors and organs (FIG. 2) demonstrated high numbers of GFP expressing cells in the liver and spleen and to a lesser extent in the lung of C57BL/6 mice bearing B16 melanoma at 24 hours after virus injection. The GFP-expressing area in the tumor was limited to a small volume around the presumed needle track. GFP expression in the liver was almost homogeneous and infected areas were seen throughout the whole spleen. No relevant GFP expression was detected in kidneys or brain of AdGFP injected animals or in any organs of the control animals.

Example 3

Intratumoral Expression of Plasmid Gene Therapy Vectors

B16.F10 tumors grown to 5–7 mm in diameter (or 65–179 mm$^3$) in volume were injected with EGFP or β-gal reporter plasmids and electroporated to promote cell transduction. Expression of reporter genes (EGFP and β-gal) after plasmid injection and electroporation in tumor tissue was assessed in fresh tissue sections (at 250 µm) by fluorescence microscopy and transmission light microscopy (FIG. 3). For both reporter systems, few cells were positive when only naked DNA without consecutive electroporation was injected. The combination with electroporation resulted in consistently efficient transduction of a higher number of cells with both reporter genes. In EGFP experiments, plasmid injection with electroporation allowed 3–8% (as evaluated by fluorescence-activated flow cytometry) of all the cells in the tumor mass to be transduced with the EGFP gene in comparison to <0.1% in tumors injected with EGFP plasmid alone.

Example 4

Determination of Tumor and Serum Levels of Plasmid Gene Therapy Constructs

To quantitatively evaluate local and systemic transgene expression as a consequence of electroporation and control gene transfer approaches, mIL12 (as a heterodimer of p35 and p40 subunits) levels were assessed in tumor and serum of untreated and treated animals. The mIL12 levels in the serum and tumors were below the detection threshold (8 pg/ml) in untreated or electroporation alone control animals.

FIG. 4 is a summary of the peak mIL12 levels in treated animals. With the mIL12 plasmid injection alone, the cytokine level in the tumor reached from below the level of detection(day 2) to a peak of 0.3 ng/g (day 5) while the level in the serum reached from below the level of detection (day 2) to a peak of 0.4 ng/ml (day 5). In those tumors that were injected with the control GFP encoding plasmid, the tumor and serum levels of the cytokine were similar to those with mIL12 alone, indicating that the low level of cytokine expression observed with the mIL12 plasmid injection alone were perhaps the result of DNA injection itself rather than any specific gene expression. When mIL12 plasmid injection was combined with electroporation, the cytokine level reached 2.6 ng/g on day 2 and 5.4 ng/g on day 5 in the tumor while the level in the serum reached from below the level of detection (day 2) to 0.35 ng/ml, similar to that achieved with plasmid injection alone. In comparison, in animals that were intratumorally injected with a therapeutically effective dose of $3 \times 10^8$ pfu of AdIL12, an adenovirus encoding the murine IL12 gene under the control of the cytomegalyvirus promoter, the mIL12 levels were between 7.2 (day 2) and 5.7 ng/g (day 5) in the tumor while the peak value (at day 2) in the serum reached 20 ng/ml. For both modalities, tumor mIL12 levels returned to baseline at 9 days after treatment.

Therefore, significant tumor levels of IL12 can be achieved in vivo by combining mIL12 plasmid injection and electroporation when compared to AdIL12 injection. Serum levels, however, were greatly elevated following local AdIL12 injection (reaching a maximum of 20 ng/ml) while they were close to non-specific DNA control after the combination of plasmid injection and electroporation (maximum of 0.4 ng/ml, FIG. 4). In addition, apparent toxicity was observed in animals injected with AdIL12, including weight loss, apathy, and splenomegaly.

Example 5

Heat Parameters for hsp70B Induction

To observe gene activation at different temperatures, MT1 mammary cancer cells were infected with AdhspGFP at a MOI of 20/cell. Transformed cells were heated for 20 minutes at different temperatures ranging from 39° C.–44° C. in 1° C. increments. GFP expression was evaluated 24 hours later using both FACS and fluorescence microscopy analyses (FIG. 5A). Levels of GFP protein were quantified by Western blot analysis (FIG. 5B).

Example 6

Kinetic Profile of Heat-Induced hsp70B Promoter Activity

To study the kinetics of transcriptional activation by heat, 4T1 cells or B16.F10 cells were infected with Adhsp70BGFP at MOI of 20/cell and subsequently incubated at 43° C. for 20 minutes. GFP expression was observed by fluorescence microscopy at multiple time points following heat treatment (FIG. 5C).

Example 7

Heat-Induced Expression of Therapeutic Genes In vitro

AdhspmIL12 and AdhspTNFα were constructed as described in the methods under the heading "Adenoviral vectors" herein above. 4T1 cells at 70% confluence were infected with AdhspmIL12 or AdhspTNFα at a MOI of 25. Cells were heated at 42° C. for 30 minutes. Cell supernatants were collected 48 hour later. ELISA test kits (R&D Systems of Minneapolis, Minn.) were used to measure TNF-α and IL12 concentrations in supernatants of infected cells as described in the methods under the heading "Measurement of cytokine levels" herein above. Results are presented in Table 2.

Example 8

Heat-Induced Expression of Therapeutic Genes in a Mouse Melanoma Model

Figure 9A:
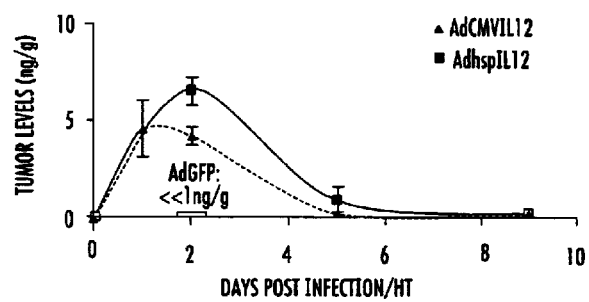
FIG. 9A is a graph depicting a time course of intratumoral levels of IL12 after injection of AdCMVIL12 (■), AdhspIL12 (▲), or AdGFP (small gray box) into B16 tumors.
Figure 9B:
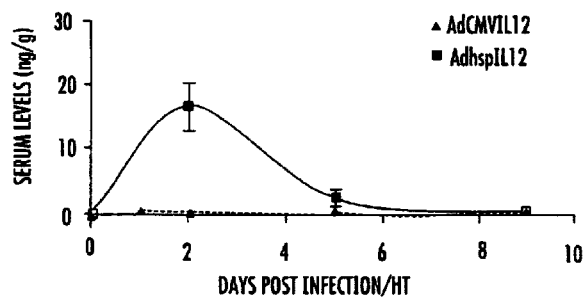
FIG. 9B a graph depicting a time course of serum levels of IL12 after injection of AdCMVIL12 (■) or AdhspIL12 (▲) into B16 tumors.

For measurement of heat-inducible gene expression in vivo, AdhspIL12 ($3\times10^8$ pfu in 50 µl PBS/tumor) or AdhspTNF-α ($1\times10^8$ pfu PBS/tumor) was injected intratumorally into B16.F10 melanomas grown in the hind leg of C57BL/6 mice (Charles River Laboratories of Wilmington, Mass.). In a subset of animals, tumor-bearing limbs were subjected to local hyperthermia by submersion in a circulating water bath (42.5° C., 40 minutes) 24 hours after the injection. Tumors were excised from animals that had been injected with the virus, homogenized in PBS, and used for analysis of cytokine levels. FIGS. 8 and 9A–9B summarize the intratumoral and systemic levels of reporter and therapeutic gene products encoded by heat-inducible adenoviral constructs following intratumoral injection and heat treatment to induce gene expression. Results are presented in Table 3 above.

Example 9

Heat-Induced Expression of Therapeutic Genes in a Feline Sarcoma Model

The infectiveness and expression of AdhspGFP was examined in a feline sarcoma model. Consistent with observations in model murine tumors, intratumoral injection of AdhspGFP followed by heat treatment of the tumor induced GFP expression (FIG. 6). By contrast, GFP was not detected in non-heat treated control sarcomas (FIG. 6).

FIG. 6 shows fluorescence images of a feline sarcoma following intratumoral injection of AdhspGFP. GFP expression is observed as regions of white signal. Heat treatment of the sarcoma induced GFP expression (bottom panel), whereas GFP expression was not observed in control animals that did not receive a heat treatment (top panel).

AdhspmIL12 ($1\times10^{10}$ pfu) was also injected intratumorally into a feline sarcoma patient. The tumor was heated at 24° C. for 1 hour, beginning at 48 hours post-injection. Cytokine levels were measured before and after heating using ELISA kits. Similar to the results observed in mouse, levels of IL12 in the tumor tissue were below the sensitivity of detection (75 pg/g of tumor tissue) prior to heat treatment, and reached a peak level of 2700 pg/g of tumor tissue following heat treatment.

Example 10

Measurement of Intratumoral and Systemic Levels of Locally Provided Adenoviral Vector Intratumoral and systemic expression of murine interleukin 12 (mIL12) was studied after local injection of either control adenovirus, adenovirus constitutively expressing mIL12 (AdmIL12) or adenovirus expressing mIL12 controlled by a heat inducible promoter (AdhspIL12) combined with heat treatment in subcutaneous B16.F10 melanomas in C57BL/6 mice. Equal amounts ($3\times10^8$ pfu in 50 µl) of control adenovirus (AdGFP), AdCMVIL12, or AdhspIL12 were intratumorally injected seven days after B16.F10 cell transplantation (tumor diameter 5–7 mm). Animals injected with control virus or AdCMVIL12 were sacrificed 48 hours after virus injection. Animals injected with AdhspIL12 were treated with local hyperthermia to the right hind leg (by submersion in water bath, 42.5° C., 40 minutes) 24 hours after virus injection under anesthesia with pentobarbital (1.5 mg per 20 g mouse i.p.).

The animals were sacrificed 48 hours after heating. Serum samples (tail vein blood) of all animals were acquired immediately before euthanasia. Tumors and organs (liver, spleen, and lung) of sacrificed animals were disaggregated in PBS (1 ml/100 mg tumor) with COMPLETE® protease inhibitor (Boehringer Mannheim of Mannehim, Germany) with a tissue homogenizer for 1 minute on ice. After centrifugation, the supernatant was harvested. IL12 concentrations in tumor and organ extracts and serum samples were detected with a mIL12 ELISA kit detecting the p70 heterodimer (R&D systems of Minneapolis, Minn.) with a detection level of 2.5 pg/ml. The results are plotted as mean ±range of two to four animals per data point.

FIGS. 8 and 9A–9B summarize the intratumoral and systemic levels of reporter and therapeutic gene products encoded by heat-inducible adenoviral constructs following intratumoral injection and heat treatment to induce gene expression.

Example 11

Adenoviral-Mediated Gene Therapy in a Mouse Melanoma Model

Viral vectors were injected intratumorally using a 30-gauge needle at a dosage of 1×10$^9$ pfu/tumor in a volume of 50 µl OPTI-MEM™ growth medium (Life Technologies, Inc. of Rockville, Md.). Tumors were heated by immersing the tumor-bearing limb in a circulating water bath at 42.5° C. for 40 minutes beginning 24 hours post-injection. A second heat treatment was identically performed 24 hours later (48 hours post-injection). Tumor volume was determined by measuring the largest (L) and the smallest (S) diameters of the tumor and calculated as V=π/6(L×S$^2$). Growth curves are plotted as the mean relative treatment group tumor volume±standard error of the mean (SEM). Relative tumor growth rate were calculated for the first 6 days after treatment. FIG. 10 summarizes tumor growth delay conferred by adenovirus-mediated, hyperthermia-controlled gene therapy.

Example 12

Plasmid-Mediated Gene Therapy in a Mouse Melanoma Model

Three treatment regimens were established: (i) plasmid injection, no electroporation; (ii) plasmid injection, electroporation; (iii) no plasmid injection, electroporation. Each treatment group consisted of 9 animals. All animals were anesthetized before plasmid injection/electroporation with Ketamine/Xylazine at 1.8/0.15 mg per mouse. After tumors grew to sizes of 5–7 mm in diameter (or 65–179 mm$^3$ in volume), they were injected intratumorally with 50 µg of either EGFP-, β-gal-, mIL2- or mIL12 plasmid in 50 µl PBS (phosphate-buffered-saline). Animals intended for combination treatment underwent subsequent electroporation within 1–5 minutes. Electroporation pulses were delivered with 2×2 cm stainless steel plates attached to a caliper electrode (Genetronics Inc. of San Diego, Calif.). Electrode gel (SIGNA GEL™, Parker Laboratories Inc. of Fairfield, N.J.) was applied to the electrodes to reduce the interfacial resistance and maintain good electrical contact between electrode and skin.

Figure 11A:
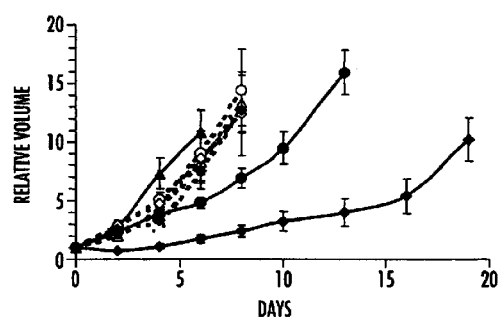
FIG. 11A is a graph depicting tumor growth delay conferred by plasmid-mediated gene therapy. The mean relative tumor volume (±standard error of the mean (SEM)) is indicated during a 20-day period following gene therapy treatment of B16.F10 tumors in C57BL/6 mice. (■) no treatment control, (Δ) EGFP plasmid alone, (▲) EGFP plasmid+electroporation, (○) mIL2 plasmid alone, (●) mIL2 plasmid+electroporation, (◇) mIL12 plasmid alone, (♦) mIL12 plasmid+electroporation.
Figure 11B:
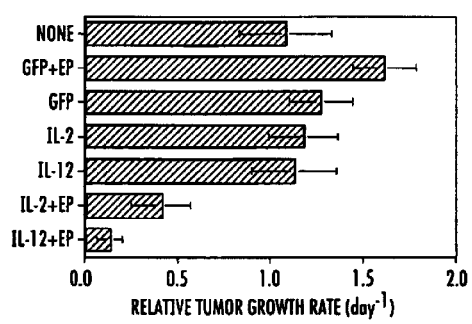
FIG. 11B is a graph depicting relative tumor growth delay of plasmid-mediated gene therapy with or without in vivo electroporation. Tumor growth rate is shown during the first 6 days following treatment. The values represent the slopes of the relative growth curve in FIG. 10A as calculated by linear curve fitting.

The caliper electrodes were clamped on the tumor in an approximate dorsal-ventral orientation as to avoid placing any bone within the electric field. The distance between electrodes was approximately 6 mm. Square wave electric pulses were generated with an Electro Square Porator T820 (Genetronics Inc. of San Diego, Calif.). Three pulses (100V/50 ms) were delivered, followed by three more pulses at the opposite polarity. These electroporation parameters were selected based on previous reports (Suzuki et al. (1998) *FEBS Lett* 425:436–440; Mathiesen (1999) *Gene Ther* 6:508–514; Harrisson et al. (1998) *FEBS Lett* 435:1–5) and empirical determination. Tumor volume was determined by measuring the largest (L) and the smallest (S) diameters of the tumor and calculated as V=π/6(L×S$^2$). Growth curves are plotted as the mean relative treatment group tumor volume±standard error of the mean (SEM). Relative tumor growth rate were calculated for the first 6 days after treatment. FIG. 11A summarizes tumor growth delay conferred by plasmid-mediated gene therapy. FIG. 11B shows that plasmid-mediated gene therapy is facilitated by in vivo electroporation.

Example 13

Combined Gene Therapy and Radiation Treatment in a Mouse Melanoma Model

About 10$^6$ cells in 50 µl PBS of either 4T1 or B16.F10 were transplanted in the right hind limbs of BALB/c or C57BL/6 mice respectively. Treatment was initiated when the tumors had reached a mean diameter of 5–7 mm. Each treatment group consisted of 6–10 animals, and each treatment group was treated with or without radiation and with or without a single intratumoral injection of AdGFP or AdIL12/B7.1. Adenoviral vectors were injected intratumorally either immediately after the first radiation fraction, immediately after the last fraction or—for 4T1 only—before the first fraction with the radiation treatment being postponed for 2 days. The virus dose injected was 3×10$^8$ pfu (in 50 µl PBS) except for the injection after the third radiation fraction in 4T1, when 3×10$^7$ pfu were used because of acute systemic toxicity, which, however, was only witnessed in Balb/c mice from one supplier.

For exposure of tumors to ionizing radiation, mice harboring tumors were placed in plastic restrainers without anesthesia. The dosage used were 3×6 Gy for 4T1 and 3×11 Gy for B16.F10. Up to 12 mice were exposed to ionizing radiation at a time, the legs placed in a 30 cm 30 cm field with 1 cm water equivalent bolus on a 4MV linear accelerator (Varian of Palo Alto, Calif.) at a dose rate of 2 Gy/min. Growth curves are plotted as the mean relative treatment group tumor volume±standard error (SE). Mean times to reaching four times initial tumor volumes (phase of exponential regrowth) for each group were calculated and compared using the Kruskal-Wallis and the two sided Mann-Whitney test (nonparametric). FIGS. 12–13 summarize the observed tumor growth delay following different combinations of radiotherapy and gene therapy, and reveals that the combined treatment is more effective than either radiotherapy or gene therapy alone.

Example 14

Combined Heat-Inducible Gene Therapy and Radiation Treatment in a Mouse Melanoma Model Four groups of 6–10 animals were treated as follows: (i) no radiation treatment, AdGFP intratumoral injection; (ii) radiation treatment, AdGFP intratumoral injection; (iii) no radiation treatment, AdhspIL12 intratumoral injection; (iv) radiation treatment, AdhspIL12 intratumoral injection.

For local tumor radiotherapy, mice were place in plastic restrainers without anesthesia such that only their legs were placed in a 30 cm×30 cm field with 1 cm water equivalent bolus on a 4 MV linear accelerator (Varian of Palo Alto, Calif.) at a dose of 2 Gy/min. Previous studies showed that a fractionation of 3×11 Gy alone resulted in some growth delay. Up to 12 mice were exposed to ionizing radiation simultaneously.

For combined gene therapy and radiation treatment, AdGFP or AdhspIL12 was injected 24 hours before the last radiation fraction. Alternatively, AdGFP or AdhspIL12 was injected 3 days after the last radiation fraction. The virus was injected at a dose of 3×10$^8$ pfu/tumor in 50 µl PBS. In preparation for heat treatment, animals were anesthetized by intraperitoneal injection with 1.5 mg Pentobarbital per 20 g mouse. In addition, the tumor-bearing leg was wrapped with thin plastic foil to minimize local toxicity resulting from direct water contact. In vivo hyperthermia treatment was performed by submersion of the tumor-bearing leg in a circulating water bath heated to 42.5° C. for a duration of 40 minutes. For control studies, the tumor-bearing leg was immersed in a circulating water bath heated to 34° C. for a duration of 40 minutes. For animals that were injected 24 hours prior to the last radiation fraction, heat treatment was performed 24 hours after intratumoral injection and immediately after the last radiation fraction. For animals that were injected 3 days after the last radiation fraction, heat treatment was performed 24 hours post-injection.

FIGS. 14–15 summarize the observed tumor growth delay following different combinations of radiotherapy and heat-inducible gene therapy, and reveals that the combined treatment is more effective than either radiotherapy or gene therapy alone.

Example 15

Immunization Studies

To study the potential protective immunity induced by lethally irradiated, AdIL12/B7.1 infected 4T1 cells, BALB/c mice were immunized subcutaneously with $10^6$ lethally irradiated cells (70 Gy of γ-rays). The cells were treated with or without previous in vitro infection with AdIL12/B7.1 (MOI of 20 per cell) prior to lethal irradiation. Animals were immunized once per week for 3 weeks. One week following the last immunization, $10^6$ untreated 4T1 cells were transplanted in the right hind limb in both groups for observing tumor growth. FIG. 16 summarizes delayed tumor growth in mice immunized with lethally irradiated 4T1 cells infected with AdIL12/B7.1

Example 16

IL12 Gene Therapy in Nude and NK Cell-depleted Mice

About $10^6$ cells of either 4T1 or B16.F10 were transplanted in the right hind leg of Balb/c nude/nude mice (Taconic of Germantown, N.Y.). Tumors in the range of 5–7 mm in diameters were established in 7–10 days. AdGFP or AdIL12/B7.1 ($3\times10^8$ pfu) were then injected intratumorally to study the therapeutic effect of the virus in a T-cell-depleted host. The role of NK cells was studied by use of antibody-mediated NK depletion in nude mice. To assess NK-mediation of AdIL12/B7.1 effects, a group of animals was NK-depleted with the polyclonal antibody anti-asiolo GM1 (Wako Chemicals of Richmond, Va.). Fifty microliters of antibody stock solution (titer 1:1000) was injected intravenously in 150 μl H$_2$O on day −2 (2 days prior to virus injection) and 25 μl in 75 μl H$_2$O on day −1 (1 day prior to virus injection) and +1, +4, and +7 (1, 4, and 7 days after virus injection) before and after the virus infection for the duration of the experiment. Success of depletion was assessed after two antibody injections with a splenocyte cytotoxicity assay as described herein above after NK-activation by intraperitoneal injection of 100 μg Poly I:C (Sigma of St. Louis, Mo.) 18 hours before spleen harvesting. However, in this case, NYLONWOOL™ separation (Robbins Scientific of Sunnyvale, Calif.) was not performed, and the NK-sensitive YAC-1 cell line (ATCC) was used as the target. Two spleens of antibody-treated and untreated animals each were pooled. NK activity was reduced to <2% as assessed by this assay.

Figure 17A:
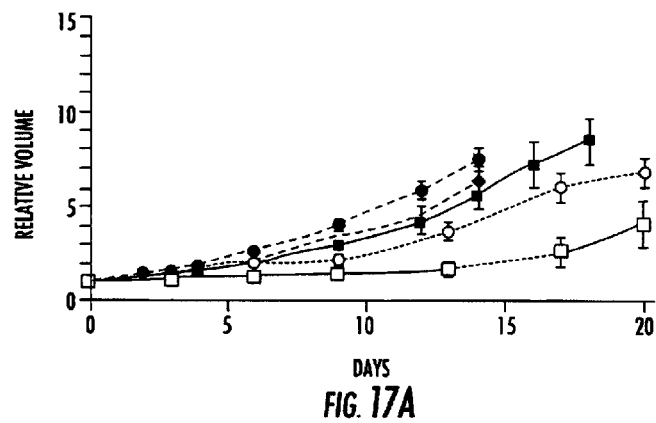
FIG. 17A is a graph depicting mean relative tumor volumes +standard error (X-axis) for 4T1 tumors in Balb/c, nu/nu mice after intratumoral injection of AdGFP or AdIL12/B7.1, with or without previous NK-cell depletion. (●) AdGFP, (■) AdIL12/B7.1, (♦) AdIL12/B7.1 in NK depleted animals. For comparison, the growth curves for tumors treated with AdGFP alone (○) and AdIL12/B7.1 alone (□) in the respective immunocompetent hosts (Balb/c or C57BL/6 mice) are also plotted.
Figure 17B:
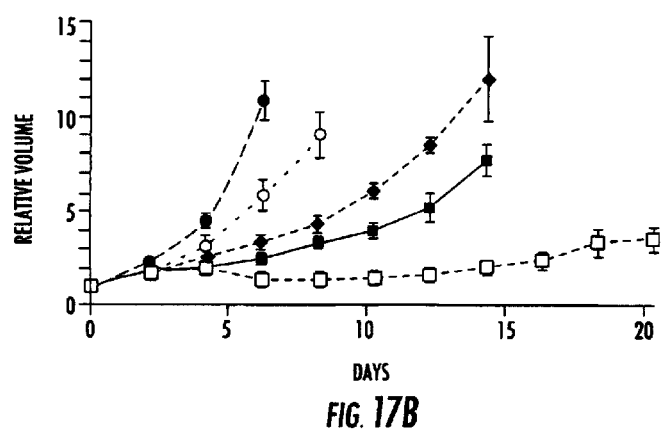
FIG. 17B is a graph depicting mean relative tumor volumes±standard error (X-axis) for B16.F10 tumors in Balb/c nu/nu mice after intratumoral injection of AdGFP or AdIL 2/B7.1, with or without previous NK cell depletion. (●) AdGFP, (■) AdIL12/B7.1, (♦) AdIL12/B7.1 in NK-depleted animals. For comparison, the growth curves for tumors treated with AdGFP alone (○) and AdIL12/B7.1 alone (□) in the respective immunocompetent hosts (Balb/c or C57BL/6 mice) are also plotted.

FIGS. 17A and 17B summarize tumor growth in 4T1 and B16.F10 tumors, respectively, after intratumoral injection of various adenoviral constructs, with or without previous NK cell depletion. Administration of AdIL12/B7.1 resulted in delayed tumor growth, and NK depletion partially abrogated this therapeutic effect.

Example 17

Cytotoxic T Cell Activity Assay

Activity of cytotoxic T-lymphocytes (CTL) was assessed with a modified standard chromium-release assay (Holm & Perlman (1967) *Immunol* 12:525–536; Barth et al. (1990) *J Immunol* 144:1531–1537). Seven days after intratumoral injection of AdIL12/B7.1, AdGFP or normal saline, spleens of three animals each were harvested, pooled and disaggregated. Erythrocytes were lysed with ammonium chloride (3 minutes, 37° C.), and T-cells were purified by two rounds of NYLONWOOL™ separation (Robbins Scientific of Sunnyvale, Calif.). For restimulation, $10^7$ T-cells/well were co-cultivated with $10^6$ target cells/well (4T1 or B16.F10, irradiated with 200 Gy to prevent overgrowth) in 6-well plates with c-RPMI lymphocyte medium (440 ml RPMI 1640, 100 u/100 mg penicillin/streptomycin, 2 mM 1-glutamine, 55 mM 2-mercaptoethanol, 10% FCS, 10 mM Hepes) with or without 100 U/ml mlL2 for 5 days. Afterwards, the cell suspension was harvested and mononuclear cells were separated by centrifugation over a HISTOPAQUE® 1083 lymphocyte separation gradient (Sigma of St. Louis, Mo.).

For the effector assay, $4\times10^6$ target cells (4T1, B16.F10 or Yac-1) were labeled with 150 mCi sodium $^{51}$chromate for 70 minutes. Finally, $10^4$ target cells were co-cultivated with effector cells in varying effector/target ratios in triplicates in U-bottom 96-well plates for 4 hours at 37° C. Minimum (no effectors) and maximum (1% TRITON-X™ solution) release as well as the release in each effector/target well were determined by adding 100 ml of supernatant after centrifugation to 100 ml of scintillation fluid in a 96-well plate of a Wallac beta-counter (Wallac of Turku, Finland). Specific lysis was determined according to the following formula:

$$\% \text{ specific lysis} = \frac{(\text{release of sample} - \text{spontaneous release})}{(\text{maximum release} - \text{spontaneous release})}$$

Spontaneous release was always <15% of the maximum release. Each experiment was repeated with similar results.

FIG. 18 summarizes the percentaage specific lysis response of splenocytes from tumor-bearing mice treated with various adenoviral vectors against B16.F10, Tramp, and YAC-1 cells. Splenocytes from animals injected intratumorally with AdIL/B7.1 showed reduced CTL activity relative to control splenocytes.

Example 18

Detection of Collagen IV and CD31 in Animals Treated with IL12

C57BL/6 mice were transplanted with $10^6$ B16.F10 cells in the right hind limb. After reaching a mean diameter of 5–7 mm, tumors were treated with injection of either $3\times10^8$ pfu AdGFP or AdIL12/B7.1. At 7 days after initiating treatment, tumors were harvested, deep frozen in liquid nitrogen with TISSUE-TEK™ OCT compound (Sakura of Torrance, Calif.) as embedding medium, sectioned and mounted. After blocking with serum (Jackson Immunoresearch of West Grove, Pa.), sections were stained according to a standard immunohistochemistry protocol (Hsu et al. (1981) *J Histochem Cytochem* 29:577–580) with rabbit-anti-mouse monoclonal anti-collagen type IV (Chemicon of Temecula, Calif.) and rat anti-mouse CD31 (Pharmingen of San Diego, Calif.) as primary antibodies, and a biotinylated secondary antibody (Jackson Immunoresearch of West Grove, Pa.). Visualization of the immunoreaction was achieved by further incubation with a streptavidin-horseradish peroxidase conjugate and 3-diaminobenzidine tetrahydrochloride available from Sigma of St. Louis, Mo. After immunostaining, slides were counterstained with hematoxylin-eosin and mounted, and five areas of high vessel density per tumor were quantitatively assessed for vessel density at 400× magnification, as shown in FIGS. 19A and 19B. Blood vessel density is reduced in tumors treated with AdIL12/B7.1 (FIG. 19B) relative to tumors treated with the control vector AdGFP (FIG. 19B).

Example 19

Hyperthermia-facilitated Nanoparticle Extravasation from Tumor Vasculature

Albumin and Liposomes. Rhodamine (Rho)-labeled bovine serum albumin (BSA) was purchase from Sigma Chemical Company (St. Louis, Mo.) and dissolved in PBS to a concentration of 2 mg/ml. Rhodamine-labeled, sterically stabilized, long-circulating PEG liposomes were prepared by the lipid film hydration and extrusion method (Hope et al. (1985) *Biochim Biophys Acta* 812:55–65). The formulation for the liposomes was egg phophatidylcholine:cholesterol:1,2-distearoyl-sn-glycero-3-phosphoethanol-amine-N-polyethyleneglycol 2000:Rho-PE in the molar ratio of 10:5:0.8:0.1 (Yuan et al. (1995) *Cancer Research* 55:3752–3756). The final lipid concentration after hydration was 20 mg/ml. Liposomes of various sizes were prepared by passing a liposome preparation through polycarbonate filters (Poretics of Livermore, Calif.) with pore diameters of 0.4 μm, 0.2 μm, and 0.1 μm, depending on the target size. Liposome size was determined by dynamic light scattering using a Coulter N4 MD submicron particle size analyzer (Coulter Electronics of Hialeah, Fla.). All liposome preparations had a narrow size distribution (95% of the liposomes were within ±10 nm for 100-nm liposomes, ±15 nm for 200-nm liposomes, and ±25 nm for 400-nm liposomes.

Animal and Tumor Model. Homozygous NCr athymic nude mice (20±3 g) were purchased from Taconic (Germantown, N.Y.). Animals were housed in appropriate isolated caging with sterile rodent laboratory chow and approved by the Duke Institutional Animal Care and Use Committee. The athymic nude mouse dorsal skin flap window chamber model was used (Huang et al. (1999) *Nat Biotech* 17:1033–1035). Briefly, titanium window chambers were surgically placed on the dorsal skin flap of athymic nude mice, and a small volume (~0.1 mm$^3$) of tumor tissue (human ovarian carcinoma; SKOV-3) was implanted in the window chamber. After 10–124 days, the tumor was visibly well vascularized and ~1–2 mm in diameter. This preparation was then used for experiments. For experiments requiring normal vessels, the same window chamber model was prepared without tumors implanted and allowed to mature for 10–14 days before experimentation.

The permeability of tumor vasculature to liposomes is dependent on the tumor type (Yuan et al. (1994) *Cancer Research* 54:4564–4568). Some tumors have pore cutoff sizes between 400 and 600 nm (Yuan et al. (1995) *Cancer Research* 55:3752–3756). After initially screening several tumor types, SKOV-3, a human ovarian carcinoma was found to be highly impermeable to 100-nm liposomes under normothermic conditions. Non-tumor-bearing window chamber vessels were similarly impermeable to 100-nm liposomes under normothermic conditions. Because this tumor represents a limiting case for permeability, it was chosen as the model for this study. It provides a strict model for assaying the ability of hyperthermia to enable and increase permeability as well as pore cutoff size in tumor relative to normal vessels.

Experimental Groups. Each experimental group had six mice. Albumin, 100-nm liposomes, 200-nm liposomes, and 400-nm liposomes were each tested in tumor-bearing window chambers at 34° C., the normal subcutaneous skin temperature of mice (Gaber et al. (1996) *Int J Radiat Oncol Biol Phys* 36:1177–1187), 39° C., 40° C., 41° C., and 42° C., a temperature that has been shown previously to have some effect on liposome delivery (Kong & Dewhirst (1999) *Int J Hyperthermia* 15:345–370). Liposomes (100 nm) were also tested for extravasation from normal vessels in non-tumor-bearing window chambers at 42° C. To evaluate the time frame over which hyperthermia affects nanoparticle extravasation, tumors were heated at 42° C. for 1 hour and allowed to return to normothermia. Nanoparticles were subsequently administered at 2, 4, or 6 hours following heat treatment. To evaluate whether there is evidence for thermotolerance to heat-facilitated nanoparticle extravasation, tumors were heated to 42° C. for one hour followed by a second heat treatment (42° C. for one hour) 8 hours later.

Experimental Procedure. In each experiment, animals were anesthetized with sodium pentobarbital (80 mg/kg; intraperitoneal injection). The tail vein was cannulated for intravenous injection of albumin or liposomes during the experiment. The animal was placed on a temperature-controlled microscopic stage to maintain normal body temperature through out the experiment. The window chamber was fixed in a specially designed hyperthermia chamber (Gross et al. (1982) *Int J Heat Mass Transfer* 25:1313–1320) that allowed for visualization of the tumor while the chamber was being heated (to 34° C. or 42° C., depending on the experimental group). The window chamber and tumor were allowed to reach steady-state temperature (~2 min as determined by thermographic imaging) in the hyperthermia chamber before injection of liposomes or albumin. The preparation in the window chamber was observed with a 20× objective lens. For analysis of particle extravasation, a region in the preparation with steady blood flow and few obvious underlying vessels was selected. The images of the selected region were recorded with a SIT camera (model C2400-08 available from Hamamatsu Corporation of Bridgewater, N.J.) connected to an S-VHS video tape recorder (model BV-1000 available from Mitsubishi Kasei America, Inc. of Menlo Park, Calif.). This regions was first recorded under transillumination. Then, under epi-illumination with a filter set for rhodamine (model H546 available from Carl Zeiss, Inc. of Thronwood, N.Y.), a background image of the selected regions was recorded before injection of liposomes or albumin. Next, 0.2 ml of rhodamine-labeled liposomes or albumin was administered intravenously. The region was recorded under epi-illumination intermittently (for 10 seconds every 2 minutes) for 60 minutes after the injection of nanoparticles.

The videotape of the experiment was analyzed with image processing software, NH Scion Image (publicly available at http://rsb.info.nih.gov/nih-image). The fluorescent light intensities of the entire selected region and representative vascular regions were measured at serial time points. The relative fluorescent light intensities of the vascular and interstitial components were determined as described by Wu et al. (Wu et al. (1993) *Microvasc Res* 46:231–253). All light intensities were normalized to the initial vascular light intensity in the region after injection of liposomes or albumin. Vascular volumes for all experimental groups were not statistically different. Because the light intensity is proportional to the number of particles present (Wu et al. (1993) *Microvasc Res* 46:231–253), the data are presented as RTIA or accumulation in this report. RTIA values taken at 60 minutes are defined as $RTIA_{60}$.

Statistics. Changes in RTIA were summarized by averaging data from individual animals in each group (albumin, 100-nm liposomes, 200-nm liposomes, and 400-nm liposomes at 34° C. or 42° C.). Statistical significance between experimental groups (treatment temperatures for each size or different sizes for same treatment temperature) was determined using the Mann Whitney U test. Two quantities were regarded as different if $P<0.05$.

Observations of Nanoparticle Extravasation. To measure the extravasation of albumin or liposomes under normothermic and hyperthermic conditions, tumor models treated according to the procedures herein above were viewed using epi-illumination and a filter set appropriate for rhodamine visualization. In general, the fluorescent signal of labeled particles was initially detected about 10 seconds following injection and became stable within 30 seconds. Tumor blood vessels retained fluorescent liposomes throughout a 60-minute period following injection. Perivascular regions or fluorescent signal indicated initial liposome extravasation that later became more diffuse and spread throughout the tumor interstitium. Hyperthermia enabled extravasation for all sizes 100 nm, although the degree of enhancement varied according to size.

Under normothermic conditions (34° C.), 100-nm showed no accumulation ($RTIA_{60} \sim 0$). This was significantly lower than the $RTIA_{60}$ for albumin at 34° C. ($P<0.005$). Heat treatment at 42° C. significantly increased the accumulation of 100-nm liposomes in the tumor interstitium ($P<0.02$) with a $RTIA_{60} \sim 1.5$. The $RTIA_{60}$ of albumin and 100-nm liposomes at 42° C. was similar.

The 200-nm and 400-nm liposomes also showed no extravasation at normothermic conditions ($RTIA_{60} \sim 0$). Enhanced extravasation of 220-nm liposomes was observed at 42° C. ($RTIA_{60} \sim 0.96$). Similarly, 400-nm liposomes showed an initial increase in extravasation that reached a plateau level within 25 minutes ($RTIA_{60} \sim 0.43$; $RTIA_{60} \sim 0$ at 34° C.). At 42° C., the degree of extravasation between the 100-nm liposome and the 400-nm liposome was significantly higher ($P<0.02$), whereas the differences between the 100-nm and the 200-nm liposomes and between the 200-nm and 400-nm liposomes were not significant. Thus, at all liposome sizes tested, heat treatment resulted in more liposome accumulation in the tumor interstitium.

To further define the optimal temperature for heat-facilitated extravasation, 100-nm particles were further tested at 34° C.–42° C. because this represented an important physiological and therapeutic temperature range. At 34° C. and 39° C., nanoparticles did not extravasate into the tumor interstitium ($RTIA_{60}s \sim 0$). Above 42° C., the tumor vessels hemorrhaged and collapsed. At 34From 40° C.–42° C., nanoparticle extravasation increased with temperature ($RTIA_{60}s \sim 0.46$, 0.94, and 1.43 ate 40° C., 41° C., and 42° C., respectively). The $RTIA_{60}s$ at 41° C. and 42° C. were not significantly different from each other ($P \sim 0.1$), but were both significantly higher than the $RTIA_{60}s$ at 34° C., 39° C., or 40° C. ($P<0.03$).

To determine whether the effect of hyperthermia on liposome extravasation was unique to tumor vessels, the extravasation of 100-nm liposomes at 42° C. was also studied in normal vessels in the window chamber model. Minimal extravasation of 100-nm liposomes at 42° C. from normal vessels was observed ($RTIA_{60} \sim 0$). The profile of liposome accumulation was similar to that seen with liposomes at 34° C. in tumor vessels. The $RTIA_{60} \sim 0$ of 100-nm liposomes at 42° C. in tumor vessels was significantly higher than in normal vessels ($P<0.01$).

To investigate the temporal dependence of heat-facilitated extravasation, nanoparticle extravasation was observed following administration of liposomes at different time points after heat treatment for 1 hour at 42° C. When liposomes were administered two hours after the end of the heat treatment period, the $RTIA_{60}$ was 0.70, still significantly above baseline level observed with no heat treatment ($P<0.01$), although lower than the $RTIA_{60}$ of 1.53 observed with simultaneous administration and heat treatment. When liposomes were administered 4 hours following heat treatment, the $RTIA_{60}$ was reduced to 0.32, but this level of extravasation was still above that observed in the absence of heat treatment ($P<0.01$). The effect of heat-facilitated extravasation was not observed when a 6 hour interval separated heat treatment and liposomes administration ($RTIA_{60} \sim 0$).

To determine whether heat-enhance extravasation could be repeated, a second set of tumors was heated twice: 1 hour at 42° C. followed by an additional hour at 42° C. 8 hours later. Increased extravasation was not observed following the second heat treatment.

REFERENCES

The references listed below as well as all references cited in the specification are incorporated herein by reference to the extent that they supplement, explain, provide a background for or teach methodology, techniques and/or compositions employed herein.

Adelman et al. (1983) *DNA* 2:183.
Alam & Cook (1990) *Anal Biochem* 188:245–254.
Albini et al. (2000) *Am J Pathol* 156(4):1381–1393.
Altschul et al. (1990) *J Mol Biol* 215: 403–410.
Anscher et al. (1997) *Int J Radiat Oncol Biol Phys* 37:1059–1065.
Aslakson & Miller (1992) *Cancer Res* 52:1399–1405.
Ausubel et al. (1992) *Current Protocols in Molecular Biology*, John Wylie and Sons, Inc., New York, N.Y.
Barth et al. (1990) *J Immunol* 144:1531–1537.
Barton (1998) *Acta Crystallogr D Biol Crystallogr* 54:1139–1146.
Batzer et al. (1991) *Nuc Acids Res* 19:5081.
Betageri et al. (1993) *Liposome Drug Delivery Systems*, Technomic Publishing, Lancaster.
Bevilacqua et al. (2000) *Development* 127(7):1541–1551.
Blackburn et al. (1992) *Cancer Res* 1358–1362. Blank & Goodman (1999) *J Cell Biochem* 75(3):369–374.
Bramson et al. (1997) *Gene Ther* 4:1069–1076.
Brawer et al. (1992) *J Urol* 147:841–845.
Cardillo et al. (2000) *Anticancer Res* 20(6B):4579–4583.
Carpizo & Iruela-Arispe (2000) *Cancer Metastasis Rev* 19(1–2):159–165).
Catalona et al. (1993) *JAMA* 270:948–958.
Cheng (1996) *Human Gene Therapy* 7:275.

Cipolla et al. (2000) *Hum Gene Ther* 11(2):361–371.
Clapp et al. (1993) *Endocrinol.* 133:1292–1299.
Clark & Griswold (1997) *J Androl* 18(3):257–263.
Coughlin et al. (1998) *J Clin Invest* 101:1441–1452.
Csermely et al. (1998) *Pharmacol Ther* 79(2):129–168.
Cubitt et al. (1995) *Trends Biochem Sci* 20:448–455.
Dacha et al. (1997) *Nature Med* 3:515–520.
D'Andre et al. (1992) *J Exp Med* 176:1387.
Dameron et al. (1995) *Science* 265:1582–1584.
Deshmukh et al. (2001) *J Neurosurgery* 94(2):287–292.
Dewhirst et al. (1990) *Int J Radiat Oncol Biol Phys* 18(5):1249–1259.
Dias et al. (1998) *Int J Cancer* 75(1):151–157.
Dreano et al. (1986) *Genes* 49:1–8.
Drujan & De Maio (1999) 12(6):443–448.
Easton et al. (2000) *Cell Stress Chaperones* 5(4):276–290.
Eijan et al. (1991) *Mol. Biother.*, 3:38–40.
Emami et al. (1991) *Int J Radiat Oncol Biol Phys* 20(5):1117–1124.
Emtage et al. (1999) *Hum Gene Ther* 10:697–709. EP 0 439 095
Foster et al. (1997) *Cancer Res* 57:3325–3330.
Freireich et al. (1966) *Cancer Chemotherap Rep* 50:219–244.
Gaber et al. (1996) *Int J Radiat Oncol Biol Phys* 36:1177–1187.
Gately et al. (1994) *Int. Immunol.* 6:157.
Gazit et al. (1995) *Cancer Res* 55:1660–1663.
Gazit et al. (1999) *Breast Cancer Res Treat* 54(2):135–146.
Glover, ed. (1985) *DNA Cloning: A Practical Approach*, MRL Press, Ltd., Oxford, United Kingdom.
Goldman et al. (1997) *Nat Biotechnol* 15:462.
Gore (1996) *Cancer Biother Radiopharm* 11 (5):281–283.
Gossen & Bujard (1992) *Proc Natl Acad Sci USA* 89:5547–5551.
Gossen & Bujard (1993) *Nuc Acids Res* 21(18):4411–4412.
Gossen et al. (1995) *Science* 268:1766–1769.
Graham & Prevec (1995) *Mol Biotech* 3:207–220.
Gregoriadis, ed. (1993) *Liposome Technology*, CRC Press, Boca Raton, Fla.
Gross et al. (1982) *Int J Heat Mass Transfer* 25:1313–1320.
Guffrey et al. (1995) *J Cutan Pathol* 22:122–127.
Habib et al. (1999) *Human Gene Therapy* 12:2019–2034.
Hallahan et al. (1995) *Nat Med* 1 (8):786–791.
Hauck & Stanners (1995) *J Biol Chem* 270:3602.
Heike et al. (1994) *J Immunotherapy* 15:165–174.
Heller et al. (1996) *FEBS Lett* 389:225–228.
Henikoff & Henikoff (1989) *Proc Natl Acad Sci USA* 89:10915.
Henikoff & Henikoff (2000) *Adv Protein Chem* 54:73–97.
Henikoff et al. (2000) *Electrophoresis* 21(9):1700–1706.
Hofmann et al. (1999) *Crit Rev Ther Drug Carrier Syst* 16:523–569.
Holm & Perlman (1967) *Immunol* 12:525–536.
Hope et al. (1985) *Biochim Biophys Acta* 812:55–65.
Horiguchi et al. (2000) *Gene Ther* 7(10):844–851.
Hsieh et al. (1993) *Science* 260:547.
Hsu et al. (1981) *J Histochem Cytochem* 29:577–580.
Huang et al. (2000) *Pac Symp Biocomput* 230–241.
Huang et al. (1999) *Nat Biotech* 17:1033–1035.
Ibrahim et al. (2000) *Cell Stress Chaperones* 5(3):207–218.
Ingber et al. (1990) *Nature* 348:555–557.

Janoff, ed. (1999) *Liposomes: Rational Design*, M. Dekker, New York, N.Y.
Joki et al. (1995) *Hum Gen Ther* 6:1507–1513.
Karlin & Altschul (1993) *Proc Natl Acad Sci USA* 90:5873–5887.
Kiang & Tsokos (1998) *Pharmacol Ther* 80(2):183–201.
Kiang et al. (1998) *FASEB J* 12(14):1571–16–579.
Kirk & Mule (2000) *Hum Gene Ther* 11 (6):797–806.
Kirpotin et al. (1997) *Biochemistry* 36:66.
Kobayashi et al. (1989) *J Exp Med* 1708:827.
Kong et al. (2001) *Cancer Research* 61:3027–3032.
Kong et al. (2000) *Cancer Research* 60:4440–4445.
Kong & Dewhirst (1999) *Int J Hyperthermia* 15:345–370.
Kosfeld et al (1993) *J Biol Chem* 267:16230–16236.
Kyte et al. (1982) *J Mol Biol* 157:105.
Labat-Moleuretal. (1996) *Gene Therapy* 3:1010–1017.
Larchian et al. (2000) *Clin Cancer Res* 6(7):2913–2920.
Lasic & Martin, eds. (1995) *Stealth Liposomes* CRC Press, Boca Raton, Fla.
Leopold et al. (1993) *Int J Radiat Oncol Biol Phys* 27:1245–1251.
Li et al. (1995) *J Biol Chem* 270:4971–4974.
Luna et al. (2000) *Cancer Res* 60(6):1637–1644.
Luo et al. (2001) *Clin Exp Immunol* 123(2):264–470).
Mackensen et al. (1997) *Cytokine Growth Factor Rev* 8(2):119–128.
Maione et al. (1990) *Science* 247:77–79.
Majewski et al. (1996) *J Invest Dermatol* 106(5):1114–1118.
Manetti et al. (1993) *J Exp Med* 177:1199.
Margolin (2000) *Semin Oncol* 27(2):194–203.
Marin et al. (1997) *Mol Med Today* 3:396.
Melero et al. (2001) *Trends Immunol* 22(3): 113–115.
Merrick et al. (1997) *Cancer Lett* 119(2):185–190.
Michel et al. (1997) *Biochem J* 328(Pt1):45–50.
Miklavcic et al. (1998) *Biophys J* 74:2152–2158.
Morgan et al. (1992) *Nuc Acids Res* 20:1293–1299.
Nabel (1997) "Vectors for Gene Therapy" in *Current Protocols in Human Genetics* on CD-ROM, John Wiley & Sons, New York, N.Y.
Narvaiza et al. (2000) *J Immunol* 164:3112–3122.
Nasu et al. (1999) *Gene Ther* 6:338–349.
Needleman & Wunsch (1970) *J Mol Biol* 48:443.
Neri et al. (1997) *Nat Bio Technology* 15:1271.
Neumann et al. (1982) *EMBO J* 1:841–845.
Nomura & Hasegawa (2000) *Anticancer Res* 20(6A):4073–4080.
O'Byrne et al. (2000) *Eur J Cancer* 36(2):151–169.
Ohtsuka et al. (1985) *J Biol Chem* 260:2605–2608.
Ohtsuka & Hata (2000) *Int J Hyperthermia* 16(3):231–245.
O'Reilly et al. (1994) *Cell* 79:315–328.
O'Reilly et al. (1997) *Cell* 88:277–285.
Overwijk et al. (2000) *Cancer J Sci Am* 6 Suppl 1:S76–80.
Park et al. (1997) *Proc Am Ass Canc Res* 38:342.
Pasqualini et al. (1997) *Nat Biotechnology* 15:542.
Pearson & Lipman (1988) *Proc Natl Acad Sci USA* 85:2444–2448.
Porter et al. (2001) *J Mol Endocrinol* 26(1):31–42.
Pützer et al. (1997) *Proc Natl Acad Sci USA* 94:10889–10894.
Repasky et al. (1999) *Infect Dis Obstet Gynecol* 7(1–2):91–97.
Richards et al. (1995) *Human Gene Ther* 6:881–893.
Robertson et al. (1992) *J Exp Med* 175:779.
Robins et al. (1985) *Cancer Res* 45(8):3937–3944.
Rome et al. (1994) *Arterioscler Thromb* 14(1):148–161.

Rose & Botstein (1983) *Meth Enzymol* 101:167–180.
Rossolini et al. (1994) *Mol Cell Probes* 8:91–98.
Ryffel (1997) *Immunopathol* 83:18–20.
Sadekova (1997) *Int J Radiat Biol* 72(6):653–660.
Sakamoto et al. (1991) *Cancer Res* 5:903–906.
Sambrook et al., eds. (1989) *Molecular Cloning: A Laboratory Manual*, Cold Spring Harbor Laboratory Press, Cold Spring Harbor, N.Y.
Samulski (1999) in Hendee, ed., *Biomedical Uses of Radiation*, pp. 1133–1233, VCH Publishers, Weinheim, Germany.
Sapozink et al. (1991) *Int J Radiat Oncol Biol Phys* 20(5):1109–1115.
Saqi et al. (1999) *Bioinformatics* 15(6):521–522.
Sato et al. (1995) *Clin Immunol Pathol* 74:35–43.
Schneider et al. (1982) *Proc Natl Acad Sci USA* 79:3047–3051.
Sersa et al. (2000) *Clin Cancer Res* 6:863–867.
Shanafelt et al. (2000) *Nat Biotechnol* 18(11):1197–1202.
Shepherd et al. (2000) *Neuroscience* 99(2):317–325.
Shirkey (1965) *JAMA* 193:443.
Sigel & Puri (1991) *J Clin Oncol* 9:694–704.
Silhavy et al. (1984) *Experiments with Gene Fusions*, Cold Spring Harbor Laboratory Press, Cold Spring Harbor, N.Y.
Smith & Waterman (1981) *Adv Appl Math* 2:482.
Sneed et al. (1991) *Neurosurgery* 28:206–215.
Spriggs & Yates (1992) in Bentler, ed., *Tumor Necrosis Factor: The Molecules and Their Emerging Roles in Medicine*, pp. 383–406 Raven Press, New York, N.Y.
Stephanou & Latchman (1999) *Gene Expr* 7(4–6):311–319.
Strik et al. (2000) *Anticancer Res* 20(6B):4457–4552.
Szewczenko-Pawlikowski et al. (1997) *Mol Cell Biochem* 177(1–2):145–152.
Takano et al. (1997) *Exp Cell Res* 237(1):38–45.
Thrall et al. (1986) *Cancer Res* 46(12 Pt 1):6229–6235.
Tijssen (1993) *Laboratory Techniques in Biochemistry and Molecular Biology-Hybridization with Nucleic Acid Probes*, part I chapter 2, Elsevier, New York, N.Y.
Tolsma et al. (1993) *J Cell Biol* 122:497–511.
Toyota et al. (1997) *Int J Hyperthermia* 13(5):497–506.
U.S. Pat. No. 4,235,871
U.S. Pat. No. 4,551,482
U.S. Pat. No. 4,554,101
U.S. Pat. No. 5,011,634
U.S. Pat. No. 5,213,804
U.S. Pat. No. 5,234,933
U.S. Pat. No. 5,326,902
U.S. Pat. No. 5,382,514
U.S. Pat. No. 5,574,142
U.S. Pat. No. 5,714,166
U.S. Pat. No. 5,858,784
U.S. Pat. No. 5,860,929
U.S. Pat. No. 5,942,385
U.S. Pat. No. 5,948,767
U.S. Pat. No. 5,955,291
U.S. Pat. No. 6,013,638
U.S. Pat. No. 6,022,737
U.S. Pat. No. 6,056,938
U.S. Pat. No. 6,059,727
U.S. Pat. No. 6,132,766
U.S. Pat. No. 6,136,295.
U.S. Pat. No. 6,197,333
U.S. Pat. No. 6,200,598
U.S. Pat. No. 6,210,707
U.S. Pat. No. 6,217,886
Valdagni & Amicetti (1994) *Int J Radiat Oncol Biol Phys* 28:163–169.
Vernon et al. (1996) *Int J Radiat Oncol Biol Phys* 35:731–744.
Viard et al. (1999) *J Invest Dermatol* 112(3):290–296.
Vicat et al. (2000) *Hum Gene Ther* 11:909–916.
Vivinus et al. (2001) *Eur J Biochem* 268(7):1908–1917.
Voest et al. (1995) *J Natl Cancer Inst* 87(8):581–586.
Voellmy et al. (1985) *Proc Natl Acad Sci USA* 82:4949–4953.
Weischelbaum et al. (1994) *Cancer Res* 54:4266–4269.
WO 93/25521
WO 95/00178
WO 97/47763
WO 98/00684
WO 99/42137
WO 00/78211
Walther & Stein (1999) *Mol Biotechnol* 13(1):21–28.
Waterman et al. (1991) *Int J Radiat Oncol Biol Phys* 20(5): 1099–1107.
Wolf et al. (1991) *J Immunol* 146:3074.
Woltering et al. (1991) *J Surg Res* 50:245–251.
Wu et al. (1993) *Microvasc Res* 46:231–253.
Yang (1992) *Crit Rev Biotech* 12(4):335–356.
Yao et al. (1999) *Blood* 93(5):1612–1621.
Yu et al. (2000) *Electrophoresis* 21(14):3058–3068.
Yuan et al. (1995) *Cancer Research* 555(17):3752–3756.
Yuan et al. (1994) *Cancer Research* 54:4564–4568.
Zhang et al. (1993) *Biotechniques* 15:868–872.
Zhang et al. (1997) *Pharmaceutical Res* 14:190–196.
Zhang et al. (1999) *Endocrinology* 140:2152–2158.

It will be understood that various details of the invention can be changed without departing from the scope of the invention. Furthermore, the foregoing description is for the purpose of illustration only, and not for the purpose of limitation—the invention being defined by the claims appended hereto.

What is claimed:

1. A method for promoting anti-tumor activity and reducing systemic toxicity associated with the anti-tumor activity in a warm-blooded vertebrate, the method comprising:
   (a) providing a construct comprising a polynucleotide encoding a functional IL12 polypeptide, wherein the polynucleotide is operatively linked to a heat-inducible promoter;
   (b) administering the construct intratumorally to a warm-blooded vertebrate; and
   (c) applying heat to a site of the tumor to express the functional IL12 polypeptide, whereby anti-tumor activity and reduced systemic toxicity as compared to a construct comprising a polynucleotide encoding a functional IL12 polypeptide operably linked to a constitutive promoter are observed.

2. The method of claim 1, wherein the functional IL12 polypeptide comprises a first subunit and a second subunit.

3. The method of claim 2, wherein the first subunit comprises:
   (a) a polypeptide encoded by a nucleic acid molecule of SEQ ID NO: 5;
   (b) a polypeptide encoded by a nucleic acid at least 95% identical to SEQ ID NO: 5;
   (c) a polypeptide having an amino acid sequence set forth as SEQ ID NO: 6;
   (d) a polypeptide having an amino acid sequence at least 95% identical to SEQ ID NO: 6; or
   (e) a polypeptide that has biologically functional equivalent amino acid substitution of SEQ ID No. 6.

4. The method of claim 2, wherein the second subunit comprises:
   (a) a polypeptide encoded by a nucleic acid molecule of SEQ ID NO: 7;
   (b) a polypeptide encoded by a nucleic acid at least 95% identical to SEQ ID NO: 7;
   (c) a polypeptide having an amino acid sequence set forth as SEQ ID NO: 8;
   (d) a polypeptide having an amino acid sequence at least 95% identical to SEQ ID NO: 8; or
   (e) a polypeptide that has biologically functional equivalent amino acid substitution of SEQ ID No. 8.

5. The method of claim 4, wherein the second subunit comprises a polypeptide selected from the group consisting of a polypeptide encoded by a nucleic acid at least 99% identical to SEQ ID NO: 7 and a polypeptide having an amino acid sequence at least 99% identical to SEQ ID NO: 8.

6. The method of claim 2, wherein:
   (a) the first subunit is encoded by a nucleic acid comprising:
      (i) a nucleotide sequence set forth as SEQ ID NO: 5; or
      (ii) a nucleotide sequence that is at least 95% identical to SEQ ID NO: 5; and
   (b) the second subunit is encoded by a nucleic acid comprising:
      (i) a nucleotide sequence set forth as SEQ ID NO: 7; or
      (ii) a nucleotide sequences that is at least 95% identical to SEQ ID NO: 7.

7. The method of claim 6, wherein the first subunit is encoded by a nucleic acid comprising a nucleotide sequence that is at least 99% identical to SEQ ID NO: 5.

8. The method of claim 6, wherein the second subunit is encoded by a nucleic acid comprising a nucleotide sequence that is at least 99% identical to SEQ ID NO: 7.

9. The method of claim 2, wherein the first subunit comprises a polypeptide selected from the group consisting of a polypeptide encoded by a nucleic acid at least 99% identical to SEQ ID NO: 5 and a polypeptide having an amino acid sequence at least 99% identical to SEQ ID NO: 6.

10. The method of claim 1, wherein the heat-inducible promoter comprises an hsp70 promoter.

11. The method of claim 10, wherein the hsp70 promoter comprises a human hsp70B promoter.

12. The method of claim 11, wherein the hsp70B promoter comprises:
   (a) the nucleotide sequence set forth as SEQ ID NO:13, or functional portion thereof; or
   (b) a nucleotide sequence at least 95% identical to SEQ ID NO:13.

13. The method of claim 1, further comprising providing radiotherapy at the site of the tumor, whereby anti-tumor activity is enhanced when compared to anti-tumor activity observed in response to radiotherapy alone.

14. The method of claim 13, wherein the radiotherapy is provided to the tumor.

15. The method of claim 1, wherein the applying of heat is to the tumor.

16. The method of claim 1, wherein the construct further comprises a polynucleotide encoding a functional B7.1 co-stimulatory molecule, and upon applying heat to the tumor, expression of both the IL12 polypeptide and the B7.1 co-stimulatory molecule occurs in the tumor, whereby anti-tumor activity is observed.

17. A method for promoting anti-tumor activity and reducing systemic toxicity associated with the anti-tumor activity in a warm-blooded vertebrate, the method comprising:

(a) providing a construct comprising a polynucleotide encoding a functional IL12 polypeptide comprising a first subunit and a second subunit, wherein:
   (i) the first subunit comprises a first polypeptide
      (a) encoded by a first nucleic acid molecule comprising a first nucleotide sequence as set forth in SEQ ID NO: 5; or
      (b) having a first amino acid sequence set forth as SEQ ID NO: 6;
   (ii) the second subunit comprises a second polypeptide
      (a) encoded by a second nucleic acid molecule comprising a second nucleotide sequence as set forth in SEQ ID NO: 7; or
      (b) having a second amino acid sequence set forth as SEQ ID NO: 8; and
   (iii) the polynucleotide is operatively linked to a heat-inducible promoter;
(b) administering the construct intratumorally to a warm-blooded vertebrate; and
(c) applying heat to a site of the tumor to express the functional IL12 polypeptide, whereby anti-tumor activity is observed, and whereby reduced systemic toxicity is observed as compared to administration of a construct that does not include a heat-inducible promoter.

* * * * *